(12) United States Patent
Ambati et al.

(10) Patent No.: US 8,846,386 B2
(45) Date of Patent: Sep. 30, 2014

(54) SVEGFR-2 AND ITS ROLE IN LYMPHANGIOGENESIS MODULATION

(75) Inventors: Jayakrishna Ambati, Lexington, KY (US); Rumulo J. C. Albuquerque, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 1015 days.

(21) Appl. No.: 12/338,728

(22) Filed: Dec. 18, 2008

(65) Prior Publication Data

US 2009/0186376 A1  Jul. 23, 2009

Related U.S. Application Data

(60) Provisional application No. 61/014,634, filed on Dec. 18, 2007.

(51) Int. Cl.
| | |
|---|---|
| *C12N 15/63* | (2006.01) |
| *C12N 15/85* | (2006.01) |
| *C07K 14/71* | (2006.01) |
| *G01N 33/566* | (2006.01) |
| *G01N 33/574* | (2006.01) |
| *A61K 38/00* | (2006.01) |

(52) U.S. Cl.
CPC ............ *C07K 14/71* (2013.01); *G01N 2500/02* (2013.01); *A61K 38/00* (2013.01); *G01N 2333/71* (2013.01); *G01N 33/566* (2013.01); *G01N 33/574* (2013.01)
USPC ....................................... 435/320.1; 435/325

(58) Field of Classification Search
None
See application file for complete search history.

(56) References Cited

U.S. PATENT DOCUMENTS

2010/0075891 A1 * 3/2010 Ayalon-Soffer et al. .......... 514/2

FOREIGN PATENT DOCUMENTS

WO    WO 01/31346    *   5/2001    ............. G01N 33/68

* cited by examiner

*Primary Examiner* — Celine Qian
(74) *Attorney, Agent, or Firm* — Crowell & Moring LLP

(57) ABSTRACT

Disclosed herein are nucleic acid molecules comprising a nucleotide sequence of sVEGF-2, proteins encoded by those sequences and antibodies that bind to the protein. Also disclosed are methods for inhibiting or enhancing expression or activity of sVEGFR-2 and methods for inhibiting graft rejection, particularly cornea graph rejection. Also described are methods for inhibiting lymphangiogenesis and lymphatic endothelial cell proliferation by administering an effective amount of sVEGFR-2 and methods for treating lymphedema by inhibiting the activity of sVEGFR-2.

4 Claims, 32 Drawing Sheets

Figure 1

```
CTGTGTTTCCTTAGATCGCGCGGACCGCTACCCGGCAGGACTGAAAGCCCAGACTGTGTCCC
GCAGCCGGGATAACCTGGCTGACCCGATTCCGCGGACACCGCTGCAGCCGCGGCTGGAGCCA
GGGCGCCGGTGCCCCGCGCTCTCCCGGTCTTGCGCTGCGGGGCGCATACCGCCTCTGTGA
CTTCTTTGCGGGCCAGGGACGGAGAAGGAGTCTGTGCCTGAGAACTGGGCTCTGTGCCCAGC
GCGAGGTGCAGGATGGAGAGCAAGGCGCTGCTAGCTGTCGCTCTGTGGTTCTGCGTGGAGAC
CCGAGCCGCCTCTGTGGGTTTGCCTGGCGATTTTCTCCATCCCCCCAAGCTCAGCACACAGA
AAGACATACTGACAATTTTGGCAAATACAACCCTTCAGATTACTTGCAGGGGACAGCGGGAC
CTGGACTGGCTTTGGCCCAATGCTCAGCGTGATTCTGAGGAAAGGGTATTGGTGACTGAATG
CGGCGGTGGTGACAGTATCTTCTGCAAAACACTCACCATTCCCAGGGTGGTTGGAAATGATA
CTGGAGCCTACAAGTGCTCGTACCGGGACGTCGACATAGCCTCCACTGTTTATGTCTATGTT
CGAGATTACAGATCACCATTCATCGCCTCTGTCAGTGACCAGCATGGCATCGTGTACATCAC
CGAGAACAAGAACAAAACTGTGGTGATCCCCTGCCGAGGGTCGATTTCAAACCTCAATGTGT
CTCTTTGCGCTAGGTATCCAGAAAAGAGATTTGTTCCGGATGGAAACAGAATTTCCTGGGAC
AGCGAGATAGGCTTTACTCTCCCCAGTTACATGATCAGCTATGCCGGCATGGTCTTCTGTGA
GGCAAAGATCAATGATGAAACCTATCAGTCTATCATGTACATAGTTGTGGTTGTAGGATATA
GGATTTATGATGTGATTCTGAGCCCCCCGCATGAAATTGAGCTATCTGCCGGAGAAAAACTT
GTCTTAAATTGTACAGCGAGAACAGAGCTCAATGTGGGCTTGATTTCACCTGGCACTCTCC
ACCTTCAAAGTCTCATCATAAGAAGATTGTAAACCGGGATGTGAAACCCTTTCCTGGGACTG
TGGCGAAGATGTTTTTGAGCACCTTGACAATAGAAAGTGTGACCAAGAGTGACCAAGGGGAA
TACACCTGTGTAGCGTCCAGTGGACGGATGATCAAGAGAAATAGAACATTTGTCCGAGTTCA
CACAAAGCCTTTTATTGCTTTCGGTAGTGGGATGAAATCTTTGGTGGAAGCCACAGTGGGCA
GTCAAGTCCGAATCCCTGTGAAGTATCTCAGTTACCCAGCTCCTGATATCAAATGGTACAGA
AATGGAAGGCCCATTGAGTCCAACTACACAATGATTGTTGGCGATGAACTCACCATCATGGA
AGTGACTGAAAGAGATGCAGGAAACTACACGGTCATCCTCACCAACCCCATTTCAATGGAGA
AACAGAGCCACATGGTCTCTCTGGTTGTGAATGTCCCACCCCAGATCGGTGAGAAAGCCTTG
ATCTCGCCTATGGATTCCTACCAGTATGGGACCATGCAGACATTGACATGCACAGTCTACGC
CAACCCTCCCCTGCACCACATCCAGTGGTACTGGCAGCTAGAAGAAGCCTGCTCCTACAGAC
CCGGCCAAACAAGCCCGTATGCTTGTAAAGAATGGAGACACGTGGAGGATTTCCAGGGGGA
AACAAGATCGAAGTCACCAAAAACCAATATGCCCTGATTGAAGGAAAAAACAAAACTGTAAG
TACGCTGGTCATCCAAGCTGCCAACGTGTCAGCGTTGTACAAATGTGAAGCCATCAACAAAG
CGGGACGAGGAGAGAGGGTCATCTCCTTCCATGTGATCAGGGGTCCTGAAATTACTGTGCAA
CCTGCTGCCCAGCCAACTGAGCAGGAGAGTGTGTCCCTGTTGTGCACTGCAGACAGAAATAC
GTTTGAGAACCTCACGTGGTACAAGCTTGGCTCACAGGCAACATCGGTCCACATGGGCGAAT
CACTCACACCAGTTTGCAAGAACTTGGATGCTCTTTGGAAACTGAATGGCACCATGTTTTCT
AACAGCACAAATGACATCTTGATTGTGGCATTTCAGAATGCCTCTCTGCAGGACCAAGGCGA
CTATGTTTGCTCTGCTCAAGATAAGAAGACCAAGAAAAGACATTGCCTGGTCAAACAGCTCA
TCATCCTAGGTATGGAGGCATCCCTGGGTGACAGAATTGCAATGCCTTAAATGCAGTGTGTT
TGAGTGTTGTAGTAGGCTGGCACACTCCTGGAAGCAGAGCAAAGCTAACAGTGGTGAGGTAA
GACATTAAAATTAGAAGACAGCTTGACTCTTTCTAGCCTTTAAGATGATGTCACTACTAGTA
TGTGCAAGGGATTAGCTTAAATCCAGAGAACTTCCTGTGGCATCCCTGGACATTCAGATGAT
TACAGTTAGCACATGTGTGTAATACTATTAGCAAAGAGAGGGTCAGAAGCTCAAAGTGATGA
CCCAGAAGGAGAGGGTGAGACTATAGGCAAATACCGGGTGGTCGTGCCATTGTGGTGTCTCC
AACTCCTGGGGATAAAA
```

Figure 1 (continued)

ATTGATCTTTGCTTGCTTACTGCCGTAATTTTAGTCAGAGAACACACTGGCACATACAAGGT
GGTCAATGGGATACCTGCTTCATGAAAAGTGTGATGAGGGTCTGAATTTAAGATCTAGAAGA
TTCCACGGAAGGGGTGCCACACTCATTGCCTGTACTCCTCTGGTAGCCTATGTGGTCTGCAG
TAGGTGAAGTTCAGTGAGATAAGTTTGGGATTAGAAAAAAAAAACTTTCACATTTCCTGTGG
GGATGCTAGCCTGTCTTGTCTAACCTTGTACTTTGCACAAAACCTAGGCAATCTCTGCTCTG
AGGATATCTGGTGAGTTTAGGAGGCATCTCTGTGCTTTTTTCCTGCCATTTTCTCCTTTCTT
TGTTGTGCTCTCTGAGGTTCTCGTGATGTGCATCTTCTCTGGTTTATAGTGTGAGAAAGGTG
AACTGCCCAGGCTAACTAATCTACATCAACATTTTACATGAATATCATTTTTAAGTGCTTTG
GCTTATCTGAGGGGGTGTTTGAAAATAGATGCTAACATATGATTGTTATTAAAAAGAAACTT
GGGGACAGAAGGACAGATGTTTCTGAGTGAAGTTGTTCCCAAGACCCTAGAGATCACACCAC
ACATAGGACCCGTTATATCAGGTTAACAGTAGCTGATCCAGATGAGGGCAAGTTTAGAAGGG
AGCTCTGGGCTTAGCCATGACCAGGAAGTTTCCTATCACAGTCAGTGGGTATGCTTCTATAA
GGATGCCTCTGTTGTTTCCAAAACTCTGTTCTTGGAAGTAGGCCAGAGCCAAGTACACTTGT
TTAAACTCTGATATATATAGTACATGGTGGAAATGACCACGTTCTGCTAAGTGTGGAAGAGA
TTCTCTCAACATGATTCTTCCTGATGCTCATCAATGTTTCTACTGCAGTTGGGTGATTTTCA
GGAGCACGGTAAAGCTCAGGCTTTGCTGTCCATGTAGACAAATGGCCTTGGCTTTTCGTAGG
ATATTATTGTTTGGTTTGTGTTTGAGTGGAAACCACGAAGGAGTTTTAGGCCCATCAGACTC
TACTATTATCTCAACCATTTACTTAGTTATAGGGTAAGGTGCTTAACCTGGACTGCAATCAC
ATCACATAAAAATAAGGCTAATGGCGTGGCTCTCATTATATGTGACTGACAGTAAATATTAG
AAATGATATAGTTATCCAAAGTTATGTAAGTCACTCCTTACATAATTGTCCTGAAGTTTTGT
CTTTCCTAAGGGAAAACATGAATTTTACTCTTAGAGGCTACAACTTTCCAGAGAAGAAGTTA
CTCTTAGGGAAAGCCTTGTGGAATTGGAGGGAAATAAATCCTCTAACCTGAATAAAACCATC
CCCAAGAAAAAAAAAAAAAAAAAAAAAAAAAAAAAAAAAA

Figure 2

ATGGAGAGCAAGGCGCTGCTAGCTGTCGCTCTGTGGTTCTGCGTGGAGACCCGAGCCGCCTC
TGTGGGTTTGCCTGGCGATTTTCTCCATCCCCCCAAGCTCAGCACACAGAAAGACATACTGA
CAATTTTGGCAAATACAACCCTTCAGATTACTTGCAGGGGACAGCGGGACCTGGACTGGCTT
TGGCCCAATGCTCAGCGTGATTCTGAGGAAAGGGTATTGGTGACTGAATGCGGCGGTGGTGA
CAGTATCTTCTGCAAAACACTCACCATTCCCAGGGTGGTTGGAAATGATACTGGAGCCTACA
AGTGCTCGTACCGGGACGTCGACATAGCCTCCACTGTTTATGTCTATGTTCGAGATTACAGA
TCACCATTCATCGCCTCTGTCAGTGACCAGCATGGCATCGTGTACATCACCGAGAACAAGAA
CAAAACTGTGGTGATCCCCTGCCGAGGGTCGATTTCAAACCTCAATGTGTCTCTTTGCGCTA
GGTATCCAGAAAAGAGATTTGTTCCGGATGGAAACAGAATTTCCTGGGACAGCGAGATAGGC
TTTACTCTCCCCAGTTACATGATCAGCTATGCCGGCATGGTCTTCTGTGAGGCAAAGATCAA
TGATGAAACCTATCAGTCTATCATGTACATAGTTGTGGTTGTAGGATATAGGATTTATGATG
TGATTCTGAGCCCCCCGCATGAAATTGAGCTATCTGCCGGAGAAAAACTTGTCTTAAATTGT
ACAGCGAGAACAGAGCTCAATGTGGGGCTTGATTTCACCTGGCACTCTCCACCTTCAAAGTC
TCATCATAAGAAGATTGTAAACCGGGATGTGAAACCCTTTCCTGGGACTGTGGCGAAGATGT
TTTTGAGCACCTTGACAATAGAAAGTGTGACCAAGAGTGACCAAGGGGAATACACCTGTGTA
GCGTCCAGTGGACGGATGATCAAGAGAAATAGAACATTTGTCCGAGTTCACACAAAGCCTTT
TATTGCTTTCGGTAGTGGGATGAAATCTTTGGTGGAAGCCACAGTGGGCAGTCAAGTCCGAA
TCCCTGTGAAGTATCTCAGTTACCCAGCTCCTGATATCAAATGGTACAGAAATGGAAGGCCC
ATTGAGTCCAACTACACAATGATTGTTGGCGATGAACTCACCATCATGGAAGTGACTGAAAG
AGATGCAGGAAACTACACGGTCATCCTCACCAACCCCATTTCAATGGAGAAACAGAGCCACA
TGGTCTCTCTGGTTGTGAATGTCCCACCCCAGATCGGTGAGAAAGCCTTGATCTCGCCTATG
GATTCCTACCAGTATGGGACCATGCAGACATTGACATGCACAGTCTACGCCAACCCTCCCCT
GCACCACATCCAGTGGTACTGGCAGCTAGAAGAAGCCTGCTCCTACAGACCCGGCCAAACAA
GCCCGTATGCTTGTAAAGAATGGAGACACGTGGAGGATTTCCAGGGGGGAAACAAGATCGAA
GTCACCAAAAACCAATATGCCCTGATTGAAGGAAAAAACAAAACTGTAAGTACGCTGGTCAT
CCAAGCTGCCAACGTGTCAGCGTTGTACAAATGTGAAGCCATCAACAAAGCGGGACGAGGAG
AGAGGGTCATCTCCTTCCATGTGATCAGGGGTCCTGAAATTACTGTGCAACCTGCTGCCCAG
CCAACTGAGCAGGAGAGTGTGTCCCTGTTGTGCACTGCAGACAGAAATACGTTTGAGAACCT
CACGTGGTACAAGCTTGGCTCACAGGCAACATCGGTCCACATGGGCGAATCACTCACACCAG
TTTGCAAGAACTTGGATGCTCTTTGGAAACTGAATGGCACCATGTTTTCTAACAGCACAAAT
GACATCTTGATTGTGGCATTTCAGAATGCCTCTCTGCAGGACCAAGGCGACTATGTTTGCTC
TGCTCAAGATAAGAAGACCAAGAAAAGACATTGCCTGGTCAAACAGCTCATCATCCTAGGTA
TGGAGGCATCCCTGGGTGACAGAATTGCAATGCCTTAA

Figure 3

MESKALLAVALWFCVETRAASVGLPGDFLHPPKLSTQKDILTILANTTLQITCRGQRDLDWL
WPNAQRDSEERVLVTECGGGDSIFCKTLTIPRVVGNDTGAYKCSYRDVDIASTVYVYVRDYR
SPFIASVSDQHGIVYITENKNKTVVIPCRGSISNLNVSLCARYPEKRFVPDGNRISWDSEIG
FTLPSYMISYAGMVFCEAKINDETYQSIMYIVVVGYRIYDVILSPPHEIELSAGEKLVLNC
TARTELNVGLDFTWHSPPSKSHHKKIVNRDVKPFPGTVAKMFLSTLTIESVTKSDQGEYTCV
ASSGRMIKRNRTFVRVHTKPFIAFGSGMKSLVEATVGSQVRIPVKYLSYPAPDIKWYRNGRP
IESNYTMIVGDELTIMEVTERDAGNYTVILTNPISMEKQSHMVSLVVNVPPQIGEKALISPM
DSYQYGTMQTLTCTVYANPPLHHIQWYWQLEEACSYRPGQTSPYACKEWRHVEDFQGGNKIE
VTKNQYALIEGKNKTVSTLVIQAANVSALYKCEAINKAGRGERVISFHVIRGPEITVQPAAQ
PTEQESVSLLCTADRNTFENLTWYKLGSQATSVHMGESLTPVCKNLDALWKLNGTMFSNSTN
DILIVAFQNASLQDQGDYVCSAQDKKTKKRHCLVKQLIILGMEASLGDRIAMP

Figure 4

ATGCAGAGCAAGGTGCTGCTGGCCGTCGCCCTGTGGCTCTGCGTGGAGACCCGGGCCGCCTC
TGTGGGTTTGCCTAGTGTTTCTCTTGATCTGCCCAGGCTCAGCATACAAAAAGACATACTTA
CAATTAAGGCTAATACAACTCTTCAAATTACTTGCAGGGGACAGAGGGACTTGGACTGGCTT
TGGCCCAATAATCAGAGTGGCAGTGAGCAAAGGGTGGAGGTGACTGAGTGCAGCGATGGCCT
CTTCTGTAAGACACTCACAATTCCAAAAGTGATCGGAAATGACACTGGAGCCTACAAGTGCT
TCTACCGGGAAACTGACTTGGCCTCGGTCATTTATGTCTATGTTCAAGATTACAGATCTCCA
TTTATTGCTTCTGTTAGTGACCAACATGGAGTCGTGTACATTACTGAGAACAAAACAAAAC
TGTGGTGATTCCATGTCTCGGGTCCATTTCAAATCTCAACGTGTCACTTTGTGCAAGATACC
CAGAAAAGAGATTTGTTCCTGATGGTAACAGAATTTCCTGGGACAGCAAGAAGGGCTTTACT
ATTCCCAGCTACATGATCAGCTATGCTGGCATGGTCTTCTGTGAAGCAAAAATTAATGATGA
AAGTTACCAGTCTATTATGTACATAGTTGTCGTTGTAGGGTATAGGATTTATGATGTGGTTC
TGAGTCCGTCTCATGGAATTGAACTATCTGTTGGAGAAAAGCTTGTCTTAAATTGTACAGCA
AGAACTGAACTAAATGTGGGGATTGACTTCAACTGGGAATACCCTTCTTCGAAGCATCAGCA
TAAGAAACTTGTAAACCGAGACCTAAAAACCCAGTCTGGGAGTGAGATGAAGAAATTTTTGA
GCACCTTAACTATAGATGGTGTAACCCGGAGTGACCAAGGATTGTACACCTGTGCAGCATCC
AGTGGGCTGATGACCAAGAAGAACAGCACATTTGTCAGGGTCCATGAAAAACCTTTTGTTGC
TTTTGGAAGTGGCATGGAATCTCTGGTGGAAGCCACGGTGGGGGAGCGTGTCAGAATCCCTG
CGAAGTACCTTGGTTACCCACCCCCAGAAATAAAATGGTATAAAAATGGAATACCCCTTGAG
TCCAATCACACAATTAAAGCGGGGCATGTACTGACGATTATGGAAGTGAGTGAAAGAGACAC
AGGAAATTACACTGTCATCCTTACCAATCCCATTTCAAAGGAGAAGCAGAGCCATGTGGTCT
CTCTGGTTGTGTATGTCCCACCCCAGATTGGTGAGAAATCTCTAATCTCTCCTGTGGATTCC
TACCAGTACGGCACCACTCAAACGCTGACATGTACGGTCTATGCCATTCCTCCCCCGCATCA
CATCCACTGGTATTGGCAGTTGGAGGAAGAGTGCGCCAACGAGCCCAGCCAAGCTGTCTCAG
TGACAAACCCATACCCTTGTGAAGAATGGAGAAGTGTGGAGGACTTCCAGGGAGGAAATAAA
ATTGAAGTTAATAAAAATCAATTTGCTCTAATTGAAGGAAAAAACAAAACTGTAAGTACCCT
TGTTATCCAAGCGGCAAATGTGTCAGCTTTGTACAAATGTGAAGCGGTCAACAAAGTCGGGA
GAGGAGAGAGGGTGATCTCCTTCCACGTGACCAGGGGTCCTGAAATTACTTTGCAACCTGAC
ATGCAGCCCACTGAGCAGGAGAGCGTGTCTTTGTGGTGCACTGCAGACAGATCTACGTTTGA
GAACCTCACATGGTACAAGCTTGGCCCACAGCCTCTGCCAATCCATGTGGGAGAGTTGCCCA
CACCTGTTTGCAAGAACTTGGATACTCTTTGGAAATTGAATGCCACCATGTTCTCTAATAGC
ACAAATGACATTTTGATCATGGAGCTTAAGAATGCATCCTTGCAGGACCAAGGAGACTATGT
CTGCCTTGCTCAAGACAGGAAGACCAAGAAAAGACATTGCGTGGTCAGGCAGCTCACAGTCC
TAGGTAGGGAGACAATTCTGGATCATTGTGCAGAG⬚CAGTTGGAATGCCTTAA

Figure 5

MQSKVLLAVALWLCVETRAASVGLPSVSLDLPRLSIQKDILTIKANTTLQITCRGQRDLD
WLWPNNQSGSEQRVEVTECSDGLFCKTLTIPKVIGNDTGAYKCFYRETDLASVIYVYVQD
YRSPFIASVSDQHGVVYITENKNKTVVIPCLGSISNLNVSLCARYPEKRFVPDGNRISWD
SKKGFTIPSYMISYAGMVFCEAKINDESYQSIMYIVVVVGYRIYDVVLSPSHGIELSVGE
KLVLNCTARTELNVGIDFNWEYPSSKHQHKKLVNRDLKTQSGSEMKKFLSTLTIDGVTRS
DQGLYTCAASSGLMTKKNSTFVRVHEKPFVAFGSGMESLVEATVGERVRIPAKYLGYPPP
EIKWYKNGIPLESNHTIKAGHVLTIMEVSERDTGNYTVILTNPISKEKQSHVVSLVVYVP
PQIGEKSLISPVDSYQYGTTQTLTCTVYAIPPPHHIHWYWQLEEECANEPSQAVSVTNPY
PCEEWRSVEDFQGGNKIEVNKNQFALIEGKNKTVSTLVIQAANVSALYKCEAVNKVGRGE
RVISFHVTRGPEITLQPDMQPTEQESVSLWCTADRSTFENLTWYKLGPQPLPIHVGELPT
PVCKNLDTLWKLNATMFSNSTNDILIMELKNASLQDQGDYVCLAQDRKTKKRHCVVRQLT
VLGRETILDHCAEAVGMP

Figure 6

ATGGCGAGCAAGGTGCTGCTGGCCGTCGCCCTGTGGCTCTGCGTGGAGACCCGGGCCGCCTC
TGTGGGTTTGCCTAGTGTTTCTCTTGATCTGCCCAGGCTCAGCATACAAAAAGACATACTTA
CAATTAAGGCTAATACAACTCTTCAAATTACTTGCAGGGGACAGAGGGACTTGGACTGGCTT
TGGCCCAATAATCAGAGTGGCAGTGAGCAAAGGGTGGAGGTGACTGAGTGCAGCGATGGCCT
CTTCTGTAAGACACTCACAATTCCAAAAGTGATCGGAAATGACACTGGAGCCTACAAGTGCT
TCTACCGGGAAACTGACTTGGCCTCGGTCATTTATGTCTATGTTCAAGATTACAGATCTCCA
TTTATTGCTTCTGTTAGTGACCAACATGGAGTCGTGTACATTACTGAGAACAAAAACAAAAC
TGTGGTGATTCCATGTCTCGGGTCCATTTCAAATCTCAACGTGTCACTTTGTGCAAGGTACC
CAGAAAAGAGATTTGTTCCTGATGGTAACAGAATTTCCTGGGACAGCAAGAAGGGCTTTACT
ATTCCCAGCTATATGATCAGCTATGCTGGCATGGTCTTCTGTGAAGCAAAAATTAATGATGA
AAGTTACCAGTCTATTATGTACATAGTTGTGGTTGTAGGGTATAGGATTTATGATGTGGTTC
TGAGTCCGTCTCATGGAGTTGAACTATCTGTTGGAGAGAAGCTTGTCTTAAATTGTACAGCA
AGAACTGAACTAAATGTGGGGATTGACTTCAACTGGGAATACCCTTCTTCGAAGCATCAGCA
TAAGAAACTTGTAAACCGAGATCTAAAAACCCAGTCTGGGAGTGAGATGAAGAAATTTTTGA
GCACCTTAACTATAGATGGTGTAACCCGGAGTGACCAAGGATTGTACACCTGTGCAGCGTCC
AGTGGGCTGATGACCAAGAAGAACAGCACATTTGTCAGGGTCCATGAAAAACCTTTTGTTGC
TTTTGGAAGTGGCATGGAATCTCTGGTGGAAGCCACGGTGGGGAGCGTGTCAGAATCCCTG
TGAAGTACCTTGGTTACCCGCCCCAGAAATAAAATGGTATAAAAATGGAATACCCCTTGAG
TCCAATCACACAGTTAAAGTGGGGCATGTGCTGACGATCATGGAAGTGAGCGAAAGAGACAC
AGGAAATTACACTGTCATCCTTACCAATCCCATTTCAAAGGAGAAGCAGAGTCACGTGGTCT
CTCTGGTTGTGTATGTCCCACCCCAGATTGGTGAGAAATCTCTGATCTCTCCTGTGGATTCC
TACCAGTACGGCACCACTCAAACGCTGACATGTACGGTCTACGCTATTCCTCCCCCGCATCA
CATCCACTGGTATTGGCAGTTGGAGGAAGAGTGCCCCAACGAGCCCAGCCAAGCTGTCTCAG
TGACAAACCCATACCCTTGTGAAGAATGGAGAAGTGTGGAGGACTTCCAGGGAGGAAATAAA
ATTGAAGTCAATAAAAATCAATTTGCTCTAATTGAAGGAAAAAACAAAACTGTAAGTACCCT
TGTTATCCAAGCGGCAAATGTGTCAGCTTTGTACAAATGTGAAGCGGTCAACAAAGTCGGGA
GAGGAGAGAGGGTGATCTCCTTCCATGTTACCAGGGGTCCTGAAATTACTTTGCAACCTGAC
TTGCAGCCCACTGAACAGGAGAGCGTGTCTTTGTGGTGCACTGCAGACAAATCTACATTTGA
GAACCTCACATGGTACAAGCTTGGCCCACAGCCTCTGCCAGTCCACGTGGGAGAGTTGCCCA
CACCTGTTTGCAAGAACTTGGATACTCTTTGGAAATTGAATGCCACTATATTCTCTAATAGC
ACAAATGACATTTTGATCATGGAGCTTAAGAATGCATCCTTGCAGGACCAAGGAGACTATGT
CTGCGTTGCTCAAGACAGGAAGACCAAGAAAAGACATTGCGTGGTCAGGCAGCTCACAGTCC
TCGGTAGGGAGACAATTCTGGATCATTGTGTAGGGCAGTTGGAATGCCTTAA

Figure 7

MASKVLLAVALWLCVETRAASVGLPSVSLDLPRLSIQKDILTIKANTTLQITCRGQRDLD
WLWPNNQSGSEQRVEVTECSDGLFCKTLTIPKVIGNDTGAYKCFYRETDLASVIYVYVQD
YRSPFIASVSDQHGVVYITENKNKTVVIPCLGSISNLNVSLCARYPEKRFVPDGNRISWD
SKKGFTIPSYMISYAGMVFCEAKINDESYQSIMYIVVVVGYRIYDVVLSPSHGVELSVGE
KLVLNCTARTELNVGIDFNWEYPSSKHQHKKLVNRDLKTQSGSEMKKFLSTLTIDGVTRS
DQGLYTCAASSGLMTKKNSTFVRVHEKPFVAFGSGMESLVEATVGERVRIPVKYLGYPPP
EIKWYKNGIPLESNHTVKVGHVLTIMEVSERDTGNYTVILTNPISKEKQSHVVSLVVYVP
PQIGEKSLISPVDSYQYGTTQTLTCTVYAIPPPHHIHWYWQLEEECPNEPSQAVSVTNPY
PCEEWRSVEDFQGGNKIEVNKNQFALIEGKNKTVSTLVIQAANVSALYKCEAVNKVGRGE
RVISFHVTRGPEITLQPDLQPTEQESVSLWCTADKSTFENLTWYKLGPQPLPVHVGELPT
PVCKNLDTLWKLNATIFSNSTNDILIMELKNASLQDQGDYVCVAQDRKTKKRHCVVRQLT
VLGRETILDHCVGAVGMP

Figure 8

```
ATGGAGAGCAGGGCGCTGCTAGCTGTCGCTCTGTGGTTCTGCGTGGAGACCCGAGCCGCCTC
TGTGGGTTTGCCTGGCGATTCCCTCCATCCACCCAAGCTCAGCACACAAAAAGACATACTTA
CAATTTTGGCAAATACAACCCTTCAGATTACTTGCAGGGGACAGAGGGACCTGGATTGGCTT
TGGCCCAACACTCCGCGTGACTCTGAGGAAAGGGTGTTGGTGACTGAGTGTGGCGACAGTAT
CTTCTGCAAGACACTCACAGTTCCCAGAGTGGTTGGAAATGATACTGGAGCCTACAAGTGCT
TCTATCGGGACACCGATGTCTCCTCCATCGTTTATGTCTATGTTCAAGATCACAGGTCACCA
TTCATCGCCTCTGTCAGTGACGAGCATGGCATCGTGTACATCACTGAGAACAAGAACAAAAC
TGTGGTGATCCCATGCCGAGGGTCGATTTCAAACCTCAACGTGTCACTTTGTGCTAGGTATC
CAGAAAAGAGATTTGTTCCGGATGGAAACAGAATTTCCTGGGACAGCGAGAAAGGCTTTACT
ATCCCCAGTTACATGATCAGCTATGCCGGCATGGTCTTCTGTGAGGCAAAGATTAATGATGA
AACGTATCAGTCTATCATGTACATAGTTCTGGTTGTAGGATATAGGATTTATGATGTGGTCC
TGAGCCCCCCTCATGAAATTGAGCTATCTGCCGGAGAAAAGCTTGTCTTAAATTGTACAGCA
AGAACAGAGCTCAACGTGGGGCTTGATTTCAGCTGGCAATTCCCGTCCTCAAAGCATCAGCA
TAAGAAGATTGTAAACCGGGATGTGAAATCCCTTCCTGGGACTGTGGCAAAGATGTTTTTGA
GCACCTTGACCATAGACAGTGTGACCAAGAGTGACCAAGGAGAATACACCTGCACAGCGTAC
AGTGGACTGATGACCAAGAAAAATAAAACATTTGTCCGAGTTCATACAAAACCTTTTATTGC
TTTTGGTAGCGGGATGAAATCTTTGGTGGAAGCCACTGTGGGCAGCCAAGTCCGAATCCCTG
TGAAGTATCTCAGTTACCCAGCTCCTGATATCAAATGGTACAGAAATGGACGACCCATTGAG
TCCAATTACACAATGATCGTTGGTGATGAACTCACCATCATGGAAGTGAGTGAAAGAGATGC
GGGAAACTACACGGTCATCCTCACCAATCCCATTTCAATGGAGAAACAGAGCCACATGGTCT
CTCTGGTTGTGAATGTTCCACCCCAGATCGGTGAGAAAGCCTTGATCTCTCCTATGGATTCC
TACCAGTATGGCACCATGCAGACGCTGACATGCACAGTCTATGCCAACCCTCCCCTGCACCA
CATCCAATGGTACTGGCAGCTAGAAGAAGCATGCTCCTACAGGCCCAGCCAAACAAACCCAT
ATACTTGTAAAGAATGGAGACACGTGAAGGATTTCCAGGGGGGAAATAAGATCGAAGTCACC
AAAAACCAATATGCCCTAATTGAAGGAAAAAACAAAACTGTAAGTACTCTGGTCATCCAGGC
TGCCTACGTGTCCGCATTATACAAATGTGAAGCCATCAACAAAGCAGGACGAGGAGAGAGGG
TCATCTCCTTCCATGTGATCAGGGGTCCTGAAATTACTGTCCAGCCTGCTACCCAGCCAACC
GAGCGGGAGAGTATGTCTTTATTGTGCACTGCAGATAGAAACACGTTTGAGAACCTCACGTG
GTACAAGCTTGGCTCACAGGCAACATCGGTCCACATGGGCGAATCACTCACACCAGTTTGCA
AGAACTTGGACGCTCTTTGGAAACTGAATGGCACCGTGTTTTCTAACAGCACAAACGACATC
TTGATTGTGGCATTCCAGAATGCCTCCCTGCAGGACCAAGGCAACTATGTCTGCTCTGCTCA
AGACAAGAAGACCAAGAAAAGACATTGCCTAGTCAAGCAGCTCGTCATCCTAG**GTATGGAGG
GACCCCTGGTTGATGGGGTTGCAATGCCTTAA**
```

Figure 9

MESRALLAVALWFCVETRAASVGLPGDSLHPPKLSTQKDILTILANTTLQITCRGQRDLD
WLWPNTPRDSEERVLVTECGDSIFCKTLTVPRVVGNDTGAYKCFYRDTDVSSIVYVYVQD
HRSPFIASVSDEHGIVYITENKNKTVVIPCRGSISNLNVSLCARYPEKRFVPDGNRISWD
SEKGFTIPSYMISYAGMVFCEAKINDETYQSIMYIVLVVGYRIYDVVLSPPHEIELSAGE
KLVLNCTARTELNVGLDFSWQFPSSKHQHKKIVNRDVKSLPGTVAKMFLSTLTIDSVTKS
DQGEYTCTAYSGLMTKKNKTFVRVHTKPFIAFGSGMKSLVEATVGSQVRIPVKYLSYPAP
DIKWYRNGRPIESNYTMIVGDELTIMEVSERDAGNYTVILTNPISMEKQSHMVSLVVNVP
PQIGEKALISPMDSYQYGTMQTLTCTVYANPPLHHIQWYWQLEEACSYRPSQTNPYTCKE
WRHVKDFQGGNKIEVTKNQYALIEGKNKTVSTLVIQAAYVSALYKCEAINKAGRGERVIS
FHVIRGPEITVQPATQPTERESMSLLCTADRNTFENLTWYKLGSQATSVHMGESLTPVCK
NLDALWKLNGTVFSNSTNDILIVAFQNASLQDQGNYVCSAQDKKTKKRHCLVKQLVILGM
EGPLVDGVAMP

Figure 10

```
ATGGAGAGCAAGGCGCTGCTGGCCCTTGCTCTGTGGCTCTGCGTGGAGACCCGGGCTGCCTC
TGTGGGTTTTTCTAGTGTTTCCCTTGATCCCCCAGGCTCAGCATCCAAAAAGACATACTTA
GAGTTATGGCTAACACAACGCTTCAGATTACTTGCAGGGGTCAGAGGGACTTGCAGTGGCTC
TGGCCCAACAATCAGAGCAGCTCTGAGAAAAGAGTGGAGGTCACAGACTGCAGTGATGGCGT
CTTCTGTAAGATGCTCACAATTTCAGAAGTGATTGGAAATGATACTGGAGCCTACAAGTGCT
TCTACCAGGACACTGACATGGGCTCCGTTCTTTATGTGTATGTTCAAGATTACAGGTCTCCG
TTTATTGCTTCTGTTAGCGACCAGCATGAAGTTGTGTACATCACTGAGAACAAAAACAAAAC
TGTGGTGATTCCGTGTTTGGGACTGTTTCAGACCTCAATGTGTCACTCTGTGCAAGGTATC
CAGAAAAAAGATTTGTACCTGATGGTAACAGAATTTCCTGGGACAGCCAGAAAGGCTTCAGT
ATTCCCAGCTATATGATCAGTTATGCTGGCGTGGTCTTCTGCGAAGCAAAAATCAATGATGA
AAGTTACCAGTCTATTATGTACATAATTGTGGTTATAGGGTACAAGATTTATGATGTGGTTC
TGAGCCCCCCTCACGGAGTCGAGCTGTCTGTTGGAGAGAAGCTCATCTTAAACTGTACGGCA
AGAACTGAGCTAAATGTGGGGATCGACTTCCACTGGGAATACCCTTCTTTGAAGCATCAGCA
TAAAAAACTTATAAACCGGGACCTAAAAACCCAGTCTGGGACTGAAATGAAGAAGTTTTTGA
GCACCTTGACTATAGATGGTGTAACCCGGAGTGACCAGGGGTGGTATATCTGTGCAGCTTCC
AGTGGGCTGATGACCAAGAAGAACAGCACGTTTGTCCGGGTACATGAAAAGCCTTTTGTTGC
TTTCGGTAGTGGCATGGAATCCTTGGTGGAAGCCACCGTGGGGGAACGTGTGAGAGTCCCTG
TCAAGTACCTTGGTTACCCTCCTCCAGAAATAAAATGGTATAAAAATGGAAGACCCATTGAG
TCCAATCACACAGTTAAAGTGGGACATGTGCTGACTATTATGGAAGTGAGTGAGAAAGATAC
AGGAAATTACACTGTCATTCTTACCAATCCCATTTCAAAGGAGAAACAGAGCCACATGGTAT
CTCTGGTGGTGAATGTCCCACCTCAGATTGGTGAGAAATCTCTGCTGTCTCCGTGGACTCT
TACCAGTACGGCACTTCCCAAACGCTGACGTGCACGGTCTACGCCGTTCCTCCCCCAAGTCA
CATTCGCTGGTACTGGCAGCTGGAGACGGAGTGCACCTACCAGCCCACCCTCACTGCCTTAA
CGACAAACCCATACACTTGTAAGGAATGGAGAAACGTGGAGGACTTCCAGGGGGGAAACAAA
ATCGAAGTCAACAAAAATCAGATTGCCCTAATTGAAGGAAGAAACAAAACTGTAAGTACTCT
TGTTATCCAAGCGGCCAATGTGTCTGCTTTGTATAAATGTGAAGCAGTGAACAAAGCTGGAA
GAGGAGAGAGGGTTATCTCCTTCCATGTGACCAGGGGTCCTGAAATCACACTGCAACCTGGC
ATCCAGCCCACCGAGCAGGAGAATGTGTCTCTGTGGTGCTCTGCGGACAGAACTATGTTTGA
GAACCTCACGTGGTACAAACTCGGCCCACAGGCCCTGCCCATCCACATGGGCGATTTACCCA
CACCTGTCTGCAAGAACTTGGATGCTCTTTGGAAAATGAATGCCACCATGAACTCTAACGGC
ACAAATGACATCTTGATCTTGGAGCTGCAGAATGCATCCTTGCAGGACCAAGGAGACTATGT
CTGCTTTGCTCAGGACAGGAAGACTAAGAAAAGACATTGTGTGGCCAGGCAGCTCACAGTCC
TAGGTAGGGCAGTCACTCTGGACCATCCAGAGGCAGTTGGGTTGCCTTCAATGTAA
```

Figure 11

MESKALLALALWLCVETRAASVGFSSVSLDPPRLSIQKDILRVMANTTLQITCRGQRDLQ
WLWPNNQSSSEKRVEVTDCSDGVFCKMLTISEVIGNDTGAYKCFYQDTDMGSVLYVYVQD
YRSPFIASVSDQHEVVYITENKNKTVVIPCLGTVSDLNVSLCARYPEKRFVPDGNRISWD
SQKGFSIPSYMISYAGVVFCEAKINDESYQSIMYIIVVIGYKIYDVVLSPPHGVELSVGE
KLILNCTARTELNVGIDFHWEYPSLKHQHKKLINRDLKTQSGTEMKKFLSTLTIDGVTRS
DQGWYICAASSGLMTKKNSTFVRVHEKPFVAFGSGMESLVEATVGERVRVPVKYLGYPPP
EIKWYKNGRPIESNHTVKVGHVLTIMEVSEKDTGNYTVILTNPISKEKQSHMVSLVVNVP
PQIGEKSLLSPVDSYQYGTSQTLTCTVYAVPPPSHIRWYWQLETECTYQPTLTALTTNPY
TCKEWRNVEDFQGGNKIEVNKNQIALIEGRNKTVSTLVIQAANVSALYKCEAVNKAGRGE
RVISFHVTRGPEITLQPGIQPTEQENVSLWCSADRTMFENLTWYKLGPQALPIHMGDLPT
PVCKNLDALWKMNATMNSNGTNDILILELQNASLQDQGDYVCFAQDRKTKKRHCVARQLT
VLGRAVTLDHPEAVGLPSM

Figure 12

| | | |
|---|---|---|
| Mouse | GTATGGAGGCATCCCTGGGTGACAGAATTGCAATGCCT | (SEQ ID NO:12) |
| Human | GTAGGGAGACAATTCTGGATCATTGTGCAGAGGCAGTTGGAATGCCT | (SEQ ID NO:13) |
| Monkey | GTAGGGAGACAATTCTGGATCATTGTGTAGGGGCAGTTGGAATGCCT | (SEQ ID NO:14) |
| Rat | GTATGGAGGGACCCCTGGTTGATGGGGTTGCAATGCCT | (SEQ ID NO:15) |
| Cow | GTAGGGCAGTCACTCTGGACCATCCAGAGGCAGTTGGGTTGCCTTCAATG | (SEQ ID NO:16) |

Figure 13

| | | |
|---|---|---|
| Mouse | GMEASLGDRIAMP | (SEQ ID NO:17) |
| Human | GRETILDHCAEAVGMP | (SEQ ID NO:18) |
| Monkey | GRETILDHCVGAVGMP | (SEQ ID NO:19) |
| Rat | GMEGPLVDGVAMP | (SEQ ID NO:20) |
| Cow | GRAVTLDHPEAVGLPSM | (SEQ ID NO:21) |

Figure 31

SEQUENCE LISTING

<160> NUMBER OF SEQ ID NOS: 47

<210> SEQ ID NO 1
<211> LENGTH: 4025
<212> TYPE: DNA
<213> ORGANISM: Mus sp.

<400> SEQUENCE: 1

```
ctgtgtttcc ttagatcgcg cggaccgcta cccggcagga ctgaaagccc agactgtgtc      60
ccgcagccgg gataacctgg ctgacccgat tccgcgcgaca ccgctgcagc cgcggctgga    120
gccagggcgc cggtgccccg cgctctcccc ggtcttgcgc tgcggggggcg cataccgcct    180
ctgtgacttc tttgcgggcc agggacggag aaggagtctg tgcctgagaa ctgggctctg    240
tgcccagcgc gaggtgcagg atggagagca aggcgctgct agctgtcgct ctgtggttct    300
gcgtggagac ccgagccgcc tctgtgggtt gcctggcga ttttctccat ccccccaagc     360
tcagcacaca gaaagacata ctgacaattt tggcaaatac aacccttcag attacttgca    420
ggggacagcg ggacctggac tggctttggc ccaatgctca gcgtgattct gaggaaaggg    480
tattggtgac tgaatgcggc ggtggtgaca gtatcttctg caaaacactc accattccca    540
gggtggttgg aaatgatact ggagcctaca agtgctcgta ccgggacgtc gacatagcct    600
ccactgttta tgtctatgtt cgagattaca gatcaccatt catcgcctct gtcagtgacc    660
agcatggcat cgtgtacatc accgagaaca gaacaaaac tgtggtgatc ccctgccgag    720
ggtcgatttc aaacctcaat gtgtctcttt gcgctaggta tccagaaaag agatttgttc    780
cggatggaaa cagaatttcc tgggacagcg agataggctt tactctcccc agttacatga    840
tcagctatgc cggcatggtc ttctgtgagg caaagatcaa tgatgaaacc tatcagtcta    900
tcatgtacat agttgtggtt gtaggatata ggatttatga tgtgattctg agccccccgc    960
atgaaattga gctatctgcc ggagaaaaac ttgtcttaaa ttgtacagcg agaacagagc   1020
tcaatgtggg gcttgatttc acctggcact ctccaccttc aaagtctcat cataagaaga   1080
ttgtaaaccg ggatgtgaaa ccctttcctg ggactgtggc gaagatgttt ttgagcacct   1140
tgacaataga aagtgtgacc aagagtgacc aaggggaata cacctgtgta gcgtccagtg   1200
gacggatgat caagagaaat agaacatttg tccgagttca cacaaagcct tttattgctt   1260
tcggtagtgg gatgaaatct ttggtggaag ccacagtggg cagtcaagtc cgaatccctg   1320
tgaagtatct cagttaccca gctcctgata tcaaatggta cagaaatgga aggcccattg   1380
agtccaacta cacaatgatt gttggcgatg aactccaccat catggaagtg actgaaagag   1440
atgcaggaaa ctacacggtc atcctcacca accccatttc aatggagaaa cagagccaca   1500
tggtctctct ggttgtgaat gtcccacccc agatcggtga aaagccttg atctcgccta   1560
tggattccta ccagtatggg accatgcaga cattgacatg cacagtctac gccaaccctc   1620
ccctgcacca catccagtgg tactggcagc tagaagaagc ctgctcctac agacccggcc   1680
aaacaagccc gtatgcttgt aaagaatgga cacgtggga ggatttccag gggggaaaca   1740
agatcgaagt caccaaaaac caatatgccc tgattgaagg aaaaaacaaa actgtaagta   1800
cgctggtcat ccaagctgcc aacgtgtcag cgttgtacaa atgtgaagcc atcaacaaag   1860
cgggacgagg agagagggtc atctccttcc atgtgatcag gggtcctgaa attactgtgc   1920
aacctgctgc ccagccaact gagcaggaga gtgtgtccct gttgtgcact gcagacagaa   1980
atacgtttga gaacctcacg tggtacaagc ttggctcaca ggcaacatcg gtccacatgg   2040
gcgaatcact cacaccagtt tgcaagaact tggatgctct ttggaaactg aatggcacca   2100
tgtttcctaa cagcacaaat gacatcttga ttgtggcatt tcagaatgcc tctctgcagg   2160
accaaggcga ctatgtttgc tctgctcaag ataagaagac caagaaaaga cattgcctgg   2220
tcaaacagct catcatccta ggtatggagg catccctggg tgacagaatt gcaatgcctt   2280
aaatgcagtg tgtttgagtg ttgtagtagg ctggcacact cctggaagca gagcaaagct   2340
```

| | |
|---|---|
| aacagtggtg aggtaagaca ttaaaattag aagacagctt gactcttcct agcctttaag | 2400 |
| atgatgtcac tactagtatg tgcaagggat tagcttaaat ccagagaact tcctgtggca | 2460 |
| tccctggaca ttcagatgat tacagttagc acatgtgtgt aatactatta gcaaagagag | 2520 |
| ggtcagaagc tcaaagtgat gacccagaag gagagggtga gactataggc aaataccggg | 2580 |
| tggtcgtgcc attgtggtgt ctccaactcc tggggataaa aattgatctt tgcttgctta | 2640 |
| ctgccgtaat tttagtcaga gaacacactg gcacatacaa ggtggtcaat gggatacctg | 2700 |
| cttcatgaaa agtgtgatga gggtctgaat ttaagatcta gaagattcca cggaagggt | 2760 |
| gccacactca ttgcctgtac tcctctggta gcctatgtgg tctgcagtag gtgaagttca | 2820 |
| gtgagataag tttgggatta gaaaaaaaaa actttcacat ttcctgtggg gatgctagcc | 2880 |
| tgtcttgtct aaccttgtac tttgcacaaa acctaggcaa tctctgctct gaggatatct | 2940 |
| ggtgagttta ggaggcatct ctgtgctttt ttcctgccat tttctccttt ctttgttgtg | 3000 |
| ctctctgagg ttctcgtgat gtgcatcttc tctggtttat agtgtgagaa aggtgaactg | 3060 |
| cccaggctaa ctaatctaca tcaacatttt acatgaatat cattttaag tgctttggct | 3120 |
| tatctgaggg ggtgtttgaa aatagatgct aacatatgat tgttattaaa aagaaacttg | 3180 |
| gggacagaag gacagatgtt tctgagtgaa gttgttccca agaccctaga gatcaccaca | 3240 |
| cacataggac ccgttatatc aggttaacag tagctgatcc agatgagggc aagtttagaa | 3300 |
| gggagctctg gcttagcca tgaccaggaa gtttcctatc acagtcagtg gtatgcttc | 3360 |
| tataaggatg cctctgttgt ttccaaaact ctgttcttgg aagtaggcca gagccaagta | 3420 |
| cacttgttta aactctgata tatatagtac atggtggaaa tgaccacgtt ctgctaagtg | 3480 |
| tggaagagat tctctcaaca tgattcttcc tgatgctcat caatgtttct actgcagttg | 3540 |
| ggtgattttc aggagcacgg taagctcag gctttgctgt ccatgtagac aaatggcctt | 3600 |
| ggcttttcgt aggatattat tgtttggttt gtgtttgagt ggaaaccacg aaggagtttt | 3660 |
| aggcccatca gactctacta ttatctcaac catttactta gttataggt aaggtgctta | 3720 |
| acctggactg caatcacatc acataaaaat aaggctaatg gcgtggctct cattatatgt | 3780 |
| gactgacagt aaatattaga aatgatatag ttatccaaag ttatgtaagt cactccttac | 3840 |
| ataattgtcc tgaagtttg tctttcctaa gggaaaacat gaattttact cttagaggct | 3900 |
| acaactttcc agagaagaag ttactcttag ggaaagcctt gtggaattgg agggaaataa | 3960 |
| atcctctaac ctgaataaaa ccatccccaa agaaaaaaaa aaaaaaaaa aaaaaaaaa | 4020 |
| aaaaa | 4025 |

<210> SEQ ID NO 2
<211> LENGTH: 2022
<212> TYPE: DNA
<213> ORGANISM: Mus sp.

<400> SEQUENCE: 2

| | |
|---|---|
| atggagagca aggcgctgct agctgtcgct ctgtggttct gcgtggagac ccgagccgcc | 60 |
| tctgtgggtt tgcctggcga ttttctccat ccccccaagc tcagcacaca gaaagacata | 120 |
| ctgacaattt tggcaaatac aacccttcag attacttgca ggggacagcg ggacctggac | 180 |
| tggctttggc ccaatgctca gcgtgattct gaggaaaggg tattggtgac tgaatgcggc | 240 |
| ggtggtgaca gtatcttctg caaaacactg accattccca gggtggttgg aaatgatact | 300 |
| ggagcctaca gtgctcgta ccgggacgtc gacatagcct ccactgtta tgtctatgtt | 360 |
| cgagattaca gatcaccatt catcgcctct gtcagtgacc agcatggcat cgtgtacatc | 420 |

| | | | |
|---|---|---|---|
| accgagaaca agaacaaaac tgtggtgatc ccctgccgag ggtcgatttc aaacctcaat | 480 |
| gtgtctcttt gcgctaggta tccagaaaag agatttgttc cggatggaaa cagaatttcc | 540 |
| tgggacagcg agataggctt tactctcccc agttacatga tcagctatgc cggcatggtc | 600 |
| ttctgtgagg caaagatcaa tgatgaaacc tatcagtcta tcatgtacat agttgtggtt | 660 |
| gtaggatata ggatttatga tgtgattctg agccccccgc atgaaattga gctatctgcc | 720 |
| ggagaaaaac ttgtcttaaa ttgtacagcg agaacagagc tcaatgtggg gcttgatttc | 780 |
| acctggcact ctccaccttc aaagtctcat cataagaaga ttgtaaaccg ggatgtgaaa | 840 |
| cccttttcctg ggactgtggc gaagatgttt tgagcaccct tgacaataga agtgtgacc | 900 |
| aagagtgacc aaggggaata cacctgtgta gcgtccagtg gacggatgat caagagaaat | 960 |
| agaacatttg tccgagttca cacaaagcct tttattgctt tcggtagtgg gatgaaatct | 1020 |
| ttggtggaag ccacagtggg cagtcaagtc gaatccctg tgaagtatct cagttaccca | 1080 |
| gctcctgata tcaaatggta cagaaatgga aggcccattg agtccaacta cacaatgatt | 1140 |
| gttggcgatg aactcaccat catggaagtg actgaaagag atgcaggaaa ctacacggtc | 1200 |
| atcctcacca ccccatttc aatggagaaa cagagccaca tggtctctct ggttgtgaat | 1260 |
| gtcccacccc agatcggtga gaaagccttg atctcgccta tggattccta ccagtatggg | 1320 |
| accatgcaga cattgacatg cacagtctac gccaaccctc ccctgcacca catccagtgg | 1380 |
| tactggcagc tagaagaagc ctgctcctac agacccggcc aaacaagccc gtatgcttgt | 1440 |
| aaagaatgga gacacgtgga ggatttccag gggggaaaca agatcgaagt caccaaaaac | 1500 |
| caatatgccc tgattgaagg aaaaaacaaa actgtaagta cgctggtcat ccaagctgcc | 1560 |
| aacgtgtcag cgttgtacaa atgtgaagcc atcaacaaag cgggacgagg agagagggtc | 1620 |
| atctccttcc atgtgatcag gggtcctgaa attactgtgc aacctgctgc ccagccaact | 1680 |
| gagcaggaga gtgtgtccct gttgtgcact gcagacagaa atacgtttga gaaccctcacg | 1740 |
| tggtacaagc ttggctcaca ggcaacatcg gtccacatgg gcgaatcact cacaccagtt | 1800 |
| tgcaagaact tggatgctct ttggaaactg aatggcacca tgttttctaa cagcacaaat | 1860 |
| gacatcttga ttgtggcatt tcagaatgcc tctctgcagg accaaggcga ctatgtttgc | 1920 |
| tctgctcaag ataagaagac caagaaaaga cattgcctgg tcaaacagct catcatccta | 1980 |
| ggtatggagg catccctggg tgacagaatt gcaatgcctt aa | 2022 |

<210> SEQ ID NO 3
<211> LENGTH: 673
<212> TYPE: PRT
<213> ORGANISM: Mus sp.

<400> SEQUENCE: 3

Met Glu Ser Lys Ala Leu Leu Ala Val Ala Leu Trp Phe Cys Val Glu
1               5                   10                  15

Thr Arg Ala Ala Ser Val Gly Leu Pro Gly Asp Phe Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
    50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val

```
                        85                  90                  95
Gly Asn Asp Thr Gly Ala Tyr Lys Cys Ser Tyr Arg Asp Val Asp Ile
                    100                 105                 110

Ala Ser Thr Val Tyr Val Tyr Val Arg Asp Tyr Arg Ser Pro Phe Ile
                    115                 120                 125

Ala Ser Val Ser Asp Gln His Gly Ile Val Tyr Ile Thr Glu Asn Lys
                    130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                    165                 170                 175

Asn Arg Ile Ser Trp Asp Ser Glu Ile Gly Phe Thr Leu Pro Ser Tyr
                    180                 185                 190

Met Ile Ser Tyr Ala Gly Met Val Phe Cys Glu Ala Lys Ile Asn Asp
                    195                 200                 205

Glu Thr Tyr Gln Ser Ile Met Tyr Ile Val Val Val Gly Tyr Arg
                    210                 215                 220

Ile Tyr Asp Val Ile Leu Ser Pro Pro His Glu Ile Glu Leu Ser Ala
225                 230                 235                 240

Gly Glu Lys Leu Val Leu Asn Cys Thr Ala Arg Thr Glu Leu Asn Val
                    245                 250                 255

Gly Leu Asp Phe Thr Trp His Ser Pro Pro Ser Lys Ser His His Lys
                    260                 265                 270

Lys Ile Val Asn Arg Asp Val Lys Pro Phe Pro Gly Thr Val Ala Lys
                    275                 280                 285

Met Phe Leu Ser Thr Leu Thr Ile Glu Ser Val Thr Lys Ser Asp Gln
                    290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
                    325                 330                 335

Gly Met Lys Ser Leu Val Glu Ala Thr Val Gly Ser Gln Val Arg Ile
                    340                 345                 350

Pro Val Lys Tyr Leu Ser Tyr Pro Ala Pro Asp Ile Lys Trp Tyr Arg
                    355                 360                 365

Asn Gly Arg Pro Ile Glu Ser Asn Tyr Thr Met Ile Val Gly Asp Glu
                    370                 375                 380

Leu Thr Ile Met Glu Val Thr Glu Arg Asp Ala Gly Asn Tyr Thr Val
385                 390                 395                 400

Ile Leu Thr Asn Pro Ile Ser Met Glu Lys Gln Ser His Met Val Ser
                    405                 410                 415

Leu Val Val Asn Val Pro Pro Gln Ile Gly Glu Lys Ala Leu Ile Ser
                    420                 425                 430

Pro Met Asp Ser Tyr Gln Tyr Gly Thr Met Gln Thr Leu Thr Cys Thr
                    435                 440                 445

Val Tyr Ala Asn Pro Pro Leu His His Ile Gln Trp Tyr Trp Gln Leu
                    450                 455                 460

Glu Glu Ala Cys Ser Tyr Arg Pro Gly Gln Thr Ser Pro Tyr Ala Cys
465                 470                 475                 480

Lys Glu Trp Arg His Val Glu Asp Phe Gln Gly Gly Asn Lys Ile Glu
                    485                 490                 495

Val Thr Lys Asn Gln Tyr Ala Leu Ile Glu Gly Lys Asn Lys Thr Val
                    500                 505                 510
```

```
Ser Thr Leu Val Ile Gln Ala Ala Asn Val Ser Ala Leu Tyr Lys Cys
        515                 520                 525

Glu Ala Ile Asn Lys Ala Gly Arg Gly Glu Arg Val Ile Ser Phe His
    530                 535                 540

Val Ile Arg Gly Pro Glu Ile Thr Val Gln Pro Ala Ala Gln Pro Thr
545                 550                 555                 560

Glu Gln Glu Ser Val Ser Leu Leu Cys Thr Ala Asp Arg Asn Thr Phe
                565                 570                 575

Glu Asn Leu Thr Trp Tyr Lys Leu Gly Ser Gln Ala Thr Ser Val His
            580                 585                 590

Met Gly Glu Ser Leu Thr Pro Val Cys Lys Asn Leu Asp Ala Leu Trp
        595                 600                 605

Lys Leu Asn Gly Thr Met Phe Ser Asn Ser Thr Asn Asp Ile Leu Ile
    610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
                645                 650                 655

Leu Ile Ile Leu Gly Met Glu Ala Ser Leu Gly Asp Arg Ile Ala Met
            660                 665                 670

Pro
```

<210> SEQ ID NO 4
<211> LENGTH: 2037
<212> TYPE: DNA
<213> ORGANISM: Homo sapiens

<400> SEQUENCE: 4

```
atgcagagca aggtgctgct ggccgtcgcc ctgtggctct gcgtggagac ccgggccgcc     60
tctgtgggtt tgcctagtgt ttctcttgat ctgcccaggc tcagcataca aaaagacata    120
cttacaatta aggctaatac aactcttcaa attacttgca ggggacagag ggacttggac    180
tggcttggc ccaataatca gagtggcagt gagcaaaggg tggaggtgac tgagtgcagc    240
gatggcctct tctgtaagac actcacaatt ccaaaagtga tcggaaatga cactggagcc    300
tacaagtgct tctaccggga aactgacttg gcctcggtca tttatgtcta tgttcaagat    360
tacagatctc catttattgc ttctgttagt gaccaacatg gagtcgtgta cattactgag    420
aacaaaaaca aaactgtggt gattccatgt ctcgggtcca tttcaaatct caacgtgtca    480
ctttgtgcaa gatacccaga aaagagattt gttcctgatg gtaacagaat tcctgggac    540
agcaagaagg gcttttactat tcccagctac atgatcagct atgctggcat ggtcttctgt    600
gaagcaaaaa ttaatgatga agttaccag tctattatgt acatagttgt cgttgtaggg    660
tataggattt atgatgtggt tctgagtccg tctcatggaa ttgaactatc tgttggagaa    720
aagcttgtct taaattgtac agcaagaact gaactaaatg tggggattga cttcaactgg    780
gaatacccctt cttcgaagca tcagcataag aaacttgtaa accgagacct aaaaacccag    840
tctgggagtg agatgaagaa atttttgagc accttaacta tagatggtgt aacccggagt    900
gaccaaggat tgtacacctg tgcagcatcc agtgggctga tgaccaagaa gaacagcaca    960
tttgtcaggg tccatgaaaa accttttgtt gcttttggaa gtggcatgga atctctggtg   1020
gaagccacgg tggggagcg tgtcagaatc cctgcgaagt accttggtta ccccaccccca   1080
gaaataaaat ggtataaaaa tggaatacc cttgagtcca tcacacaat taagcgggg    1140
```

-continued

```
catgtactga cgattatgga agtgagtgaa agagacacag gaaattacac tgtcatcctt    1200
accaatccca tttcaaagga gaagcagagc catgtggtct ctctggttgt gtatgtccca    1260
ccccagattg gtgagaaatc tctaatctct cctgtggatt cctaccagta cggcaccact    1320
caaacgctga catgtacggt ctatgccatt cctcccccgc atcacatcca ctggtattgg    1380
cagttggagg aagagtgcgc caacgagccc agccaagctg tctcagtgac aaacccatac    1440
ccttgtgaag aatggagaag tgtggaggac ttccagggag gaaataaaat tgaagttaat    1500
aaaaatcaat ttgctctaat tgaaggaaaa aacaaaactg taagtaccct tgttatccaa    1560
gcggcaaatg tgtcagcttt gtacaaatgt gaagcggtca acaaagtcgg agaggagag     1620 agggtgatct ccttccacgt gaccaggggt cctgaaatta ctttgcaacc tgacatgcag    1680
cccactgagc aggagagcgt gtctttgtgg tgcactgcag acagatctac gtttgagaac    1740
ctcacatggt acaagcttgg cccacagcct ctgccaatcc atgtgggaga gttgcccaca    1800
cctgtttgca agaacttgga tactctttgg aaattgaatg ccaccatgtt ctctaatagc    1860
acaaatgaca ttttgatcat ggagcttaag aatgcatcct tgcaggacca aggagactat    1920
gtctgccttg ctcaagacag gaagaccaag aaaagacatt gcgtggtcag gcagctcaca    1980
gtcctaggta gggagacaat tctggatcat tgtgcagagg cagttggaat gccttaa       2037
```

```
<210> SEQ ID NO 5
<211> LENGTH: 678
<212> TYPE: PRT
<213> ORGANISM: Homo sapiens

<400> SEQUENCE: 5

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220
```

```
Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640
```

```
Val Cys Leu Ala Gln Asp Arg Lys Thr Lys Lys Arg His Cys Val Val
            645                 650                 655

Arg Gln Leu Thr Val Leu Gly Arg Glu Thr Ile Leu Asp His Cys Ala
        660                 665                 670

Glu Ala Val Gly Met Pro
        675

<210> SEQ ID NO 6
<211> LENGTH: 2037
<212> TYPE: DNA
<213> ORGANISM: Macaca mulatta

<400> SEQUENCE: 6
atggcgagca aggtgctgct ggccgtcgcc ctgtggctct gcgtggagac ccgggccgcc      60
tctgtgggtt tgcctagtgt ttctcttgat ctgcccaggc tcagcataca aaaagacata     120
cttacaatta aggctaatac aactcttcaa attacttgca ggggacagag ggacttggac     180
tggctttggc ccaataatca gagtggcagt gagcaagggt ggaggtgac tgagtgcagc      240
gatggcctct tctgtaagac actcacaatt ccaaaagtga tcggaaatga cactggagcc     300
tacaagtgct ctaccggga aactgacttg gcctcggtca tttatgtcta tgttcaagat     360
tacagatctc catttattgc ttctgttagt gaccaacatg gagtcgtgta cattactgag     420
aacaaaaaca aaactgtggt gattccatgt ctcgggtcca tttcaaatct caacgtgtca     480
ctttgtgcaa ggtacccaga aaagagattt gttcctgatg taacagaat tcctgggac      540
agcaagaagg gctttactat tcccagctat atgatcagct atgctggcat ggtcttctgt     600
gaagcaaaaa ttaatgatga agttaccag tctattatgt acatagttgt ggttgtaggg     660
tataggattt atgatgtggt tctgagtccg tctcatggag ttgaactatc tgttggagag     720
aagcttgtct taaattgtac agcaagaact gaactaaatg tggggattga cttcaactgg     780
gaataccctt cttcgaagca tcagcataag aaacttgtaa accgagatct aaaaacccag     840
tctgggagtg agatgaagaa atttttgagc accttaacta tagatggtgt aacccggagt     900
gaccaaggat tgtacacctg tgcagcgtcc agtgggctga tgaccaagaa gaacagcaca     960
tttgtcaggg tccatgaaaa accttttgtt gcttttggaa gtggcatgga atctctggtg    1020
gaagccacgg tggggagcg tgtcagaatc cctgtgaagt accttggtta cccgccccca    1080
gaaataaaat ggtataaaaa tggaataccc cttgagtcca atcacacagt taaagtgggg    1140
catgtgctga cgatcatgga agtgagcgaa agagacacag gaaattacac tgtcatcctt    1200
accaatccca tttcaaagga gaagcagagt cacgtggtct ctctggttgt gtatgtccca    1260
ccccagattg gtgagaaatc tctgatctct cctgtggatt cctaccagta cggcaccact    1320
caaacgctga catgtacggt ctacgctatt cctccccccgc atcacatcca ctggtattgg    1380
cagttggagg aagagtgccc caacgagccc agccaagctg tctcagtgac aaacccatac    1440
ccttgtgaag aatggagaag tgtggaggac ttccagggag aaataaaat tgaagtcaat    1500
aaaaatcaat ttgctctaat tgaaggaaaa aacaaaactg taagtaccct tgttatccaa    1560
gcggcaaatg tgtcagcttt gtacaaatgt gaagcggtca acaaagtcgg gagaggagag    1620
agggtgatct ccttccatgt taccaggggt cctgaaatta ctttgcaacc tgacttgcag    1680
cccactgaac aggagagcgt gtctttgtgg tgcactgcag acaaatctac atttgagaac    1740
ctcacatggt acaagcttgg cccacagcct ctgccagtcc acgtgggaga gttgcccaca    1800
cctgtttgca agaacttgga tactctttgg aaattgaatg ccactatatt ctctaatagc    1860
```

```
acaaatgaca ttttgatcat ggagcttaag aatgcatcct tgcaggacca aggagactat    1920
gtctgcgttg ctcaagacag gaagaccaag aaaagacatt gcgtggtcag gcagctcaca    1980
gtcctcggta gggagacaat tctggatcat tgtgtagggg cagttggaat gccttaa       2037

<210> SEQ ID NO 7
<211> LENGTH: 678
<212> TYPE: PRT
<213> ORGANISM: Macaca mulatta

<400> SEQUENCE: 7

Met Ala Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Val Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Val
            340                 345                 350
```

Lys Tyr Leu Gly Tyr Pro Pro Glu Ile Lys Trp Tyr Lys Asn Gly
            355                 360                 365

Ile Pro Leu Glu Ser Asn His Thr Val Lys Val Gly His Val Leu Thr
        370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
                435                 440                 445

Ala Ile Pro Pro Pro His His Ile His Trp Tyr Trp Gln Leu Glu Glu
            450                 455                 460

Glu Cys Pro Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Leu Gln
545                 550                 555                 560

Pro Thr Glu Gln Glu Ser Val Ser Leu Trp Cys Thr Ala Asp Lys Ser
                565                 570                 575

Thr Phe Glu Asn Leu Thr Trp Tyr Lys Leu Gly Pro Gln Pro Leu Pro
            580                 585                 590

Val His Val Gly Glu Leu Pro Thr Pro Val Cys Lys Asn Leu Asp Thr
        595                 600                 605

Leu Trp Lys Leu Asn Ala Thr Ile Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Val Ala Gln Asp Arg Lys Thr Lys Lys Arg His Cys Val Val
                645                 650                 655

Arg Gln Leu Thr Val Leu Gly Arg Glu Thr Ile Leu Asp His Cys Val
            660                 665                 670

Gly Ala Val Gly Met Pro
        675

<210> SEQ ID NO 8
<211> LENGTH: 2016
<212> TYPE: DNA
<213> ORGANISM: Rattus norvegicus

<400> SEQUENCE: 8
atggagagca gggcgctgct agctgtcgct ctgtggttct gcgtggagac ccgagccgcc      60
tctgtgggtt tgcctggcga ttccctccat ccacccaagc tcagcacaca aaaagacata     120
cttacaattt tggcaaatac aacccttcag attacttgca ggggacagag ggacctggat     180
tggctttggc ccaacactcc gcgtgactct gaggaaaggg tgttggtgac tgagtgtggc     240

-continued

```
gacagtatct tctgcaagac actcacagtt cccagagtgg ttggaaatga tactggagcc      300
tacaagtgct tctatcggga caccgatgtc tcctccatcg tttatgtcta tgttcaagat      360
cacaggtcac cattcatcgc ctctgtcagt gacgagcatg gcatcgtgta catcactgag      420
aacaagaaca aaactgtggt gatcccatgc cgagggtcga tttcaaacct caacgtgtca      480
ctttgtgcta ggtatccaga aaagagattt gttccggatg aaacagaatt tcctgggac      540
agcgagaaag gctttactat ccccagttac atgatcagct atgccggcat ggtcttctgt      600
gaggcaaaga ttaatgatga acgtatcag tctatcatgt acatagttct ggttgtagga      660
tataggattt atgatgtggt cctgagcccc cctcatgaaa ttgagctatc tgccggagaa      720
aagcttgtct taaattgtac agcaagaaca gagctcaacg tggggcttga tttcagctgg      780
caattcccgt cctcaaagca tcagcataag aagattgtaa accgggatgt gaatcccctt      840
cctgggactg tggcaaagat gttttttgagc accttgacca tagacagtgt gaccaagagt      900
gaccaaggag aatacacctg cacagcgtac agtggactga tgaccaagaa aaataaaaca      960
tttgtccgag ttcatacaaa acctttttatt gcttttggta gcgggatgaa atctttggtg     1020
gaagccactg tgggcagcca agtccgaatc cctgtgaagt atctcagtta cccagctcct     1080
gatatcaaat ggtacagaaa tggacgaccc attgagtcca attacacaat gatcgttggt     1140
gatgaactca ccatcatgga agtgagtgaa agagatgcgg aaactacac ggtcatcctc      1200
accaatccca tttcaatgga gaaacagagc cacatggtct ctctggttgt gaatgttcca     1260
ccccagatcg gtgagaaagc cttgatctct cctatggatt cctaccagta tggcaccatg     1320
cagacgctga catgcacagt ctatgccaac cctcccctgc accacatcca atggtactgg     1380
cagctagaag aagcatgctc ctacaggccc agccaaacaa acccatatac ttgtaaagaa     1440
tggagacacg tgaaggattt ccagggggga aataagatcg aagtcaccaa aaaccaatat     1500
gccctaattg aaggaaaaaa caaaactgta agtactctgg tcatccaggc tgcctacgtg     1560
tccgcattat acaaatgtga agccatcaac aaagcaggac gaggagagag ggtcatctcc     1620
ttccatgtga tcagggggtcc tgaaattact gtccagcctg ctacccagcc aaccgagcgg     1680
gagagtatgt ctttattgtg cactgcagat agaaacacgt tgagaacct cacgtggtac      1740
aagcttggct cacaggcaac atcggtccac atgggcgaat cactcacacc agtttgcaag     1800
aacttggacg ctcttttggaa actgaatggc accgtgtttt ctaacagcac aaacgacatc     1860
ttgattgtgg cattccagaa tgcctccctg caggaccaag gcaactatgt ctgctctgct     1920
caagacaaga agaccaagaa aagacattgc ctagtcaagc agctcgtcat cctaggtatg     1980
gagggacccc tggttgatgg ggttgcaatg ccttaa                                2016
```

<210> SEQ ID NO 9
<211> LENGTH: 671
<212> TYPE: PRT
<213> ORGANISM: Rattus norvegicus

<400> SEQUENCE: 9

```
Met Glu Ser Arg Ala Leu Leu Ala Val Ala Leu Trp Phe Cys Val Glu
1               5                   10                  15

Thr Arg Ala Ala Ser Val Gly Leu Pro Gly Asp Ser Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
```

-continued

```
            50                  55                  60
Asn Thr Pro Arg Asp Ser Glu Glu Arg Val Leu Val Thr Glu Cys Gly
 65                  70                  75                  80

Asp Ser Ile Phe Cys Lys Thr Leu Thr Val Pro Arg Val Val Gly Asn
                     85                  90                  95

Asp Thr Gly Ala Tyr Lys Cys Phe Tyr Arg Asp Thr Asp Val Ser Ser
                100                 105                 110

Ile Val Tyr Val Tyr Val Gln Asp His Arg Ser Pro Phe Ile Ala Ser
                115                 120                 125

Val Ser Asp Glu His Gly Ile Val Tyr Ile Thr Glu Asn Lys Asn Lys
130                 135                 140

Thr Val Val Ile Pro Cys Arg Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Glu Lys Gly Phe Thr Ile Pro Ser Tyr Met Ile
                180                 185                 190

Ser Tyr Ala Gly Met Val Phe Cys Glu Ala Lys Ile Asn Asp Glu Thr
                195                 200                 205

Tyr Gln Ser Ile Met Tyr Ile Val Leu Val Val Gly Tyr Arg Ile Tyr
210                 215                 220

Asp Val Val Leu Ser Pro Pro His Glu Ile Glu Leu Ser Ala Gly Glu
225                 230                 235                 240

Lys Leu Val Leu Asn Cys Thr Ala Arg Thr Glu Leu Asn Val Gly Leu
                245                 250                 255

Asp Phe Ser Trp Gln Phe Pro Ser Ser Lys His Gln His Lys Lys Ile
                260                 265                 270

Val Asn Arg Asp Val Lys Ser Leu Pro Gly Thr Val Ala Lys Met Phe
                275                 280                 285

Leu Ser Thr Leu Thr Ile Asp Ser Val Thr Lys Ser Asp Gln Gly Glu
290                 295                 300

Tyr Thr Cys Thr Ala Tyr Ser Gly Leu Met Thr Lys Lys Asn Lys Thr
305                 310                 315                 320

Phe Val Arg Val His Thr Lys Pro Phe Ile Ala Phe Gly Ser Gly Met
                325                 330                 335

Lys Ser Leu Val Glu Ala Thr Val Gly Ser Gln Val Arg Ile Pro Val
                340                 345                 350

Lys Tyr Leu Ser Tyr Pro Ala Pro Asp Ile Lys Trp Tyr Arg Asn Gly
                355                 360                 365

Arg Pro Ile Glu Ser Asn Tyr Thr Met Ile Val Gly Asp Glu Leu Thr
                370                 375                 380

Ile Met Glu Val Ser Glu Arg Asp Ala Gly Asn Tyr Thr Val Ile Leu
385                 390                 395                 400

Thr Asn Pro Ile Ser Met Glu Lys Gln Ser His Met Val Ser Leu Val
                405                 410                 415

Val Asn Val Pro Pro Gln Ile Gly Glu Lys Ala Leu Ile Ser Pro Met
                420                 425                 430

Asp Ser Tyr Gln Tyr Gly Thr Met Gln Thr Leu Thr Cys Thr Val Tyr
                435                 440                 445

Ala Asn Pro Pro Leu His His Ile Gln Trp Tyr Trp Gln Leu Glu Glu
                450                 455                 460

Ala Cys Ser Tyr Arg Pro Ser Gln Thr Asn Pro Tyr Thr Cys Lys Glu
465                 470                 475                 480
```

```
Trp Arg His Val Lys Asp Phe Gln Gly Gly Asn Lys Ile Glu Val Thr
            485                 490                 495
Lys Asn Gln Tyr Ala Leu Ile Glu Gly Lys Asn Lys Thr Val Ser Thr
        500                 505                 510
Leu Val Ile Gln Ala Ala Tyr Val Ser Ala Leu Tyr Lys Cys Glu Ala
    515                 520                 525
Ile Asn Lys Ala Gly Arg Gly Glu Arg Val Ile Ser Phe His Val Ile
530                 535                 540
Arg Gly Pro Glu Ile Thr Val Gln Pro Ala Thr Gln Pro Thr Glu Arg
545                 550                 555                 560
Glu Ser Met Ser Leu Leu Cys Thr Ala Asp Arg Asn Thr Phe Glu Asn
            565                 570                 575
Leu Thr Trp Tyr Lys Leu Gly Ser Gln Ala Thr Ser Val His Met Gly
        580                 585                 590
Glu Ser Leu Thr Pro Val Cys Lys Asn Leu Asp Ala Leu Trp Lys Leu
    595                 600                 605
Asn Gly Thr Val Phe Ser Asn Ser Thr Asn Asp Ile Leu Ile Val Ala
610                 615                 620
Phe Gln Asn Ala Ser Leu Gln Asp Gln Gly Asn Tyr Val Cys Ser Ala
625                 630                 635                 640
Gln Asp Lys Lys Thr Lys Lys Arg His Cys Leu Val Lys Gln Leu Val
            645                 650                 655
Ile Leu Gly Met Glu Gly Pro Leu Val Asp Gly Val Ala Met Pro
        660                 665                 670

<210> SEQ ID NO 10
<211> LENGTH: 2040
<212> TYPE: DNA
<213> ORGANISM: Bos taurus

<400> SEQUENCE: 10
atggagagca aggcgctgct ggcccttgct ctgtggctct gcgtggagac ccgggctgcc        60
tctgtgggtt tttctagtgt ttcccttgat cccccaggc tcagcatcca aaaagacata       120
cttagagtta tggctaacac aacgcttcag attacttgca ggggtcagag ggacttgcag       180
tggctctggc ccaacaatca gagcagctct gagaaaagag tggaggtcac agactgcagt       240
gatgcgtctc tctgtaagat gctcacaatt tcagaagtga ttggaaatga actggagcc       300 tacaagtgct ctctaccagga cactgacatg ggctccgttc tttatgtgta tgttcaagat       360
tacaggtctc cgtttattgc ttctgttagc gaccagcatg aagttgtgta catcactgag       420
aacaaaaaca aaactgtggt gattccgtgt ttggggactg tttcagacct caatgtgtca       480
ctctgtgcaa ggtatccaga aaaagattt gtacctgatg gtaacagaat tcctgggac        540 agccagaaag gcttcagtat tcccagctat atgatcagtt atgctggcgt ggtcttctgc       600
gaagcaaaaa tcaatgatga agttaccag tctattatgt acataattgt ggttataggg       660
tacaagattt atgatgtggt tctgagcccc cctcacggag tcgagctgtc tgttggagag       720
aagctcatct taaactgtac ggcaagaact gagctaaatg tggggatcga cttccactgg       780 gaatacccctt ctttgaagca tcagcataaa aaacttataa accggaccct aaaaacccag       840
tctgggactg aaatgaagaa gttttttgagc accttgacta tagatggtgt aacccggagt       900
gaccaggggt ggtatatctg tgcagcttcc agtgggctga tgaccaagaa gaacagcacg       960
tttgtccggg tacatgaaaa gcctttttgtt gctttcggta gtggcatgga atccttggtg      1020
```

```
gaagccaccg tgggggaacg tgtgagagtc cctgtcaagt accttggtta ccctcctcca    1080
gaaataaaat ggtataaaaa tggaagaccc attgagtcca atcacacagt aaagtgggga    1140
catgtgctga ctattatgga agtgagtgag aaagatacag gaaattacac tgtcattctt    1200
accaatccca tttcaaagga gaaacagagc cacatggtat ctctggtggt gaatgtccca    1260
cctcagattg gtgagaaatc tctgctgtct cccgtggact cttaccagta cggcacttcc    1320
caaacgctga cgtgcacggt ctacgccgtt cctcccccaa gtcacattcg ctggtactgg    1380
cagctggaga cggagtgcac ctaccagccc accctcactg ccttaacgac aaacccatac    1440
acttgtaagg aatggagaaa cgtggaggac ttccaggggg gaaacaaaat cgaagtcaac    1500
aaaaatcaga ttgccctaat tgaaggaaga acaaaactg taagtactct tgttatccaa    1560
gcggccaatg tgtctgcttt gtataaatgt gaagcagtga acaaagctgg aagaggagag    1620
agggttatct ccttccatgt gaccagggggt cctgaaatca cactgcaacc tggcatccag    1680
cccaccgagc aggagaatgt gtctctgtgg tgctctgcgg acagaactat gtttgagaac    1740
ctcacgtggt acaaactcgg cccacaggcc ctgcccatcc acatgggcga tttacccaca    1800
cctgtctgca gaacttgga tgctctttgg aaaatgaatg ccaccatgaa ctctaacggc    1860
acaaatgaca tcttgatctt ggagctgcag aatgcatcct tgcaggacca aggagactat    1920
gtctgctttg ctcaggacag gaagactaag aaaagacatt gtgtggccag gcagctcaca    1980
gtcctaggta gggcagtcac tctggaccat ccagaggcag ttgggttgcc ttcaatgtaa    2040
```

<210> SEQ ID NO 11
<211> LENGTH: 679
<212> TYPE: PRT
<213> ORGANISM: Bos taurus

<400> SEQUENCE: 11

```
Met Glu Ser Lys Ala Leu Leu Ala Leu Ala Leu Trp Leu Cys Val Glu
1               5                   10                  15

Thr Arg Ala Ala Ser Val Gly Phe Ser Ser Val Ser Leu Asp Pro Pro
                20                  25                  30

Arg Leu Ser Ile Gln Lys Asp Ile Leu Arg Val Met Ala Asn Thr Thr
            35                  40                  45

Leu Gln Ile Thr Cys Arg Gly Gln Arg Asp Leu Gln Trp Leu Trp Pro
        50                  55                  60

Asn Asn Gln Ser Ser Ser Glu Lys Arg Val Glu Val Thr Asp Cys Ser
65                  70                  75                  80

Asp Gly Val Phe Cys Lys Met Leu Thr Ile Ser Glu Val Ile Gly Asn
                85                  90                  95

Asp Thr Gly Ala Tyr Lys Cys Phe Tyr Gln Asp Thr Asp Met Gly Ser
            100                 105                 110

Val Leu Tyr Val Tyr Val Gln Asp Tyr Arg Ser Pro Phe Ile Ala Ser
        115                 120                 125

Val Ser Asp Gln His Glu Val Val Tyr Ile Thr Glu Asn Lys Asn Lys
    130                 135                 140

Thr Val Val Ile Pro Cys Leu Gly Thr Val Ser Asp Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Gln Lys Gly Phe Ser Ile Pro Ser Tyr Met Ile
            180                 185                 190

Ser Tyr Ala Gly Val Val Phe Cys Glu Ala Lys Ile Asn Asp Glu Ser
```

```
            195                 200                 205
Tyr Gln Ser Ile Met Tyr Ile Val Val Ile Gly Tyr Lys Ile Tyr
210                 215                 220

Asp Val Val Leu Ser Pro Pro His Gly Val Glu Leu Ser Val Gly Glu
225                 230                 235                 240

Lys Leu Ile Leu Asn Cys Thr Ala Arg Thr Glu Leu Asn Val Gly Ile
                    245                 250                 255

Asp Phe His Trp Glu Tyr Pro Ser Leu Lys His Gln His Lys Lys Leu
                260                 265                 270

Ile Asn Arg Asp Leu Lys Thr Gln Ser Gly Thr Glu Met Lys Lys Phe
            275                 280                 285

Leu Ser Thr Leu Thr Ile Asp Gly Val Thr Arg Ser Asp Gln Gly Trp
290                 295                 300

Tyr Ile Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Val Pro Val
                340                 345                 350

Lys Tyr Leu Gly Tyr Pro Pro Pro Glu Ile Lys Trp Tyr Lys Asn Gly
            355                 360                 365

Arg Pro Ile Glu Ser Asn His Thr Val Lys Val Gly His Val Leu Thr
370                 375                 380

Ile Met Glu Val Ser Glu Lys Asp Thr Gly Asn Tyr Thr Val Ile Leu
385                 390                 395                 400

Thr Asn Pro Ile Ser Lys Glu Lys Gln Ser His Met Val Ser Leu Val
                405                 410                 415

Val Asn Val Pro Pro Gln Ile Gly Glu Lys Ser Leu Ser Pro Val
                420                 425                 430

Asp Ser Tyr Gln Tyr Gly Thr Ser Gln Thr Leu Thr Cys Thr Val Tyr
            435                 440                 445

Ala Val Pro Pro Pro Ser His Ile Arg Trp Tyr Trp Gln Leu Glu Thr
450                 455                 460

Glu Cys Thr Tyr Gln Pro Thr Leu Thr Ala Leu Thr Thr Asn Pro Tyr
465                 470                 475                 480

Thr Cys Lys Glu Trp Arg Asn Val Glu Asp Phe Gln Gly Gly Asn Lys
                485                 490                 495

Ile Glu Val Asn Lys Asn Gln Ile Ala Leu Ile Glu Gly Arg Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Ala Gly Arg Gly Glu Arg Val Ile Ser
530                 535                 540

Phe His Val Thr Arg Gly Pro Glu Ile Thr Leu Gln Pro Gly Ile Gln
545                 550                 555                 560

Pro Thr Glu Gln Glu Asn Val Ser Leu Trp Cys Ser Ala Asp Arg Thr
                565                 570                 575

Met Phe Glu Asn Leu Thr Trp Tyr Lys Leu Gly Pro Gln Ala Leu Pro
                580                 585                 590

Ile His Met Gly Asp Leu Pro Thr Pro Val Cys Lys Asn Leu Asp Ala
            595                 600                 605

Leu Trp Lys Met Asn Ala Thr Met Asn Ser Asn Gly Thr Asn Asp Ile
610                 615                 620
```

```
Leu Ile Leu Glu Leu Gln Asn Ala Ser Leu Gln Asp Gln Gly Asp Tyr
625                 630                 635                 640

Val Cys Phe Ala Gln Asp Arg Lys Thr Lys Arg His Cys Val Ala
            645                 650                 655

Arg Gln Leu Thr Val Leu Gly Arg Ala Val Thr Leu Asp His Pro Glu
        660                 665                 670

Ala Val Gly Leu Pro Ser Met
        675

<210> SEQ ID NO 12
<211> LENGTH: 38
<212> TYPE: DNA
<213> ORGANISM: Mus sp.

<400> SEQUENCE: 12
gtatggaggc atccctgggt gacagaattg caatgcct                              38

<210> SEQ ID NO 13
<211> LENGTH: 47
<212> TYPE: DNA
<213> ORGANISM: Homo sapiens

<400> SEQUENCE: 13
gtagggagac aattctggat cattgtgcag aggcagttgg aatgcct                    47

<210> SEQ ID NO 14
<211> LENGTH: 47
<212> TYPE: DNA
<213> ORGANISM: Macaca mulatta

<400> SEQUENCE: 14
gtagggagac aattctggat cattgtgtag gggcagttgg aatgcct                    47

<210> SEQ ID NO 15
<211> LENGTH: 38
<212> TYPE: DNA
<213> ORGANISM: Rattus norvegicus

<400> SEQUENCE: 15
gtatggaggg acccctggtt gatggggttg caatgcct                              38

<210> SEQ ID NO 16
<211> LENGTH: 50
<212> TYPE: DNA
<213> ORGANISM: Bos taurus

<400> SEQUENCE: 16
gtagggcagt cactctggac catccagagg cagttgggtt gccttcaatg                 50

<210> SEQ ID NO 17
<211> LENGTH: 13
<212> TYPE: PRT
<213> ORGANISM: Mus sp.

<400> SEQUENCE: 17

Gly Met Glu Ala Ser Leu Gly Asp Arg Ile Ala Met Pro
1               5                   10

<210> SEQ ID NO 18
<211> LENGTH: 16
<212> TYPE: PRT
<213> ORGANISM: Homo sapiens
```

-continued

<400> SEQUENCE: 18

Gly Arg Glu Thr Ile Leu Asp His Cys Ala Glu Ala Val Gly Met Pro
1               5                   10                  15

<210> SEQ ID NO 19
<211> LENGTH: 16
<212> TYPE: PRT
<213> ORGANISM: Macaca mulatta

<400> SEQUENCE: 19

Gly Arg Glu Thr Ile Leu Asp His Cys Val Gly Ala Val Gly Met Pro
1               5                   10                  15

<210> SEQ ID NO 20
<211> LENGTH: 13
<212> TYPE: PRT
<213> ORGANISM: Rattus norvegicus

<400> SEQUENCE: 20

Gly Met Glu Gly Pro Leu Val Asp Gly Val Ala Met Pro
1               5                   10

<210> SEQ ID NO 21
<211> LENGTH: 17
<212> TYPE: PRT
<213> ORGANISM: Bos taurus

<400> SEQUENCE: 21

Gly Arg Ala Val Thr Leu Asp His Pro Glu Ala Val Gly Leu Pro Ser
1               5                   10                  15

Met

<210> SEQ ID NO 22
<211> LENGTH: 21
<212> TYPE: DNA
<213> ORGANISM: Mus sp.

<400> SEQUENCE: 22
ggtatggagg catccctggg t                                        21

<210> SEQ ID NO 23
<211> LENGTH: 21
<212> TYPE: DNA
<213> ORGANISM: Mus sp.

<400> SEQUENCE: 23
cagttagcac atgtgtgtaa t                                        21

<210> SEQ ID NO 24
<211> LENGTH: 21
<212> TYPE: DNA
<213> ORGANISM: Mus sp.

<400> SEQUENCE: 24
aattgcaatg ccttaaatgc a                                        21

<210> SEQ ID NO 25
<211> LENGTH: 21
<212> TYPE: DNA
<213> ORGANISM: Mus sp.

<400> SEQUENCE: 25
ggctggcaca ctcctggaag c        21

<210> SEQ ID NO 26
<211> LENGTH: 21
<212> TYPE: DNA
<213> ORGANISM: Homo sapiens

<400> SEQUENCE: 26
taggtaggga gacaattctg g        21

<210> SEQ ID NO 27
<211> LENGTH: 21
<212> TYPE: DNA
<213> ORGANISM: Homo sapiens

<400> SEQUENCE: 27
gtagggagac aattctggat c        21

<210> SEQ ID NO 28
<211> LENGTH: 21
<212> TYPE: DNA
<213> ORGANISM: Homo sapiens

<400> SEQUENCE: 28
tcattgtgca gaggcagttg g        21

<210> SEQ ID NO 29
<211> LENGTH: 20
<212> TYPE: DNA
<213> ORGANISM: Homo sapiens

<400> SEQUENCE: 29
gaggcagttg aatgccttaa          20

<210> SEQ ID NO 30
<211> LENGTH: 21
<212> TYPE: DNA
<213> ORGANISM: Mus sp.

<400> SEQUENCE: 30
aatagatgct aacatatgat t        21

<210> SEQ ID NO 31
<211> LENGTH: 21
<212> TYPE: DNA
<213> ORGANISM: Mus sp.

<400> SEQUENCE: 31
aaactctgat atatatagta c        21

<210> SEQ ID NO 32
<211> LENGTH: 21
<212> TYPE: DNA
<213> ORGANISM: Mus sp.

<400> SEQUENCE: 32
aaatgatata gttatccaaa g        21

<210> SEQ ID NO 33
<211> LENGTH: 21
<212> TYPE: DNA
<213> ORGANISM: Mus sp.

<400> SEQUENCE: 33

-continued

```
aaatcctcta acctgaataa a                                         21

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tggagagcaa ggcgctgcta gc                                        22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ctttccactc ctgcctacct ag                                        22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aatttgggtg ccatagccaa tc                                        22

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgaggagaga gggtcatctc                                           20

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cagggatgcc tccatacc                                             18

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
```
gctctgtgcc cagcgcgagg tgcaggat                                              28

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tgctctgctt ccaggagtgt gccagcct                                              28

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aactttgtga agctcatttc ctggtat                                               27

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccttgctggg ctgggtggt                                                        19

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agagaattca ccggatccta cccgggtttt tttttttttt ttt                             43

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tggtacaagc ttggtctcac aggcaacat                                             29

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gccacactca ttgcctgtac tcctctgg                                              28

```
<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
actgcagttg ggtgattttc aggagcac                                        28

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gagaattcac cggatcctac                                                 20
```

SVEGFR-2 AND ITS ROLE IN LYMPHANGIOGENESIS MODULATION

FIELD OF THE INVENTION

The invention relates to therapeutic and diagnostic uses of soluble vascular endothelial growth factor receptor 2.

BACKGROUND OF THE INVENTION

The homeostatic mechanisms underlying the absence of vasculature (blood and lymphatic vessels) in the human and mouse cornea are remarkably intriguing given the highly vascularized nature of the neighboring tissues, such as the ocular conjunctiva. This avascular disposition makes the cornea an important angiogenesis assay platform (Gimbrone et al., J. Exp. Med., 136(2): p. 261-76, 1972) allowing scientists to study the pro- and/or anti-angiogenic effects of several compounds in vivo. More than serving as the basis for an angiogenesis assay model, the phenomenon of corneal avascularity serves essential physiological functions. Corneal neovascularization precludes optimal vision and compromises corneal immunological privilege.

In 1905, ophthalmologist Edward Zim performed the first corneal transplant in a human subject (Moffatt et al., Clin. Experiment. Opthalmol., 2005.33(6): 642-57, 2005). Since then, corneal transplants have become the most common type of solid organ transplantation in the world. Nearly 46,000 corneal transplants are performed yearly in the United States. In addition to being the most prevalent, corneal allograft transplantation is also the most successful intervention among other commonly transplanted organs. However the long-term outcome of this intervention is greatly influenced by pre-operative risk factors, with corneal neovascularization (high-risk group) being an important negative predictor of corneal allograft survival. While graft survival is approximately 90% in the low-risk group (no pre-operative inflammation or neovascularization) these numbers drastically fall to roughly 35% in the high risk group (Williams et al., Transplant. Proc., 29(1-2): 983, 1997).

While the absence of blood and lymphatic vessels in the cornea is known to play a critical role in maintaining its immune privilege (Cursiefen et al., Cornea, 22(3): 273-81, 2003), other immune-protective mechanisms have been described. One such mechanism is referred to as anterior chamber-associated immune deviation (ACAID). ACAID is regarded as the ability of antigen presenting cells and antigens from anterior chamber associated tissues (i.e., cornea) to directly enter the blood circulation through the trabecular meshwork, homing to the spleen where immune tolerance is induced (Wilbanks et al., Immunology, 71(4): 566-72, 1990; Wilbanks et al., Immunology, 71(3): 383-9, 1990; Niederkorn et al., Invest. Opthalmol. Vis. Sci., 37(13): p. 2700-7, 1996). Additionally, tissues from the anterior segment of the eye have been reported to express a protein named Fas-ligand which induces apoptosis in activated immune cells (Fas-receptor positive) (Griffith et al., Science, 270(5239): 1189-92, 1995), thus protecting the cornea from damage by activated lymphocytes. These mechanisms are thought to collectively down-regulate inflammation in the cornea therefore preserving corneal clarity which is essential for optimal vision.

Major advances in the study of corneal lymphangiogenesis have taken place since the discovery of VEGFR-3 and its ligands VEGF-C and VEGF-D (Kaipainen et al., Proc. Natl. Acad. Sci. U.S.A., 92(8): 3566-70, 1995; Joukov et al., Embo. J., 15(2): 290-98, 1996; Achen et al., Proc. Natl. Acad. Sci. U.S.A., 95(2): 548-53, 1998). The identification of specific cellular markers preferentially expressed by lymphatic endothelial cells, such as LYVE-1 (Banerji et al., J. Cell. Biol., 144(4): 789-801, 1999), Prox1 (Wigle et al., Cell, 98(6): 769-78, 1999) and podoplanin (Breiteneder-Geleff et al., Am. J. Pathol., 151(4): 1141-5212, 1997), have also propelled great advances to the field of lymphangiogenesis. The growth of lymphatic vessels into the cornea generally occurs after corneal injury and inflammation, which in turn is associated with increased levels of VEGF-C (Jiang et al., J. Huazhong Univ. Sci. Technolog. Med. Sci., 24(5): 483-5, 2004; Kure et al., Invest. Opthalmol. Vis. Sci., 44(1): 137-44, 2003). The newly formed lymphatic vessels are thought to permit an outwards route through which corneal transudate and APCs are carried from the interstitial space into the lymphatic system and later back into the blood circulation. This drainage pathway becomes extremely deleterious in the context of corneal transplantation. Under these circumstances, the alternative route bypassing the standard outflow pathway (i.e. trabecullar meshwork in the anterior chamber) allows for antigens from the donor cornea to escape through the lymphatic system and into the draining lymph node where a graft rejection reaction is initiated (Yamagami et al., Cornea, 21(4): 405-9, 2002; Liu et al., J. Exp. Med., 195(2): 259-68, 2002). By targeting corneal angiogenesis with VEGF-A binding molecules (VEGF-trap), Cursiefen et al. demonstrated that allograft survival was inversely related to the amount of neovascularization in the murine corneal transplantation model. The significance of this alternate drainage pathway to corneal alloimmunity and graft rejection has also been portrayed in a study showing that removal of cervical lymph nodes significantly increased the graft survival rates in the low and high-risk groups (Yamagami et al., Cornea, 21(4): 405-9, 2002; Yamagami et al., Invest. Opthalmol. Vis. Sci., 42(6): 1293-8, 2001).

The surgical procedures used in corneal allograft transplantation require very delicate techniques to prevent adverse inflammatory reactions which may compromise outcome. The corneal graft is initially attached to the recipient's ocular surface with the placement of small sutures. Paradoxically, in a vastly employed injury animal model of corneal angiogenesis, similar intrastromal sutures are used as a method of eliciting blood and lymphatic vessel growth (Sonoda et al., Cornea, 24(8 Suppl): S50-S54, 2005). Because suture placement is a requirement for corneal transplantation as well as a pro-angiogenic stimulus, it becomes necessary to dissect the molecular mechanisms modulating the growth of blood and lymphatic vessels under these circumstances.

Vasculogenesis relates to the embryological and/or postnatal development of vasculature from bone-marrow derived endothelial precursor cells (EPC), whereas angiogenesis is a biological process that denotes the formation of vascular tissue from pre-existing vessels (Asahara et al., Science, 275 (5302): 964-7, 1997). Functionally, angiogenesis may be subcategorized as hemangiogenesis, the growth of blood vessels; and lymphangiogenesis, which stands for the emergence of lymphatic vessels.

The VEGF family of molecules is thus far the most studied modulators of angiogenesis. This family of molecules includes VEGF, also known as VEGF-A, placental growth factor (PLGF), VEGF-B, VEGF-C, VEGF-D and VEGF-E. The pro-angiogenic effects of these growth factors are primarily mediated by binding and activation of their cognate receptors (VEGFRs). While VEGF-A is capable of binding and activating VEGFR-1 and VEGFR-2 (Ferrara et al., Nat. Med., 9(6): 669-76, 2003), VEGF-C and VEGF-D signal through VEGFR-3 and VEGFR-2 (Adams et al., Nat. Rev. Mol. Cell. Biol., 8(6): 464-78, 2007). VEGF-B and PLGF bind exclusively to VEGFR-1 and likewise, VEGF-E binding is restricted to VEGFR-2. It is important to note that VEGFR-1 and VEGFR-2 are primarily expressed in blood endothelial cells whereas VEGFR-2 and VEGFR-3 are mainly expressed in lymphatic endothelial cells (Karkkainen et al., Nat. Cell. Biol., 4(1): E2-5, 2002. This is important given that VEGF-A largely drives hemangiogenesis while VEGF-C mediates lymphangiogenesis.

VEGFRs are tyrosine kinase-type receptors (RTK) that belong to the immunoglobulin (Ig) superfamily of molecules. As such, they are comprised of 7 Ig-like domains in their extracellular segment, a transmembrane domain and an intracellular tyrosine kinase domain. The intracellular signaling cascade that follows VEGFRs activation is very complex and finely orchestrated. Several intracellular messenger systems become activated (i.e., PKC, PI3K, Src, MAPK) ultimately resulting in endothelial cell migration, proliferation, increased survival (i.e., anti-apoptosis) and increased vascular permeability (Ferrara et al., Nature, 438(7070): 967-74, 2005).

The imperative significance of VEGFs signaling to vasculogenesis and angiogenesis was made evident by the observation that the deletion of vegf-a, vegfr-1, vegfr-2 and vegfr-3 genes gave rise to lethal phenotypes that transpired at early embryonic stages. Abnormal blood vessel development and lethality were observed when inactivating the vegf-a gene in two independent studies (Carmeliet et al., Nature, 380(6573): 435-9, 1996; Ferrara et al., Nature, 380(6573): 439-42, 1996). The targeted deletion of vegfr-1 was associated with abnormal formation of blood vessel channels (Fong et al., Nature, 376(6535): 66-70, 1995), whereas abrogation of vegfr-2 resulted in failure of blood island formation (Shalaby et al., Nature, 376(6535): 62-6, 1995). VEGFR-3 deletion was also lethal and associated with aberrant development of large vessels and cardiac failure due to pericardial fluid accumulation (Dumont et al., Science, 282(5390): 946-9, 1998).

Site-directed mutagenesis studies (Wiesmann et al., Cell, 91(5): 695-704, 1997) and bioengineering of mosaic molecules (Jeltsch et al., J. Biol. Chem., 281(17): 12187-95, 2006) have unveiled critical ligand binding domains for VEGF-A and VEGF-C to their cognate receptors. Ig-like domain 2 of VEGFR-1 and Ig-like domains 2 and 3 of VEGFR-2 are critical for VEGF-A binding. VEGF-C, on the other hand, requires only Ig-like domain 2 of VEGFR-2 and Ig-like domain 1 and 2 of VEGFR-3.

A soluble splicing variant of VEGFR-1 (sVEGFR-1 or sFLT-1) was first described by Kendall and Thomas (*Proc. Natl. Acad. Sci. U.S.A.*, 90(22): 10705-9, 1993). This isoform receptor is comprised of the first 6 of the 71 g-like domains normally present in the extracellular segment of the membrane bound VEGFR-1. The alternative splicing event that gives rise to this soluble isoform takes place in the junction between exon 13 and intron 13/14 of VEGFR-1 pre-mRNA. In this case, intron 13/14 becomes part of exon 13 and due to the presence of an in-frame stop-codon, a truncated (hence soluble) protein is instead produced. sVEGFR-1 therefore has a unique c-terminus that includes 31 amino acids. Since the critical VEGF-A binding domain of VEGFR-1 is conserved in the alternate soluble protein, it avidly binds VEGF-A (Kendall et al., Proc. Natl. Acad. Sci. U.S.A., 90(22): 10705-9, 1993). The absence of the transmembrane domain and tyrosine kinase domains precludes receptor signaling and sVEGFR-1 is considered an endogenous anti-angiogenic molecule. Alternative splicing mechanisms similar to that of sVEGFR-1 are not at all uncommon. In fact, comparable splicing events are responsible for the generation of several other soluble variants derived from membrane bound proteins, such as, the alpha subunit of interleukin-5 (IL-5) receptor (Tavernier et al., Proc. Natl. Acad. Sci. U.S.A., 89(15): 7041-5, 1992), immunoglobulin heavy chain (Peterson, Immunol. Res., 37(1): 33-46, 2007), fibroblast growth factor receptors (Johnson et al., Mol. Cell. Biol., 11(9): 4627-34, 1991; Werner et al., Mol. Cell. Biol., 12(1): 82-8, 1992), and neuropilin-1 (Gagnon et al., Proc. Natl. Acad. Sci. U.S.A., 97(6): 2573-8, 2000).

Since its discovery in 1993, soluble VEGFR-1 has been extensively studied and implicated in several pathological states including pre-eclampsia (Tsatsaris et al., *J. Clin. Endocrinol. Metab.*, 88(11): 5555-63, 2003), sepsis (Tsao et al. Crit. Care Med., 2007), arthritis (Afuwape et al., *Gene Ther.*, 10(23): 1950-60, 2003) and cancer (Elkin et al., *J. Natl. Cancer Inst.*, 96(11): 875-8, 2004). In the cornea, it has been shown to exert a critical anti-angiogenic function. sVEGFR-1 is a key modulator of corneal avascularity, especially due to the presence of VEGF-A in the normal uninjured cornea (Ambati et al., *Nature*, 443(7114): 993-7, 2006).

SUMMARY OF THE INVENTION

One aspect of the present invention relates to nucleic acid molecules comprising the nucleotide sequence set forth in SEQ ID NO: 2, SEQ ID NO: 4, SEQ ID NO: 6, SEQ ID NO: 8, SEQ ID NO: 10 and variants thereof. Also an aspect of this invention are the polypeptides encoded by these sequences and variants thereof.

Another aspect of the invention relates to expression vectors, and host cells transformed or transfected with such expression vectors, comprising the nucleic acid molecules described above. Host cells transformed or transfected with the foregoing expression vectors are also provided.

In another aspect, the present invention relates to a method of inhibiting corneal graft rejection of a donor cornea. The method comprises administering an effective amount of sVEGFR-2 or to a subject in need thereof.

Another aspect of the present invention relates to an expression vector which, when expressed in a cell, results in expression of sVEGFR-2 in the cell.

In another aspect, the present invention provides a method of reducing sVEGFR-2 mRNA in a cell. The method comprises delivering to the cell an amount of siRNA targeting sVEGFR-2 effective for reducing the level of sVEGFR-2 mRNA.

In yet another aspect, the present invention provides a method of treating lymphedema. The method comprises administering an effective amount of an agent which inhibits the activity of sVEGFR-2 to a subject in need thereof.

In another aspect, the present invention provides an siRNA which is capable of reducing the level of sVEGFR-2 mRNA in a cell. Another aspect of the present invention provides an expression vector comprising a nucleic acid sequence which, when expressed in a cell, produces siRNA capable of reducing the level of sVEGFR-2 mRNA in the cell.

In still another aspect, the present invention provides a method of detecting tumor cell metastasis. The method comprises monitoring a tumor cell for expression of sVEGFR-2, wherein reduced expression of sVEGFR-2 is indicative of tumor cell metastasis.

Yet another aspect of the present invention provides an antibody which specifically binds sVEGFR-2. Another aspect of the present invention provides an oligonucleotide which specifically hybridizes with mRNA encoding sVEGFR-2.

In another aspect, the present invention provides a method for screening for a compound that interacts with sVEGFR-2.

The method comprises contacting sVEGFR-2 polypeptide or binding fragment thereof with a test compound, and determining if a complex is formed between sVEGFR-2 polypeptide or binding fragment thereof and the test compound.

Another aspect of this invention is a method for inhibiting lymphangiogenesis by contacting a subject or tissue in need thereof with an effective amount of sVEGFR-2.

Another aspect of this invention is a method for inhibiting lymphatic epithelial cell proliferation by contacting the cells with an effective amount of the sVEGFR-2.

Other methods, features and advantages of the present invention will be or become apparent to one with skill in the art upon examination of the following detailed descriptions. It is intended that all such additional methods, features and advantages be included within this description, be within the scope of the present invention, and be protected by the accompanying claims.

BRIEF DESCRIPTION OF THE DRAWINGS

FIG. 1 shows the nucleotide sequence (SEQ ID NO:1) corresponding to the mRNA of murine VEGFR2, including 5'UTR and 3'UTR (both underlined).

FIG. 2 shows the nucleotide sequence (SEQ ID NO:2) corresponding to the coding sequence of murine sVEGFR-2 mRNA, with the unique bases at the 3' end being highlighted.

FIG. 3 shows the deduced protein sequence (SEQ ID NO:3) of murine sVEGFR-2, with the unique carboxy terminal amino acids being highlighted.

FIG. 4 shows the nucleotide sequence (SEQ ID NO:4) corresponding to the coding sequence of human sVEGFR-2 mRNA, with the unique bases at the 3' end being highlighted.

FIG. 5 shows the deduced protein sequence (SEQ ID NO:5) of human sVEGFR-2, with the unique carboxy terminal amino acids being highlighted.

FIG. 6 shows the deduced nucleotide sequence (SEQ ID NO:6) corresponding to the coding sequence of *Macaca mulatta* (rhesus monkey) sVEGFR-2 mRNA, with the unique bases at the 3' end being highlighted.

FIG. 7 shows the deduced protein sequence (SEQ ID NO:7) of *Macaca mulatta* (rhesus monkey) sVEGFR-2, with the unique carboxy terminal amino acids being highlighted.

FIG. 8 shows the deduced nucleotide sequence (SEQ ID NO:8) corresponding to the coding sequence of *Rattus norvegicus* (rat) sVEGFR-2 mRNA, with the unique bases at the 3' end being highlighted.

FIG. 9 shows the deduced protein sequence (SEQ ID NO:9) of *Rattus norvegicus* (rat) sVEGFR-2, with the unique carboxy terminal amino acids being highlighted.

FIG. 10 shows the deduced nucleotide sequence (SEQ ID NO:10) corresponding to the coding sequence of *Bos taurus* (cow) sVEGFR-2 mRNA, with the unique bases at the 3' end being highlighted.

FIG. 11 shows the deduced protein sequence (SEQ ID NO:11) of *Bos taurus* (cow) sVEGFR-2, with the unique carboxy terminal amino acids being highlighted.

FIG. 12 shows the unique 3' end sequences for sVEGFR-2 mRNA from mouse, human, rhesus monkey, rat and cow.

FIG. 13 shows the unique carboxy terminal amino acid residues for sVEGFR-2 polypeptides from mouse, human, rhesus monkey, rat and cow.

Figure 31:
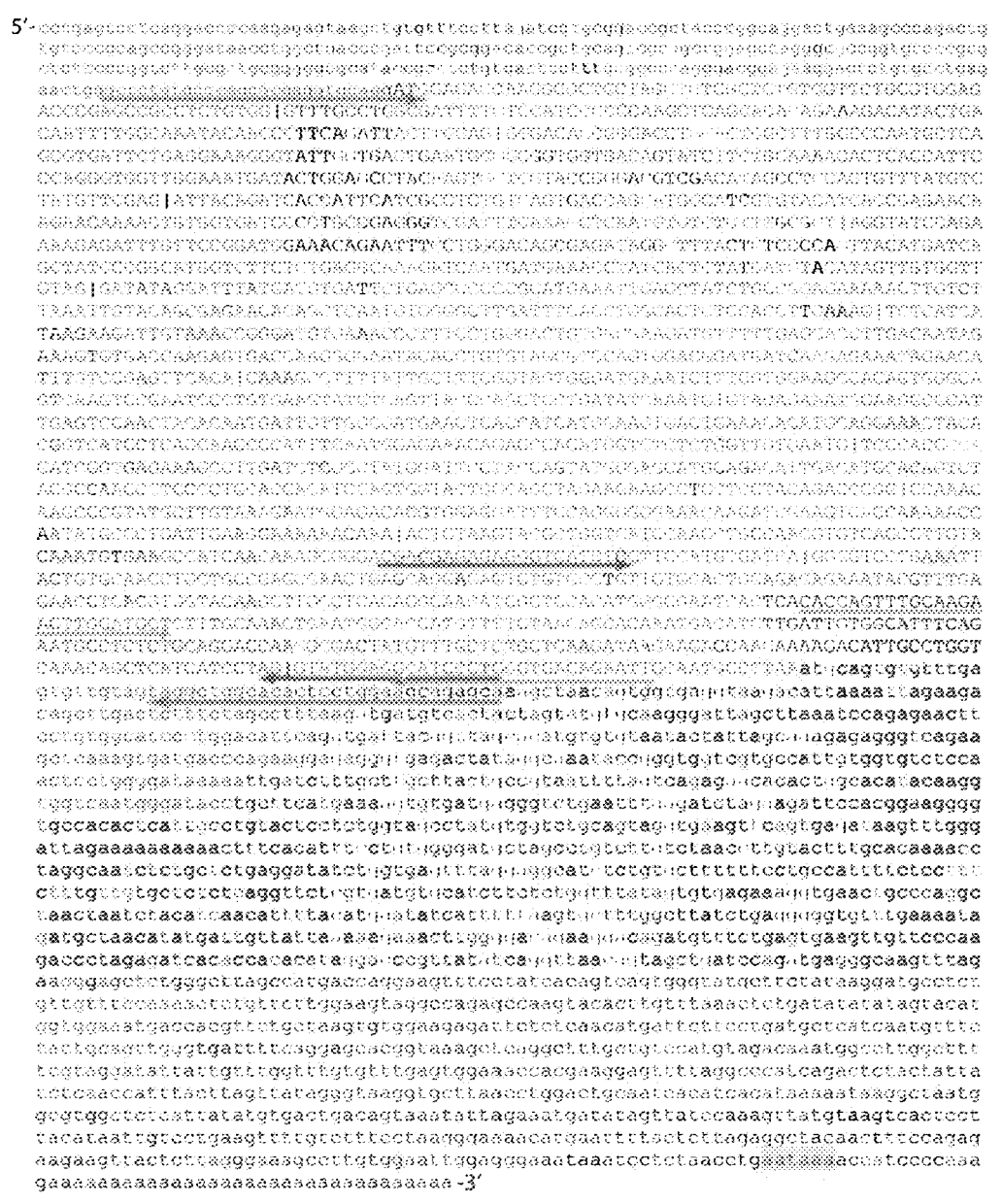

FIG. 31 is a nucleotide sequence corresponding to the sVEGFR-2 mRNA sequence including 5' and 3' untranslated region (UTR) (lowercase), open-reading frame (ORF) (uppercase) SEQ ID NO: 48. Exon boundaries are indicated by vertical lines (|). Novel 3' end of exon 13 shown in red. Red bar (|) shows alternative splicing site. Sequences targeted by primers underlined by arrow (forward ʃ) (reverse ~). Blue arrows sVegfr2 primer set for RT-PCR. Orange arrows sVegfr2 primer set used for real-time PCR. Green arrows correspond to primer set used to clone the ORF of sVegfr2. Polyadenylation signal site is highlighted in yellow

DETAILED DESCRIPTION OF THE INVENTION

Figure 14:
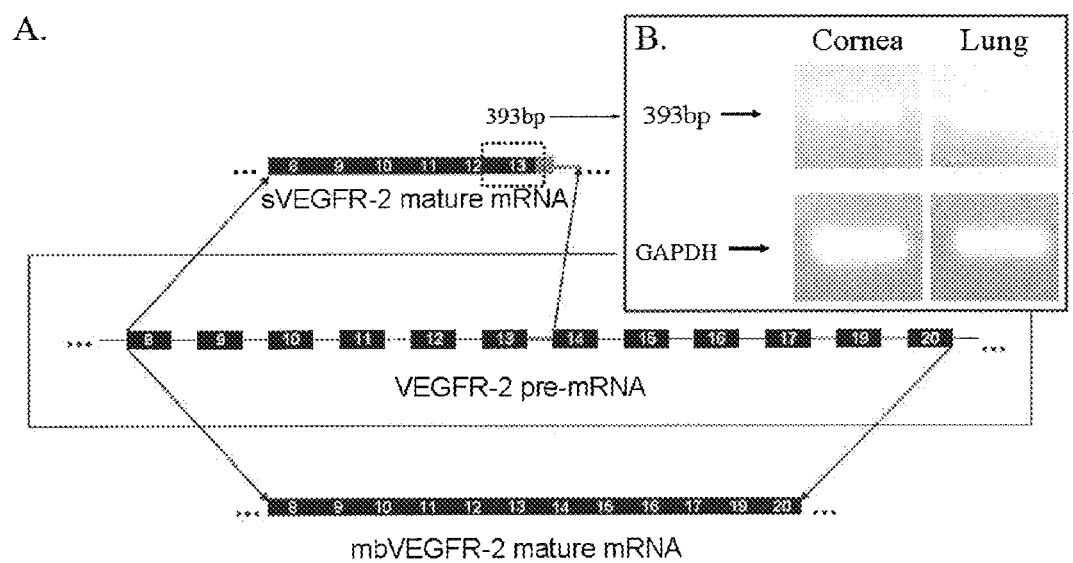
FIG. 14 shows a (A) representation of the alternative splicing event giving rise to sVEGFR-2, and (B) PCR products (393 bp) depicting the presence of a sVEGFR-2 splicing variant in the mouse cornea and lung. (black=exons; gray=intron 13-14)

Before the present compositions and methods are described, it is to be understood that the invention is not limited to the particular methodologies, protocols, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

VEGFR-2 is a cell surface receptor tyrosine kinase for VEGF that mediates angiogenesis. The present inventors have discovered that alternative splicing of the VEGFR-2 pre-mRNA results in production of an mRNA which directs the synthesis of a soluble protein, designated as sVEGFR-2. The present inventors have further determined that sVEGFR-2 modulates lymphatic vessel growth, such as in the cornea, and is also a marker of metastatic cancer, such as metastatic prostate cancer.

In particular, the present inventors have discovered a novel mRNA transcript that encodes a soluble variant of vascular endothelial growth factor receptor-2 (sVEGFR-2) in which intron 13-14 is not spliced out of the transcript during mRNA maturation and gives rise to a unique exon 13 and 3' untranslated region on this alternative transcript. The nucleic acid sequence corresponding to the complete murine mRNA sequence for sVEGFR-2, including the 5'UTR and 3'UTR, is shown in FIG. 1. The coding portion of the murine sVEGFR-2 mRNA sequence is shown in FIG. 2, with the unique bases at the 3' end being highlighted. The deduced protein sequence for murine sVEGFR-2 is shown in FIG. 3, with the unique carboxy terminal amino acids being highlighted. The human sVEGFR-2 mRNA coding and deduced protein sequences are shown in FIGS. 4 and 5, respectively, with the unique 3' bases and carboxy terminal amino acids being highlighted. The *Macaca mulatta* (rhesus monkey) sVEGFR-2 mRNA deduced coding and protein sequences are shown in FIGS. 6 and 7, respectively, with the unique 3' bases and carboxy terminal amino acids being highlighted. The *Rattus norvegicus* (rat) sVEGFR-2 mRNA deduced coding and protein sequences are shown in FIGS. 8 and 9, respectively, with the unique 3' bases and carboxy terminal amino acids being highlighted. The *Bos taurus* (cow) sVEGFR-2 deduced mRNA coding and protein sequences are shown in FIGS. 10 and 11, respectively, with the unique 3' bases and carboxy terminal amino acids being highlighted.

An embodiment of this invention is an isolated nucleic acid molecule comprising, consisting essentially of, or consisting of, the nucleotide sequence set forth in any of SEQ ID NO: 2, 4, 6, 8, or 10, or variants thereof. Variants include nucleotides having nucleotide sequences that have at least about 70%, 75%, 80%, 85%, 90%, 95%, 96%, 97%, 98%, or 99% sequence similarity to SEQ ID 2, 4, 6, 8, or 10, and preferably nucleotide sequences having at least about 70%, 75%, 78%, 80%, 85%, 90%, 95%, 96%, 97%, 98%, or 99% sequence identity to SEQ ID NO: 2, 4, 6, 8, or 10. Preferably the variants hybridize to SEQ ID NO: 2, 4, 6, 8 or 10, preferably the full length of SEQ ID NO: 2, 4, 6, 8 or 10, under high stringency conditions. Preferably the nucleic acid molecules encode a polypeptide comprising the amino acid sequence set for in SEQ ID NO: 3, 5, 7, 9 or 11 or a variant thereof.

The term "stringent conditions" as used herein refers to parameters with which the art is familiar. More specifically, stringent conditions, as used herein, refers to hybridization at 65° C. in hybridization buffer (3.5×.SSC, 0.02% Ficoll, 0.02% polyvinyl pyrrolidone, 0.02% Bovine Serum Albumin, 25 mM $NaH_2PO_4$ (pH 7), 0.5% SDS, 2 mM EDTA). SSC is 0.15M sodium chloride/0.015M sodium citrate, pH 7; SDS is sodium dodecyl sulphate; and EDTA is ethylenediaminetetracetic acid. After hybridization, the membrane upon which the nucleic acid is transferred is washed at 2×SSC at room temperature and then at 0.1-0.5×SSC/0.1×SDS at temperatures up to 68° C. SSC is 0.15M sodium chloride/0.15M sodium citrate, pH 7; SDS is sodium dodecyl sulphate; and EDTA is ethylenediamine tetraacetic acid. The foregoing set of hybridization conditions is but one example of stringent hybridization conditions known to one of ordinary skill in the art.

There are other conditions, reagents, and so forth which can be used, which result in stringent hybridization (see, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York). The skilled artisan will be familiar with such conditions, and thus they are not given here. It will be understood, however, that the skilled artisan will be able to manipulate the conditions in a manner to permit the clear identification of variants of the nucleic acid molecules of the invention. The skilled artisan also is familiar with the methodology for screening cells and libraries for expression of such molecules which then are routinely isolated, followed by isolation of the pertinent nucleic acid and sequencing.

The percent identity between the variants and SEQ ID NO: 2, 4, 6, 8 and 10 can be calculated using various, publicly available software tools developed by NCBI (Bethesda, Md.) that can be obtained through the internet (ftp:/ncbi.nlm.nih.gov/pub/). Exemplary tools include the BLAST system available at www.ncbi.nlm.nih.gov, which uses algorithms developed by Altschul et al. (*Nucleic Acids Res.* 25:3389-3402, 1997). Pairwise and ClustalW alignments (BLOSUM30 matrix setting) as well as Kyte-Doolittle hydropathic analysis can be obtained using the MacVector sequence analysis software (Oxford Molecular Group). Complements of the foregoing nucleic acids also are embraced by the invention.

The invention also includes degenerate nucleic acids which include alternative codons to those present in the nucleic acid molecules encoding sVEGFR-2 of this invention, particularly nucleic acids having the sequence set forth in SEQ ID NO: 2, 4, 6, 8 and 10. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

Another embodiment of this invention is a vector comprising the nucleic acid molecules or variants described herein. Preferably the vector is an expression vector comprising a nucleic acid molecule described herein in operable linkage with a promoter.

Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g. β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

Expression vectors containing all the necessary elements for expression are commercially available and known to those skilled in the art. See Molecular Cloning: A Laboratory Manual, J. Sambrook, et al., eds., Second Edition, Cold Spring Harbor Laboratory Press, Cold Spring Harbor, N.Y., 1989. Cells are genetically engineered by the introduction into the cells of heterologous DNA (RNA) encoding the sdph3.10 or sdp3.5 tumor associated polypeptide or fragment or variant thereof. The heterologous DNA (RNA) is placed under operable control of transcriptional elements to permit the expression of the heterologous DNA in the host cell.

Systems for mRNA expression in mammalian cells include e.g. those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1a, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710-4716, 1996). Still another preferred expression vector is an adenovirus, described by Stratford-Perricaudet, which is defective for E1 and E3 proteins (J. Clin. Invest. 90:626-630, 1992). The use of the adenovirus as an Adeno.P1A recombinant is disclosed by Warnier et al., in intradermal injection in mice for immunization against P1A (*Int. J. Cancer,* 67:303-310, 1996). Also included are bacterial systems for delivery of antigens to eukaryotic cells, such as those which utilize *Yersinia* (e.g. Stambach and Bevan, J. Immunol. 153:1603, 1994) and *Listeria* (Dietrich et al., *Nature Biotechnol.* 16:181, 1998). The expression vectors according to the invention include retroviral, adenoviral and lentiviral vectors comprising the nucleic acid molecules of this invention in operable linkage with a regulatory elements, e.g., a promoter or an enhancer. Promoters include, e.g, a CMV promoter, an SV40 promoter, a promoter of mouse U6 gene, and a promoter of human H1 gene.

Still another aspect of this invention are recombinant host cells transformed or transfected with the vectors of this invention. It will also be recognized from the examples that the invention embraces the use of the sVEGFR-2 sequences in expression vectors, as well as to transfect host cells and cell lines, be these prokaryotic (e.g., *E. coli*), or eukaryotic (e.g., CHO cells, COS cells, yeast expression systems and recombinant baculovirus expression in insect cells) for production of sVEGFR-2 polypeptides. Especially useful are mammalian cells such as mouse, hamster, pig, goat, primate, etc. They can be of a wide variety of tissue types, including mast cells, fibroblasts, oocytes and lymphocytes, and they may be primary cells or cell lines.

The invention provides for a method of producing an isolated polypeptide having the biological activity of sVEGFR-2, as described herein, whereby a host cell comprising a vector encoding sVEGFR-2 is cultivated under conditions allowing synthesis of the protein and the protein is isolated from the recombinant host cell.

Also an embodiment of this invention is an isolated polypeptide comprising the amino acid sequence set forth in SEQ ID NO: 3, 5, 7, 9 or 11 and variants thereof. Variants include polypeptides having amino acid sequences having at least about 70%, 75%, 78%, 80%, 85%, 90%, 95%, 96%, 97%, 98%, or 99% sequence similarity to the SEQ ID NO: 3, 5, 7, 9 or 11, preferably to the full length of 3, 5, 7, 9 or 11; variants may also include amino acid sequences having at least about 70%, 75%, 78%, 80%, 85%, 90%, 95%, 96%, 97%, 98%, or 99% sequence identity to SEQ ID NO: 3, 5, 7, 9 or 11, preferably to the full length of SEQ ID NO: 3, 5, 7, 9 or 11.

The skilled artisan will also realize that conservative amino acid substitutions may be made in the sVEGFR-2 polypeptides of this invention to provide functional variants of the foregoing polypeptides, i.e., variants which retain the functional capabilities of sVEGFR-2 described herein. As used herein, a "conservative amino acid substitution" refers to an amino acid substitution which does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Conservative variants of sVEGFR-2 comprise one of more conservative substitutions but retain the functional capabilities of sVEGFR-2.

As demonstrated in the examples below, sVEGFR-2 acts as an anti-lymphangiogenic agent in the cornea. Thus, in one aspect, the present invention relates to a method of inhibiting corneal graft rejection of a donor cornea comprising administering an effective amount of sVEGFR-2 to a subject in need thereof. Preferably the subject is one who has received a corneal allograft. The sVEGFR-2 may be administered to the subject before, after or simultaneously with corneal graft transplantation. Also, the sVEGFR-2 may be administered to the donor cornea before, after or simultaneously with corneal graft transplantation. Thus, the donor cornea may be exposed to a medium capable of providing sVEGFR-2. Any appropriate medium may be used for providing sVEGFR-2 to the donor cornea such as, for example, eye drops. Such a medium may contain, for example, sVEGFR-2 protein. In another embodiment, the medium comprises an expression vector which expresses sVEGFR-2 upon transfection of the donor cornea by the expression vector. The donor cornea may be, for example, bathed in a medium comprising the expression vector, or in another embodiment, the medium comprising the expression vector is injected into the donor cornea.

Another aspect of this invention is a method for inhibiting proliferation of lymphangioma lymphatic endothelial cells by contacting the cells with an effective amount of sVEGFR-2. The sVEGFR-2 may be a sVEGFR-2 polypeptide, e.g., a polypeptide comprising the amino acid sequence set forth in SEQ ID NO: 2, 4, 6, 8 or 10, or variants thereof, e.g., conservative variants thereof, or the sVEGFR-2 may be a sVEGFR-2 nucleic acid molecule encoding sVEGFR-2 polypeptide. For example the nucleic acid may be an expression vector that expresses sVEGFR-2 upon introduction into lymphatic endothelial cells.

Provided with the sequence information set forth above, one of skill in the art can prepare sVEGFR-2 suitable for therapeutic purposes using standard methods for recombinant production of proteins, although sVEGFR-2 produced by any method may be used.

For example, an expression vector may be used to introduce sVEGFR-2 into a cell. The expression vectors which can be used to deliver sVEGFR-2 according to the invention include, e.g., retroviral, adenoviral and lentiviral vectors. The expression vector includes a sequence which codes for sVEGFR-2. The expression vectors may include one or more promoter regions to enhance synthesis of sVEGFR-2. Promoters which can be used, e.g., include CMV promoter, SV40 promoter, promoter of mouse U6 gene, and promoter of human H1 gene. One or more selection markers may be included to facilitate transfection with the expression vector. The selection marker may be included within the expression vector, or may be introduced on a separate genetic element. For example, the bacterial hygromycin B phosphotransferase gene may be used as a selection marker, with cells being grown in the presence of hygromycin to select for those cells transfected with the aforementioned gene.

In another aspect, the present invention is directed to a method of reducing sVEGFR-2 mRNA in a cell. The method comprises delivering to the cell an amount of siRNA targeting sVEGFR-2 effective for reducing the level of sVEGFR-2 mRNA. The method may be used, for example, as a research tool in studying the effect of lowering the expression of sVEGFR-2 mRNA. Suitable siRNA for use in the method include mORF1, mUTR1, mORF2 and mUTR2, which are targeted to the unique tail of the mouse sVEGFR-2 mRNA, and hORF1, hORF2, hORF3 and hORF4, which are targeted to the unique tail of the human sVEGFR-2 mRNA. The nucleic acid sequences for these siRNAs are set forth below in Table 1.

TABLE 1

| siRNA | Nucleic acid sequence | SEQ ID NO. |
|---|---|---|
| mORF1 | GGTATGGAGGCATCCCTGGGT | 22 |
| mUTR1 | CAGTTAGCACATGTGTGTAAT | 23 |
| mORF2 | AATTGCAATGCCTTAAATGCA | 24 |
| mUTR2 | GGCTGGCACACTCCTGGAAGC | 25 |
| hORF1 | TAGGTAGGGAGACAATTCTGG | 26 |
| hORF2 | GTAGGGAGACAATTCTGGATC | 27 |
| hORF3 | TCATTGTGCAGAGGCAGTTGG | 28 |
| hORF4 | GAGGCAGTTGAATGCCTTAA | 29 |
| mouse sVEGFR-2-based | AATAGATGCTAACATATGATT | 30 |
| mouse sVEGFR-2-based | AAACTCTGATATATATAGTAC | 31 |
| mouse sVEGFR-2-based | AAATGATATAGTTATCCAAAG | 32 |
| mouse sVEGFR-2-based | AAATCCTCTAACCTGAATAAA | 33 |

The siRNAs for use in the present invention are designed according to standard methods in the field of RNA interference. Introduction of siRNAs into cells may be by transfection with expression vectors, by transfection with synthetic dsRNA, or by any other appropriate method. Transfection with expression vectors is preferred.

The expression vectors which can be used to deliver siRNA according to the invention include retroviral, adenoviral and lentiviral vectors. The expression vector includes a sequence which codes for a portion of the sVEGFR-2 target gene which is to be silenced. The target gene sequence is designed such that, upon transcription in the transfected host, the target RNA sequence forms a hairpin structure due to the presence of self-complementary bases. Processing within the cell removes the loop resulting in formation of a siRNA duplex. The double stranded RNA sequence should be less than 30 nucleotide bases; preferably the dsRNA sequence is 19-25 bases in length; more preferably the dsRNA sequence is 21 nucleotides in length.

The expression vectors may include one or more promoter regions to enhance synthesis of the target gene sequence. Promoters which can be used include, e.g., CMV promoter, SV40 promoter, promoter of mouse U6 gene, and promoter of human H1 gene.

One or more selection markers may be included to facilitate transfection with the expression vector. The selection marker may be included within the expression vector, or may be introduced on a separate genetic element. For example, the bacterial hygromycin B phosphotransferase gene may be used as a selection marker, with cells being grown in the presence of hygromycin to select for those cells transfected with the aforementioned gene.

Synthetic dsRNA may also be introduced into cells to provide gene silencing by siRNA. The synthetic dsRNAs are less than 30 base pairs in length. Preferably the synthetic dsRNAs are 19-25 base pairs in length. More preferably the dsRNAs are 19, 20 or 21 base pairs in length, optionally with 2-nucleotide 3' overhangs. The 3' overhangs are preferably TT residues.

Synthetic dsRNAs can be introduced into cells by injection, by complexing with agents such as cationic lipids, by use of a gene gun, or by any other appropriate method.

Lymphedema is a condition of localized fluid retention caused by a compromised lymphatic system. Lymphedema may be inherited or caused by injury to the lymphatic vessels. It is most frequently observed after lymph node dissection, surgery and/or radiation therapy in which damage to the lymphatic system is caused during treatment of cancer. Lymphedema is a notable complication in the treatment of breast cancer. Furthermore, lymphedema associated with filariasis is prevalent in many developing countries.

Because sVEGFR-2 is an anti-lymphangiogenic agent, reduction of sVEGFR-2 expression or activity can be used to treat lymphedema. Hence, in another aspect, the present invention is directed to a method of treating lymphedema comprising administering an effective amount of an agent which inhibits the expression or activity of sVEGFR-2 to a subject in need thereof. The inhibition of sVEGFR-2 activity can occur at the protein level and/or at the mRNA level.

Any compound which inhibits the activity of sVEGFR-2 may be used in the present invention. Thus, to reduce the level of mRNA, and ultimately the level of protein, siRNA or anti-sense oligonucleotides which target sVEGFR-2 can be administered to a subject in need of treatment. Appropriate siRNAs and their methods of production and administration have been described above. Appropriate anti-sense oligonucleotides can be prepared by methods known in the art.

Additional compounds suitable for inhibiting the activity of sVEGFR-2 include molecules which bind directly to sVEGFR-2, antibodies which bind sVEGFR-2, RNA, DNA or RNA/DNA aptamers which specifically bind sVEGFR-2. Additional compounds which inhibit the activity of sVEGFR-2 include inhibitory molecules which specifically bind sVEGFR-2, including an oligopeptide, small molecule antagonist (e.g., organic molecule having a molecular weight less than 2000, or less than 1000, or less than 500), ribozyme, intrabody or intraceptor. An intrabody refers to an antibody produced intracellularly, for example, a single chain antibody (such as a single chain Fv antibody fragment) expressed inside a cell transformed with an appropriate exogenous nucleic acid. An intraceptor refers to an receptor (such as a receptor for sVEGFR-2) produced intracellularly, for example, a sVEGFR-2 receptor expressed inside a cell transformed with an appropriate exogenous nucleic acid.

Additional compounds for inhibiting sVEGFR-2 include RNA, DNA or RNA/DNA aptamers directed against sVEGFR-2. Exemplary methods for making aptamers are described in U.S. Pat. Nos. 5,270,163, 5,840,867, 6,180,348 and 6,699,843.

Additional compounds for inhibiting sVEGFR-2 include antibodies which specifically bind sVEGFR-2. The antibodies of the present invention can be polyclonal or monoclonal, and the term antibody is intended to encompass both polyclonal and monoclonal antibodies. Antibodies of the present invention can be raised against an appropriate immunogen, including proteins or polypeptides of the present invention, such as isolated and/or recombinant mammalian sVEGFR-2 protein or portion thereof, or synthetic molecules, such as synthetic peptides.

Preparation of immunizing antigen, and polyclonal and monoclonal antibody production can be performed using any suitable technique. A variety of methods have been described (see, e.g., Kohler et al., *Nature*, 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) are isolated using selective culture conditions, and cloned by limiting dilution. Cells which produce antibodies with the desired specificity are selected by a suitable assay (e.g., ELISA).

Single chain antibodies, and chimeric, humanized or primatized (CDR-grafted) antibodies, as well as chimeric or CDR-grafted single chain antibodies, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023. B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology*, 10: 1455-1460 (1992), regarding primatized antibody, and Ladner et al., U.S. Pat. No. 4,946,778 and Bird, R. E. et al., *Science*, 242: 423-426 (1988)) regarding single chain antibodies.

In addition, functional fragments of antibodies, including fragments of chimeric, humanized, primatized or single chain antibodies, can also be produced. Functional fragments of foregoing antibodies retain at least one binding function and/or modulation function of the full-length antibody from which they are derived. For example, antibody fragments capable of binding to a mammalian sVEGFR-2 or portion thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Alternatively, antibodies can be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

The antibodies of the present invention can be used to modulate receptor or ligand function in research and therapeutic applications. For instance, antibodies can act as inhibitors to inhibit (reduce or prevent) (a) binding (e.g., of a ligand, a second inhibitor or a promoter) to the receptor, (b) a receptor signalling, (c) and/or a stimulatory function. Antibodies which act as inhibitors of receptor function can block ligand or promoter binding directly or indirectly (e.g., by causing a conformational change). For example, antibodies can inhibit receptor function by inhibiting binding of a ligand, or by desensitization (with or without inhibition of binding of a ligand).

Anti-idiotypic antibodies are also provided. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See, e.g., U.S. Pat. No. 4,699,880. Single chain, and chimeric, humanized or primatized (CDR-grafted), as well as chimeric or CDR-grafted single chain anti-idiotypic antibodies can be prepared, and are encompassed by the term anti-idiotypic antibody. Antibody fragments of such antibodies can also be prepared.

We studied the presence of sVEGFR-2 in non-metastatic and metastatic cells. For example, non-metastatic LnCap cells (human prostate cancer cells) are known to not permit the growth of lymphatic vessels in its stroma. However, once metastatic, these tumors are no longer capable of preventing lymphatic vessel growth. We have determined that sVEGFR-2 is expressed in non-metastatic LnCap cells but is not expressed in metastatic LnCap cells (see Example 4 below).

Thus, in one aspect, the present invention provides a method of detecting tumor cell metastasis comprising monitoring a tumor cell for expression of sVEGFR-2, wherein reduced expression of sVEGFR-2 is indicative of tumor cell metastasis. Preferably, the method detects prostate tumor cell metastasis. Detection of expression of sVEGFR-2 can be performed at the protein level; for example, through the use of an antibody which specifically binds sVEGFR-2 via known antibody binding assays. Alternatively, expression of sVEGFR-2 can be performed at the mRNA level; for example, through the use of oligonucleotide probes which specifically hybridize with sVEGFR-2 mRNA or via the use PCR with appropriate primers for sVEGFR-2.

The methods of the present invention can be used in any mammalian species, including human, monkey, cow, sheep, pig, goat, horse, mouse, rat, dog, cat, rabbit, guinea pig, hamster and horse. Humans are preferred.

The compounds of the present invention can be delivered directly or in pharmaceutical compositions along with suitable carriers or excipients, as is well known in the art. For example, a pharmaceutical composition of the invention may include a conventional additive, such as a stabilizer, buffer, salt, preservative, filler, flavor enhancer and the like, as known to those skilled in the art. Exemplary buffers include phosphates, carbonates, citrates and the like. Exemplary preservatives include EDTA, EGTA, BHA, BHT and the like. Compounds of the present invention may be administered either alone or in combination with another drug.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences.

Suitable routes of administration may, for example, include oral, rectal, transmucosal, transdermal, topical, nasal, or intestinal administration and parenteral delivery, including intramuscular, subcutaneous, intramedullary injections, as well as intrathecal, direct intraventricular, intravenous, intraperitoneal, intranasal, or intraocular injections. In addition, the agent or composition thereof may be administered sublingually or via a spray, including a sublingual tablet or a sublingual spray. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present invention, the present compounds are prepared in a formulation intended for oral administration. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Also, wetting agents such as sodium dodecyl sulfate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the compounds of the present invention can be administered transdermally, such as through a skin patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for stabilization may be employed.

For any composition used in the present methods of treatment, a therapeutically effective dose can be estimated initially using a variety of techniques well known in the art. For example, in a cell culture assay, a dose can be formulated in animal models to achieve a circulating concentration range that includes the IC50 as determined in cell culture. Dosage ranges appropriate for human subjects can be determined, for example, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

Dosages preferably fall within a range of circulating concentrations that includes the ED50 with little or no toxicity. Dosages may vary within this range depending upon the dosage form employed and the route of administration utilized. The exact formulation, route of administration, and dosage should be chosen, according to methods known in the art, in view of the specifics of a subject's condition.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In another embodiment, the present invention provides methods for screening compounds that interact with sVEGFR-2. The present invention is useful for screening compounds by using sVEGFR-2 polypeptide or binding fragments thereof in any of a variety of drug screening techniques. The sVEGFR-2 polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between sVEGFR-2 and the agent being tested. Alternatively, one can examine the diminution in complex formation between sVEGFR-2 and its target cell, monocyte, etc. caused by the agent being tested.

Thus, the present invention provides methods of screening for drugs or any other agents which can affect lymphangiogenesis. These methods comprise contacting such an agent with a sVEGFR-2 polypeptide or fragment thereof and assaying (i) for the presence of a complex between the agent and the sVEGFR-2 polypeptide or fragment, or (ii) for the presence of a complex between the sVEGFR-2 polypeptide or fragment and the cell, by methods well known in the art. In such competitive binding assays, the sVEGFR-2 polypeptide or fragment is typically labeled. After suitable incubation, free sVEGFR-2 polypeptide or fragment is separated from that present in bound form, and the amount of free or uncomplexed label is a measure of the ability of the particular agent to bind to sVEGFR-2 or to interfere with the sVEGFR-2 and agent complex.

Another technique for drug screening provides high throughput screening for compounds having suitable binding affinity to the sVEGFR-2 polypeptide and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with sVEGFR-2 polypeptide and washed. Bound sVEGFR-2 polypeptide is then detected by methods well known in the art. Purified sVEGFR-2 can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding sVEGFR-2 specifically compete with a test compound for binding to sVEGFR-2 polypeptides or fragments thereof. In this manner, the antibodies can be used to detect the presence of any peptide which shares one or more antigenic determinants with sVEGFR-2.

The present invention also contemplates the use of drug screening assays in which drugs or any other agents are monitored in a bioassay, such as the ability of the drug or agent to inhibit lymphangiogenesis. Such a drug screening assay may be used in conjunction with the various binding assays described above, i.e., drugs or other agents may be first tested for their ability to bind to sVEGFR-2, and those compounds having binding affinity for sVEGFR-2 are then tested in a bioassay, such as the ability of the drug or agent to inhibit lymphangiogenesis. Alternatively, the bioassay may be conducted with the drug or agent with or without a compound which blocks the action of sVEGFR-2, such as an antibody against sVEGFR-2. Inhibition of lymphangiogenesis with the drug or agent but no inhibition of lymphangiogenesis with drug or agent in the presence of a compound which blocks the action of sVEGFR-2 would be indicative of a compound that inhibits lymphangiogenesis by interacting with sVEGFR-2. Similar screening assays can be performed comparing lymphangiogenesis in wild-type cells versus cells in which the genes for sVEGFR-2 are knocked out, with inhibition of lymphangiogenesis in wild-type cells due to exposure to drug agent and no inhibition in the knockout cells being indicative of the drug or agent inhibiting lymphangiogenesis by interacting with sVEGFR-2.

These and other embodiments of the present invention will readily occur to those of ordinary skill in the art in view of the disclosure herein, and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

Example 1 sVEGFR-2 is the Product of Alternative Splicing of the VEGFR-2 Pre-mRNA

By modeling the alternative splicing event of sVEGFR-2 analogous to that of sVEGFR-1 (Kendall et al., *Proc. Natl. Acad. Sci. U.S.A.*, 90(22): 10705-9, 1993), we determined that the retention of intron 13-14 yields a truncated transcript variant whose protein product lacks the transmembrane and intracellular tyrosine kinase domains present in the full length cell surface protein. This is because an early termination codon is present 39 nucleotide downstream (13 amino-acids) from this alternate exon/intron junction.

Figure 15:
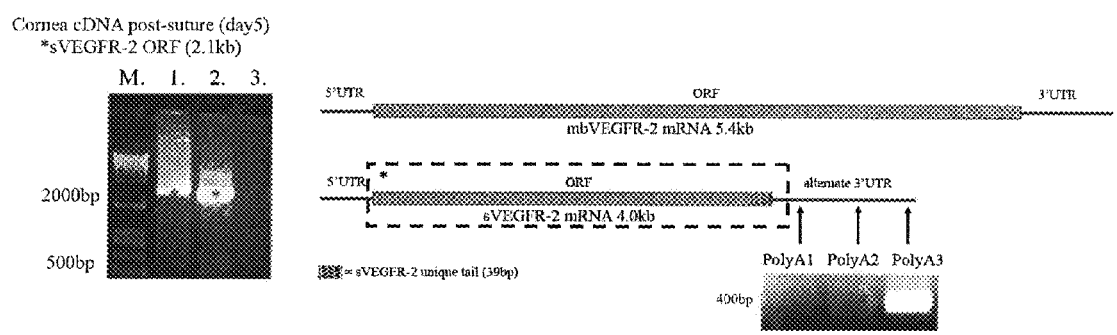
FIG. 15 shows a schematic representation of the mRNA structures and alignment between the membrane bound (mb) VEGFR-2 and soluble (s)VEGR-2 along with the results of 3'RACE PCR showing that PolyA3 is the active polyadenylation signal in the sVEGFR-2 mRNA (bottom right figure). Panel on left depicts PCR cloning of the entire sVEGFR-2 ORF (lane 1 and 2). M=marker; lane 3=negative control; *=cloned fragment of ORF within dotted box.

To demonstrate the presence of this novel soluble splicing variant in the mouse cornea and lung, we devised primers targeting an area of intron 13-14 and exon 12 (FIG. 14A). Targeting exon 12 allowed us to discern between amplification of cDNA derived from mRNA or from possible genomic DNA contamination based on amplicon size. PCR resulted in a 393 bp product encompassing the site where the alternative splicing event occurs (FIG. 14B). Computational analysis of intron 13-14 revealed 3 potential polyadenylation (PolyA) signal sequences (Cheng et al., *Bioinformatics*, 22(19): 2320-5, 2006). Using 3'RACE PCR we demonstrated that the third potential polyA signal, at position 3956-61, was indeed active (FIG. 15). Next, we used PCR to clone the entire ORF of sVEGFR-2 (2.1 kb) (FIG. 15, left panel) using cDNA from mouse cornea. All PCR products were cloned into a TOPO TA vector (Invitrogen) and DNA sequencing was performed by the University of Kentucky Advanced Genetic Technologies Center using a multi-color fluorescence based DNA sequencencer (ABI 3730xl).

Translation of the mouse sVEGFR-2 mRNA sequence and predicted sequence of the human sVEGFR-2 yields proteins that measure approximately 75.25 kDa and 75.91 kDa, respectively. While mouse sVEGFR-2 unique amino acid (aa) tail sequence is comprised of 13 aa (GMEASLGDRIAMP), the human unique c-terminus is predicted to be 16 aa long (GRETILDHCAEAVGMP). Polyclonal antibodies targeting these unique sequences are useful for specifically identifying and measuring mouse and human sVEGFR-2.

Example 2

Corneal sVEGFR-2 mRNA Levels are Increased after Corneal Injury

Figure 16:
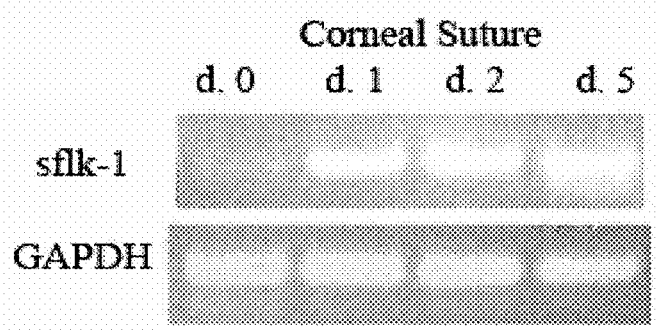
FIG. 16 shows an increase in intensity of PCR product band corresponding to sVEGFR-2 (sflk-1) 1 (d1), 2 (d2) and 5 (d5) days after suture placement relative to a house keeping gene (GAPDH).

The detection of sVEGFR-2 transcript in the cornea compared to lung (an organ known to express high levels of VEGFR-2 (Voelkel et al., *Am. J. Physiol. Lung Cell Mol. Physiol.*, 290(2): L209-21, 2006)) was nearly negligible by RT-PCR (lane 1 from FIG. 14B). We investigated the effects of corneal injury (i.e., suture placement) on the levels of sVEGFR-2 mRNA by RT-PCR. RNA was isolated from untreated corneas (d.0) and from corneas 1, 2 and 5 days after suture placement. We observed a relative increase in the mRNA level of sVEGFR-2 as early as 1 day after suture placement (FIG. 16).

Example 3

Figure 17:
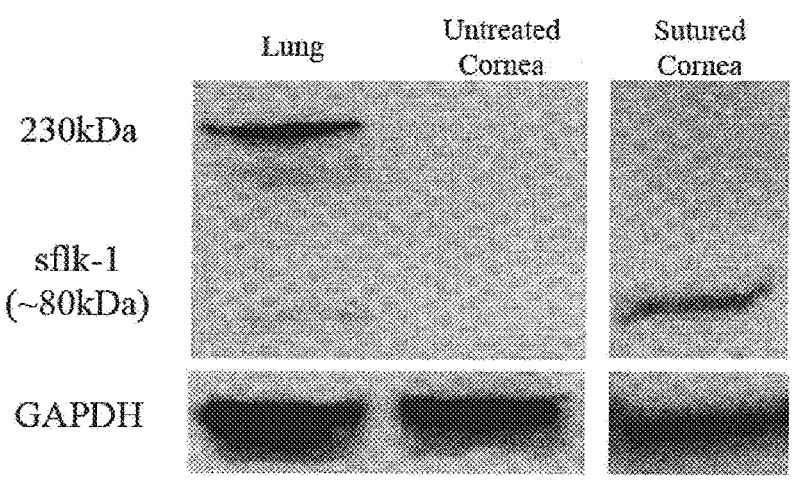
FIG. 17 shows Western blotting of lung, and untreated and sutured cornea, with antibody targeting the extracellular domain of VEGFR-2.

Corneal sVEGFR-2 Protein Levels are Undetectable in Normal Cornea, but Become Apparent after Corneal Injury We have previously shown that under normal/non-inflammatory conditions, the levels of VEGFR-2 protein in the mouse cornea are below the detection threshold of a Western blotting technique using a rabbit derived polyclonal antibody that targets the extracellular domain of VEGFR-2 (Ambati et al., *Nature*, 443(7114): 993-7, 2006). See also the 2nd lane of FIG. 17. However, experiments aimed at probing for the presence of VEGFR-2 in corneal lysate 5 days after suture placement have unveiled an immunoreactive band migrating at approximately 80 kDa (3rd lane of FIG. 17), which is like the band of comparable molecular weight detected in mouse lung (1st lane of FIG. 17). The 230 kDa band corresponding to mbVEGFR-2 (evident in lung lane of FIG. 17) does not appear in the mouse cornea even 5 days following injury. This indicates that the cornea preferentially expresses a truncated form of VEGFR-2.

Figure 18:
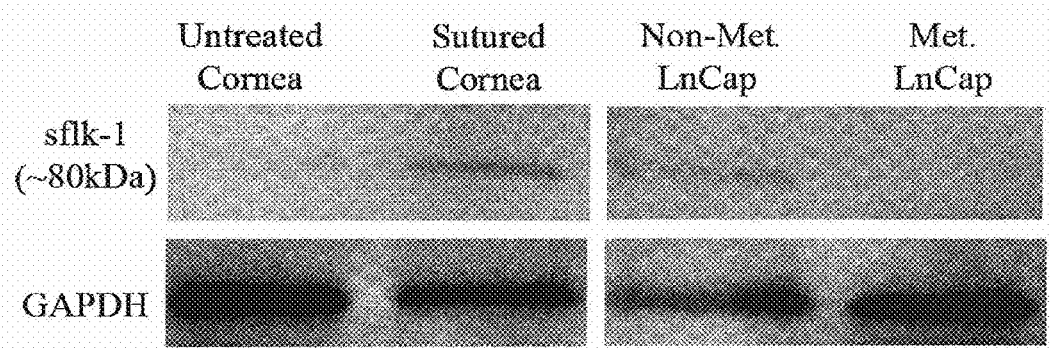
FIG. 18 shows Western blotting under reducing conditions for detection of 80 kDa immunoreactive band in untreated and sutured cornea, and non-metastatic and metastatic LnCap cells.

Example 4 sVEGFR-2 Protein is Expressed by Non-Metastatic Prostate Cancer Cells, but Undetected in Metastatic Prostate Cancer by Western Blotting To study the anti-lymphangiogenic activity of sVEGFR-2, we examined the presence of this molecule in lysates from LnCap (human prostatic cancer cells). Phenotypically, non-metastatic LnCap cells are known to not permit the growth of lymphatic vessels in its stroma; however, once metastatic, these tumors are no longer capable of preventing lymphatic vessel growth. These vessels become the pathway through which metastasis occur. Interestingly, we observed that sVEGFR-2 is detectable in lysates from the non-metastatic cells, but it is undetectable in the metastatic cell line by Western blotting (FIG. 18).

Example 5

Figure 19:
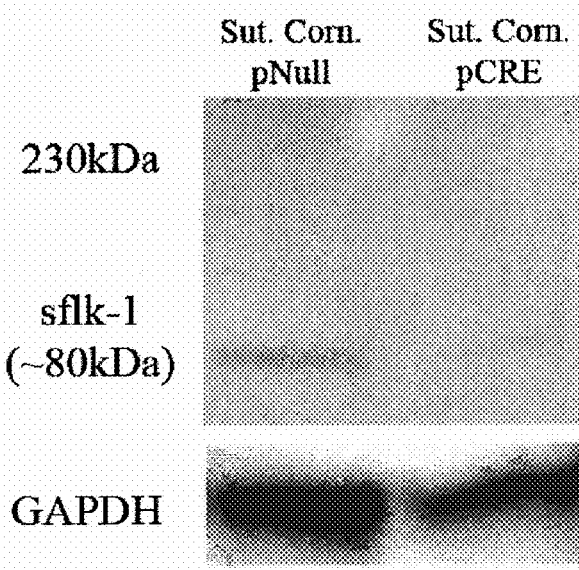
FIG. 19 shows Western blotting under reducing conditions for detection of 80 kDa immunoreactive band in pCRE treated eyes compared to pNull treated eyes in vegfr-$2^{loxP/loxP}$ mice 10 days after suture.
Figure 20:
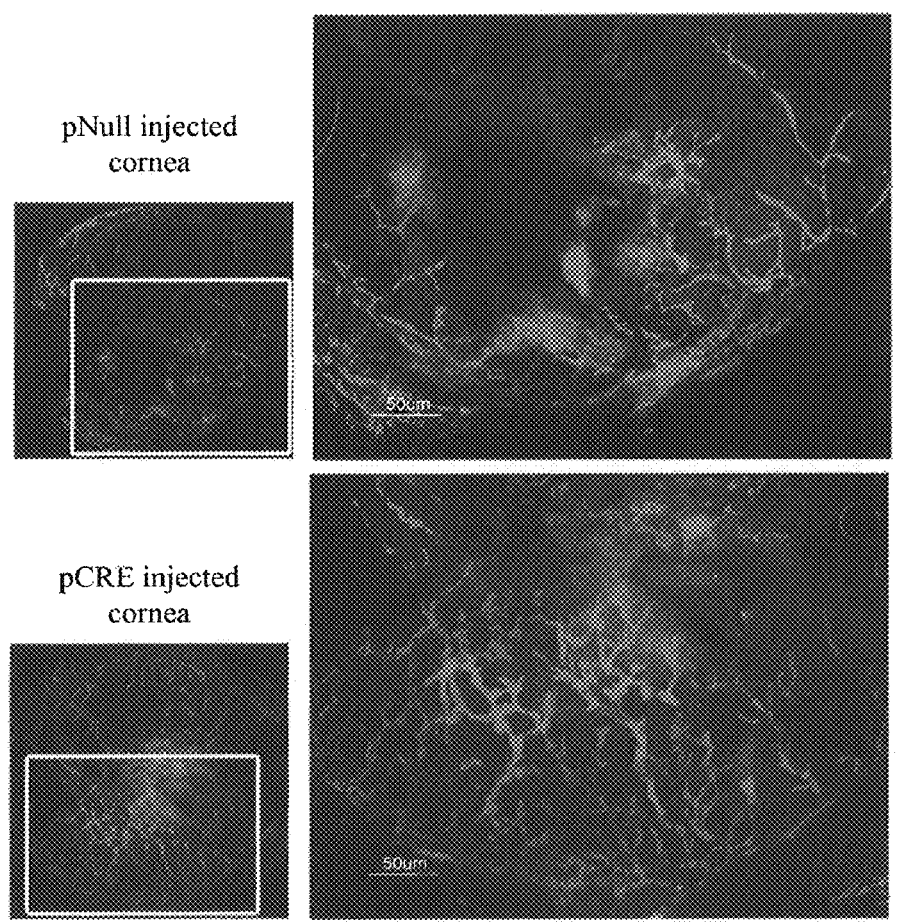
FIG. 20 illustrates corneal flat mounts showing suture-induced corneal lymphangiogenesis (lyve-1 (+) staining) in corneas of vegfr-$2^{loxP/loxP}$ mice injected with pNull versus pCRE 14 days post-suture.
Figure 21:
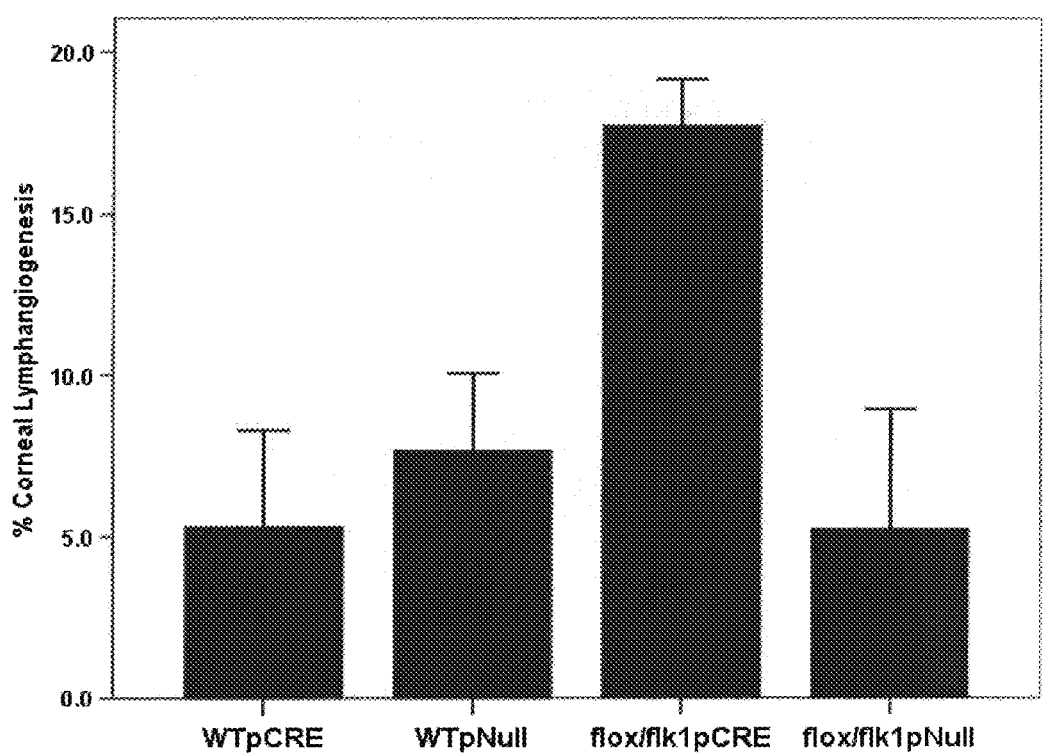
FIG. 21 shows suture-induced corneal lymphangiogenesis (lyve-1 (+) staining) in corneal flatmounts of wild-type and vegfr-$2^{loxP/loxP}$ mice injected with pCRE versus pNull. (*=p<0.05; Wilcoxon sign rank test), values expressed as median %, error bars depict 95% CI.

Genetic Ablation of sVEGFR-2 is Associated with Increased Suture Induced Lymphangiogenesis Because the systemic deletion of vegfr-2 gene is embryonically lethal (Shalaby et al., *Nature*, 376(6535): 62-6, 1995), we resorted to the Cre/lox-p conditional genetic ablation system aimed at excising the vegfr-2 gene from the mouse cornea of vegfr-2$^{loxP/loxP}$ (also known as flk-1$^{loxP/loxP}$) transgenic mice (gift of Dr. Janet Rossant, University of Toronto). Using the vegfr-2$^{loxP/loxP}$ mice, we attempted to attain conditional vegfr-2 ablation by injecting their corneas with either a plasmid encoding for the Cre-recombinase protein (pCRE) or an analogous empty plasmid (pNull) used as control in the fellow eye. These experiments showed that by using the above described paradigm 3 days prior to corneal suture placement, we were able to diminish the suture induced rise in sVEGFR-2 levels in the pCRE treated eyes to nearly undetectable amounts by Western blotting (FIG. 19). More importantly, the conditional genetic ablation of vegfr-2 in the cornea was associated with increased lymphangiogenesis in the pCRE treated eye compared to the pNull injected fellow eye of vegfr-2$^{loxP/loxP}$ as shown in FIGS. 20 and 21 (p<0.05). To ensure that the observed phenotypic changes were not caused by a non-specific effect of Cre-recombinase, we performed the same experiment in wild-type (WT) mice and found no difference in degree of lymphangiogenesis (lyve-1 positive staining) between WT injected with pCRE, WT injected with pNull and vegfr-2$^{loxP/loxP}$ injected with pNull (FIG. 21). Altogether, these data indicate that sVEGFR-2 is involved in modulating lymphangiogenesis.

Example 6

Effect of sVEGFR-2 on Corneal Lymphangiogenesis and Corneal Allograft Survival

Figure 22:
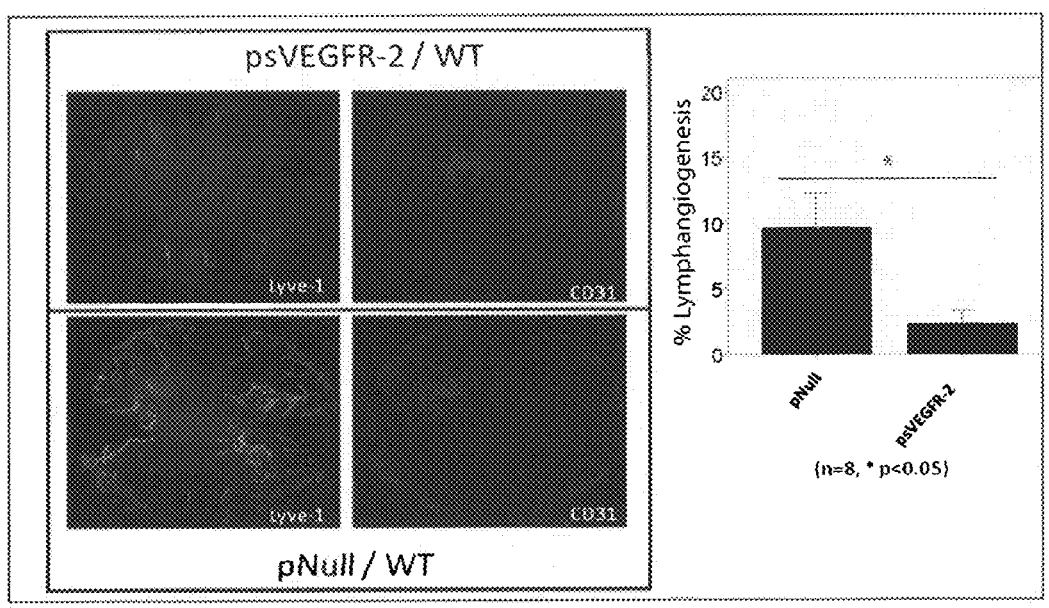
FIG. 22 illustrates that transfection of corneal epithelial cells with a naked plasmid coding for sVEGFR-2 (psVEGFR-2) is associated with diminished suture-induced lymphangiogenesis compared with transfection with a control empty plasmid (pNull) (n=8; *P<0.05).
Figure 23:
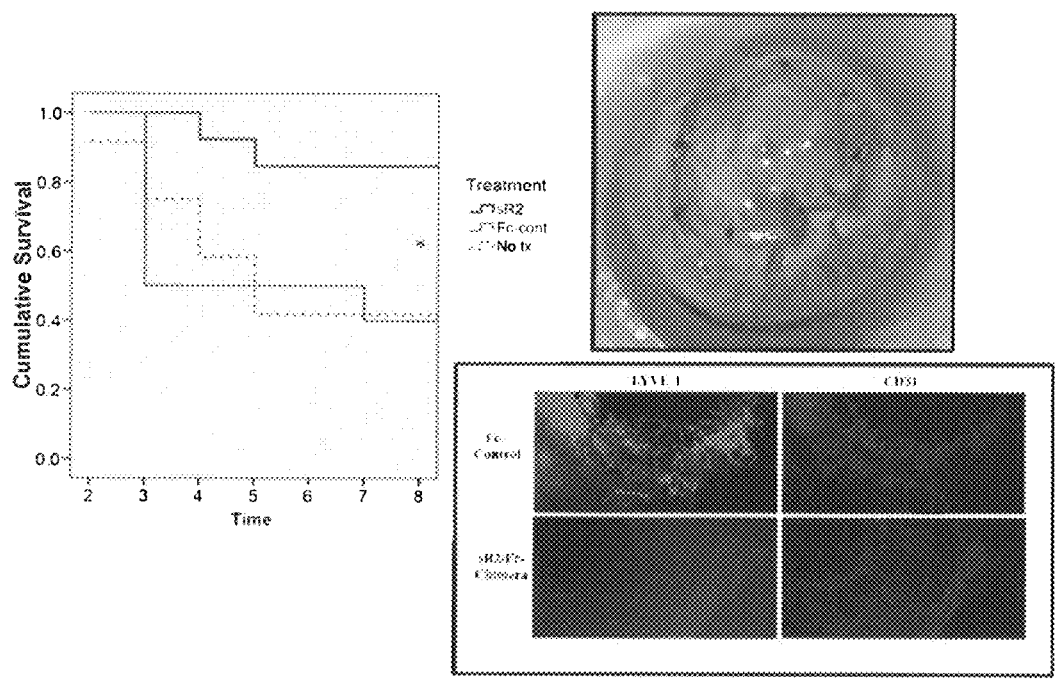
FIG. 23 shows that preemptive administration of sVEGFR-2 into the cornea significantly increases corneal allograft survival (n=10-12; *P<0.05) and prevents lymphatic vessels from crossing the interface between the graft and its bed (recipient corneal rim).

FIG. 22 illustrates that transfection of corneal epithelial cells with a naked plasmid coding for sVEGFR-2 (psVEGFR-2) is associated with diminished suture-induced lymphangiogenesis compared with transfection with a control empty plasmid (pNull) (n=8; *P<0.05). FIG. 23 illustrates that preemptive administration of sVEGFR-2 into the cornea significantly increases corneal allograft survival (n=10-12; *P<0.05) and prevents lymphatic vessels from crossing the interface between the graft and its bed (recipient corneal rim).

It will be appreciated that, although specific embodiments of the invention have been described herein for purposes of illustration, various modifications may be made without departing from the spirit and scope of the invention. All such modifications and variations are intended to be included herein within the scope of this disclosure and the present invention and protected by the following claims.

Example 7

Localizing sVEGFR-2 in the Cornea

The sVegfr2 transcript described herein was localized by in situ hybridization principally to the corneal epithelium. Immunolocalization using AA21127 in the newborn mouse demonstrated the presence of sVEGFR-2 in the corneal epithelium and stroma. In the adult cornea, sVEGFR-2 was more abundant in the epithelium than in the stroma. In contrast, sVEGFR-2 was not immunolocalized in the adjoining conjunctiva, which contains lymphatic vessels. sVEGFR-2 was identified in the cornea as a 75 kDa species by western blotting both by AA21127 and T014. However, 230 kDa membrane bound VEGFR-2 (mbVEGFR-2) was not detected in the cornea by western blotting using T014 or by immunofluorescence using an antibody targeting the carboxyl-terminus of mbVEGFR-2, which is not present in sVEGFR-2. Neither was the mbVegfr2 transcript detected in the cornea by RT-PCR. Thus, the mouse cornea expresses sVEGFR-2 but not mbVEGFR-2.

Example 8 sVEGFR-2 is Essential for Alymphatic Cornea

To define the function of sVEGFR-2 in the cornea, we targeted it using multiple strategies. Because Vegfr2$^{-/-}$ mice die in utero (Shalaby, F., et al. *Nature* 376, 62-66 (1995), we conditionally ablated corneal sVEGFR-2 using a Cre-loxP strategy. This strategy enabled the specific targeting of sVEGFR-2 because mbVEGFR-2 is not expressed in the cornea. We created Vegfr2$^{loxP/loxP}$ mice by targeting exon 1 and interbred them with LeCre mice that constitutively and uniformly express Cre recombinase in the corneal 5. Mice of all genotypes were born at the expected mendelian ratios and were macroscopically indistinguishable from one another. Strikingly however, all LeCre/Vegfr2$^{loxP/loxP}$ mouse corneas (n=30), which verifiably lacked sVEGFR-2 expression, were densely covered with lymphatic vessels on the day of birth (P0). These vessels were identified as lymphatics by virtue of their intense LYVE-1 reactivity, moderate CD31 reactivity, nuclear Prox1 expression, and blind-ended morphology. Although LYVE-1+ macrophages have been described in the cornea[16], nuclear expression of Prox1 in these vessels confirms their lymphatic origin. Furthermore, ultrastructural examination showed that these vessels lacked erythrocytes, did not have a continuous basement membrane, and contained partly overlapping thin endothelial cells free of pericyte coverage, all features typical of lymphatics. Surprisingly these corneas were not invaded by blood vessels as demonstrated by the absence of CD31+ LYVE-1− vessels. We confirmed this independently by demonstrating that the vessels in these corneas did not express MECA-32, a blood vessel-specific marker. All littermate control corneas (n=30) were, like wild-type mice, devoid of both lymphatic and blood vessels.

Example 9 sVEGFR-2 is a VEGF-C Antagonist

Figure 24:
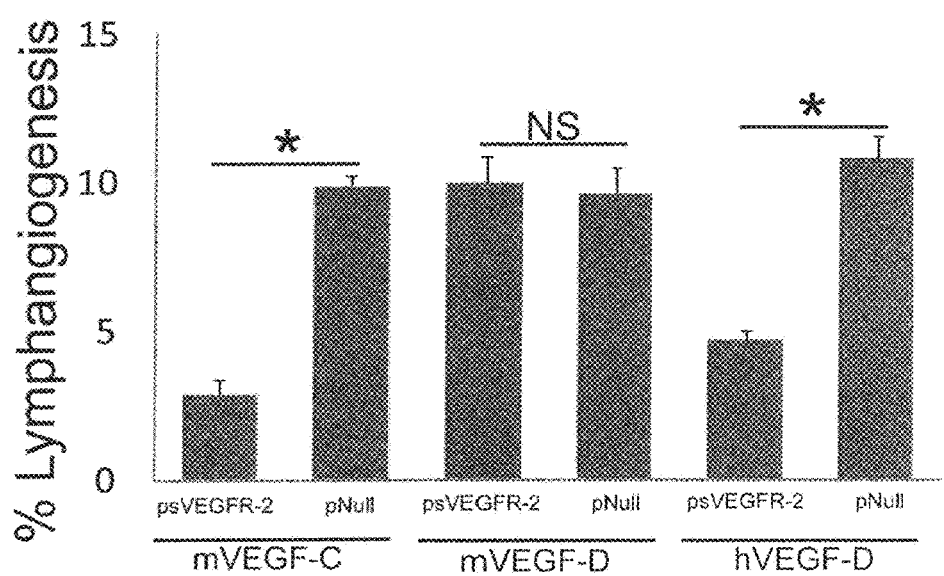
FIG. 24 shows that sVEGFR-2 blocked lymphangiogenesis induced by mouse VEGF-C and human VEGF-D, but not by mouse VEGF-D. Corneal area occupied by lymphatic vessels (LYVE-1+) induced by pmVEGF-C and phVEGF-D injection in wild-type mouse corneas was reduced by psVEGFR-2 compared to pNull; however, psVEGFR-2 did not inhibit pmVEGF-D induced lymphangiogenesis. (NS, not significant; *, P<0.05; Significance by Mann Whitney U test. n=4. Error bars depict s.e.m.)

The results presented herein indicate that the developing mouse cornea is exposed to pro-lymphangiogenic stimuli that are counterbalanced by sVEGFR-2 to create an alymphatic cornea. Indeed wild-type P0 corneas, unlike adult corneas, expressed VEGF-C. Without wishing to be bound by theory, we reasoned that sVEGFR-2 ablation led to spontaneous corneal lymphangiogenesis because sVEGFR-2 trapped VEGF-C. Indeed, the levels of sVEGFR-2 (2,395±260 pg/ml; 1,655.8±44.62 pg per mg of total protein) in the wild-type P0 cornea were sufficiently in excess of VEGF-C (65.7±4.7 pg/ml; 45.4±3.2 pg per mg of total protein) to fulfill a trapping function. We confirmed that sVEGFR-2, which contains the VEGF-C binding Ig-like domain 2 of mbVEGFR-2 (Jeltsch, M., et al. *J Biol Chem* 281, 12187-12195 (2006)), interacted with VEGF-C by immunoprecipitation and inhibited both VEGFR-3 phosphorylation and proliferation of lymphatic endothelial cells (LECs) stimulated by VEGF-C. We also found that VEGF-C-induced corneal lymphangiogenesis was inhibited by psVEGFR-2 (FIG. 24). Collectively, these data are consistent with a model of sVEGFR-2 acting as an endogenous sink for VEGF-C during corneal development and thereby establishing an alymphatic cornea.

It has been reported that mouse VEGFR-2 binds human but not mouse VEGF-D (Baldwin, M. E., et al. *J Biol Chem* 276, 19166-19171 (2001)). Consistent with this report, psVEGFR-2 inhibited corneal lymphangiogenesis induced by human but not mouse VEGF-D (FIG. 24). We also found that, unlike VEGF-C, VEGF-D was not expressed in the newborn mouse cornea, thus accounting for the ability of sVEGFR-2 to maintain the alymphatic nature of the cornea.

Example 10 sVEGFR-2 Displays Selective Anti-Lymphangiogenic Effects sVEGFR-2 Inhibits Reparative Lymphangiogenesis To determine the function of sVEGFR-2 in the adult, we studied a clinically relevant mouse model of suture-induced corneal neovascularization (Streilein., et al., *Invest Opthalmol Vis Sci* 37, 413-424 (1996)). Suture injury increased corneal sVEGFR-2 expression in wild-type mice. Ablating sVEGFR-2 by intracorneal administration Ambati, B. K., et al. *Nature* 443, 993-997 (2006) of a plasmid encoding for Cre recombinase (pCre) in Vegfr2$^{loxP/loxP}$ mice markedly increased suture-induced lymphangiogenesis but not hemangiogenesis compared to pNull administration by 161±9% (P<0.05, n=5). This outstripping of hemangiogenesis by lymphangiogenesis suggests that induction of endogenous sVEGFR-2 by injury is a compensatory anti-lymphangiogenic response. Both pCre and pNull-injected corneas of wild-type mice showed similar degrees of lymphangiogenesis following suture injury, excluding a non-specific effect of Cre recombinase (FIG. 25A). pCre induced enhancement of suture-induced lymphangiogenesis in Vegfr2$^{loxP/loxP}$ mice was reduced by a VEGFR-3 tyrosine kinase inhibitor (Kirkin, V., et al., *Eur J Biochem* 268, 5530-5540 (2001); Le Bras, B., et al., *Nat Neurosci* 9, 340-348 (2006); Bruyere, F., et al., *Nat Methods* 5, 431-437 (2008) and Ny, A., et al., *Blood* 112, 1740-1749 (2008)), supporting the concept that endogenous sVEGFR-2 is an in vivo VEGF-C antagonist. Conversely, augmenting sVEGFR-2 via in vivo transfection (Ambati, B. K., et al., *Nature* 443, 993-997 (2006)) of wild-type mouse corneas with psVEGFR-2, but not pNull, reduced suture injury-induced lymphangiogenesis but not hemangiogenesis by 76±6% (P<0.05, n=5) (FIG. 3c,d).

Monomeric sVEGFR-2 does not Block Hemangiogenesis

Figure 25:
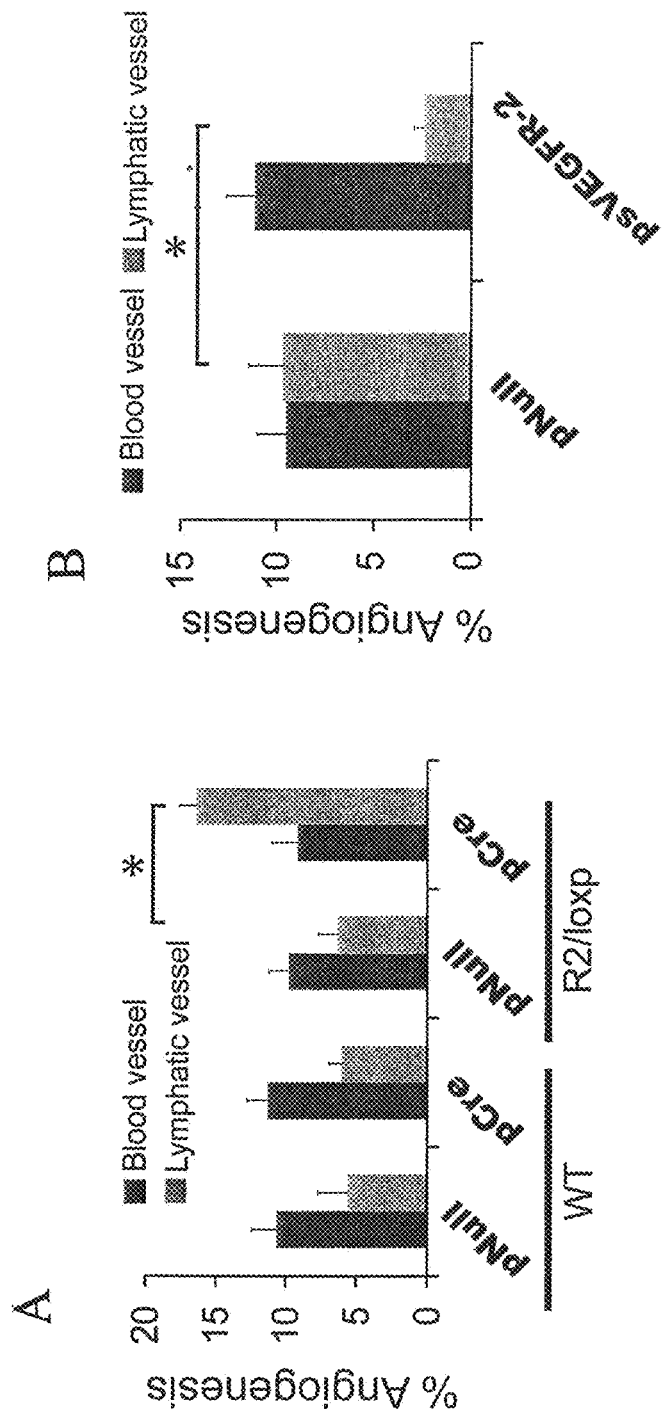
FIG. 25 (A) pCre-injected R2/loxP corneas showed increased area of lymphangiogenesis (LYVE-1+-grey) compared to pNull (*P<0.05, Significance by Mann Whitney U test, n=5). Hemangiogenesis (CD31+/LYVE-1−) (black) was unaffected by pCre compared to pNull. pCre treatment did not alter the hemangiogenic (black) or lymphangiogenic (grey) response in Balb/C wild-type (WT) mice (n=5-6); (B) Corneal area occupied by blood vessels (CD31+/LYVE-1−, black bar) was not affected by psVEGFR-2 compared to pNull; however, the area occupied by lymphatic vessels (LYVE-1+, grey bar) was significantly reduced by psVEGFR-2 (*P<0.05, Significance by Mann Whitney U test, n=5). Error bars depict s.e.m.

These selective anti-lymphangiogenic effects of sVEGFR-2 were unexpectedly specific because mbVEGFR-2 is capable of binding VEGF-A and promoting hemangiogenesis. To explain this selective bioactivity, we first sought to determine whether sVEGFR-2 existed in monomeric or dimeric form because a recombinant form of the ectodomain of mbVEGFR-2 has been shown to be a monomer that has little or no affinity for VEGF-A compared to a dimeric recombinant VEGFR-2/Fc fusion protein (Roeckl, W., et al., *Exp Cell Res* 241, 161-170 (1998); Fuh, G., et al., *J Biol Chem* 273, 11197-11204 (1998) and; Wiesmann, C., et al., *Cell* 91, 695-704 (1997)). We found that recombinant sVEGFR-2 migrated at equivalent apparent molecular masses under both non-reducing and reducing conditions of western blotting (FIG. 25A) confirming that it exists as a monomer. In contrast, the migration of VEGFR-2/Fc was consistent with it being a dimer. Next we tested the in vivo effects of monomeric sVEGFR-2 and dimeric VEGFR-2/Fc on models of corneal neovascularization induced by injury or growth factors. We found that suture-induced corneal hemangiogenesis, which is driven principally by upregulation of endogenous VEGF-A (Cursiefen, C., et al., *J Clin Invest* 113, 1040-1050 (2004)), was inhibited by VEGFR-2/Fc but not sVEGFR-2 (FIG. 25B). Similarly, VEGF-A-induced corneal hemangiogenesis was inhibited by VEGFR-2/Fc but not by sVEGFR-2 or psVEGFR-2 (FIG. 25C). These functional data demonstrate that only the dimeric form of VEGFR-2 can antagonize VEGF-A-driven hemangiogenesis in vivo and corroborate the previously reported in vitro differential VEGF-A binding avidity between monomeric and dimeric forms of VEGFR-2.

Example 11 sVEGFR-2 Enhances Corneal Transplant Survival

Figure 26:
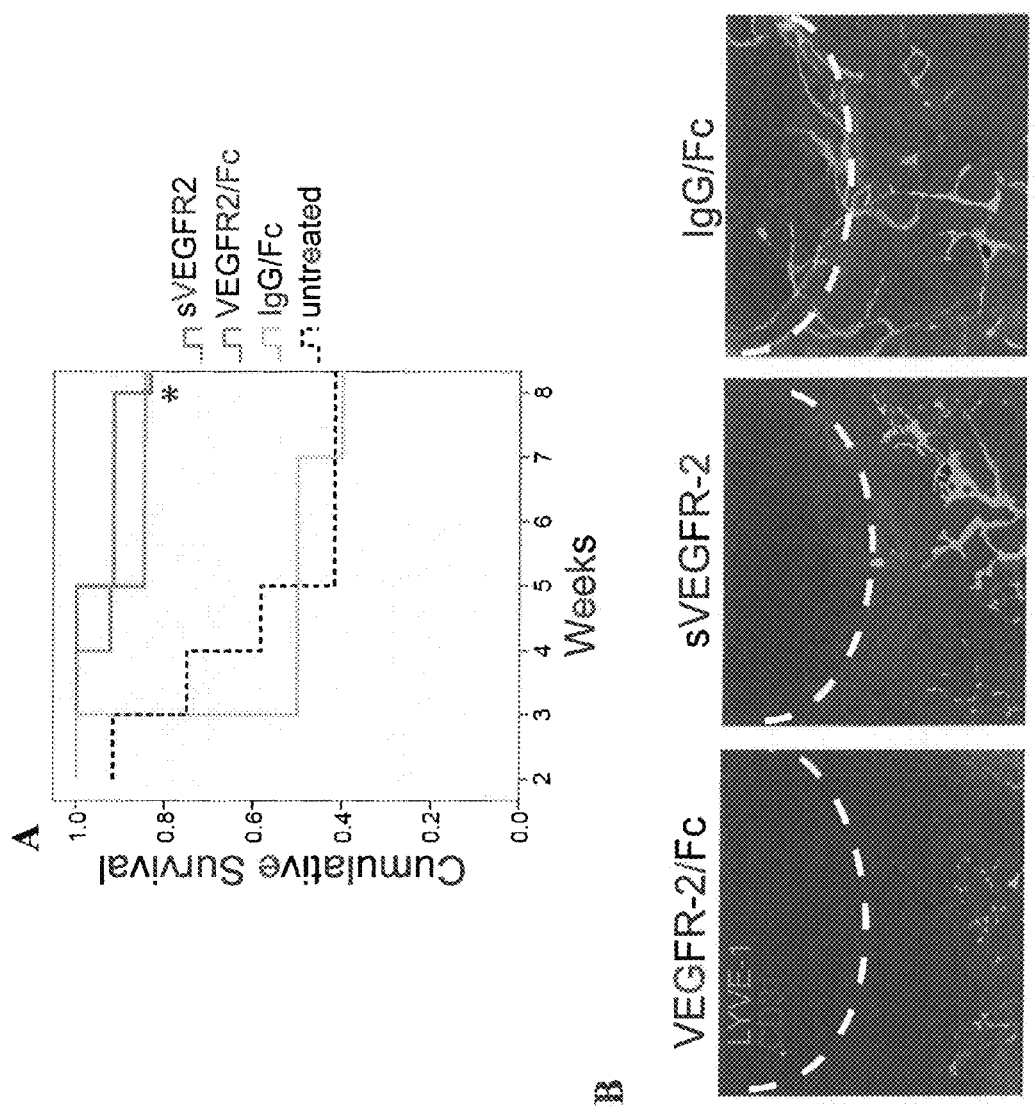
FIG. 26: sVEGFR-2 reduces lymphatic invasion into and rejection of corneal allografts. (A) Kaplan-Meier survival curves show increase in allograft survival in BALB/c hosts (*P<0.05, n=10-13) treated with single intracorneal injection of dimeric VEGFR-2/Fc (blue) or monomeric sVEGFR-2 (red) compared to IgG/Fc (green) or untreated (dotted line) groups. (B) Representative corneal flat mounts of transplanted mouse corneas showing the incursion of CD31$^+$/ LYVE-1$^-$ (red) blood and LYVE-1$^+$ (green) lymphatic vessels through the recipient-donor interface (dotted-line) in corneas treated with IgG/Fc (right). Center picture shows the absence of lymphatic vessels in the allograft from cornea treated with a single injection of monomeric sVEGFR-2, despite abundant blood vessel incursion. On the left, representative flat mount showing that a single injection of dimeric VEGFR-2/Fc inhibited incursion of both blood and lymphatic vessels.

Because lymphangiogenesis has been implicated in corneal allograft rejection (Cursiefen, et al., *Cornea* 22, 273-281 (2003)), we studied the function of sVEGFR-2 in a mouse model of corneal transplantation. A single intracorneal administration of dimeric VEGFR-2/Fc more than doubled transplant survival rate (105% increase compared to the IgG/Fc treatment and 101% compared to no treatment; P<0.05, n=10-13; FIG. 26a). The dramatic reduction in rejection rate induced by VEGFR-2/Fc administration (75% compared to the IgG/Fc treatment and 74% compared to no treatment) is consistent with the observed reduction in blood vessel and lymphatic sprouting through the donor-recipient interface (FIG. 26b). Surprisingly, a single intracorneal administration of monomeric sVEGFR-2 induced the same degree of corneal allograft survival as dimeric VEGFR-2/Fc despite reducing sprouting only of lymphatic but not blood vessels through the donor-recipient interface (FIG. 26a,b). These data suggest that impairment of the establishment of the afferent arm of the immune-arc-reflex (Liu, et al. *J Exp Med* 195, 259-268 (2002); Yamagami, S. & Dana, M. R., *Invest Opthalmol Vis Sci* 42, 1293-1298 (2001)) alone is sufficient to enhance corneal allograft survival. Further, the rate of allograft survival following a single local administration of sVEGFR-2 was at least as great as the rate of survival induced by multiple systemic administrations of a VEGFR-3 antagonist in a prior study (Chen, L., et al. *Nat Med* 10, 813-815 (2004)). Apart from reducing lymphangiogenesis, and without wishing to be bound by theory, it also is possible that sVEGFR-2 promoted allograft survival by inhibiting VEGF-C-induced VEGFR-3 signaling in corneal dendritic cells and preventing their transmigration into the draining lymph node (Chen, L., et al. *Nat Med* 10, 813-815 (2004)). Collectively, these data provide a novel experimental strategy to uncouple hemangiogenesis from lymphangiogenesis and a new endogenous therapeutic target for improving survival of this most common solid transplant in humans.

Example 12 sVEGFR-2 Inhibits Lymphangioma Cellular Proliferation

Lymphangioma is a common disfiguring childhood neoplasia whose etiology is unknown. Human lymphangioma endothelial cells (LaECs) produce VEGF-C and express VEGFR-3 (Kaipainen, A., et al. *Proc Natl Acad Sci USA* 92, 3566-3570 (1995); Huang, H. Y., et al.; *Lab Invest* 81, 1729-1734 (2001), and; Norgall, S., et al., *BMC Cancer* 7, 105 (2007)), suggesting that their growth could be inhibited by disrupting this axis. Previously we described the isolation of LaECs from axillary lymphangiomas in two human infants (Norgall, S., et al., *BMC Cancer* 7, 105 (2007)). We found that sVEGFR-2 abolished VEGF-C-induced proliferation of both these LaECs.

Figure 27:
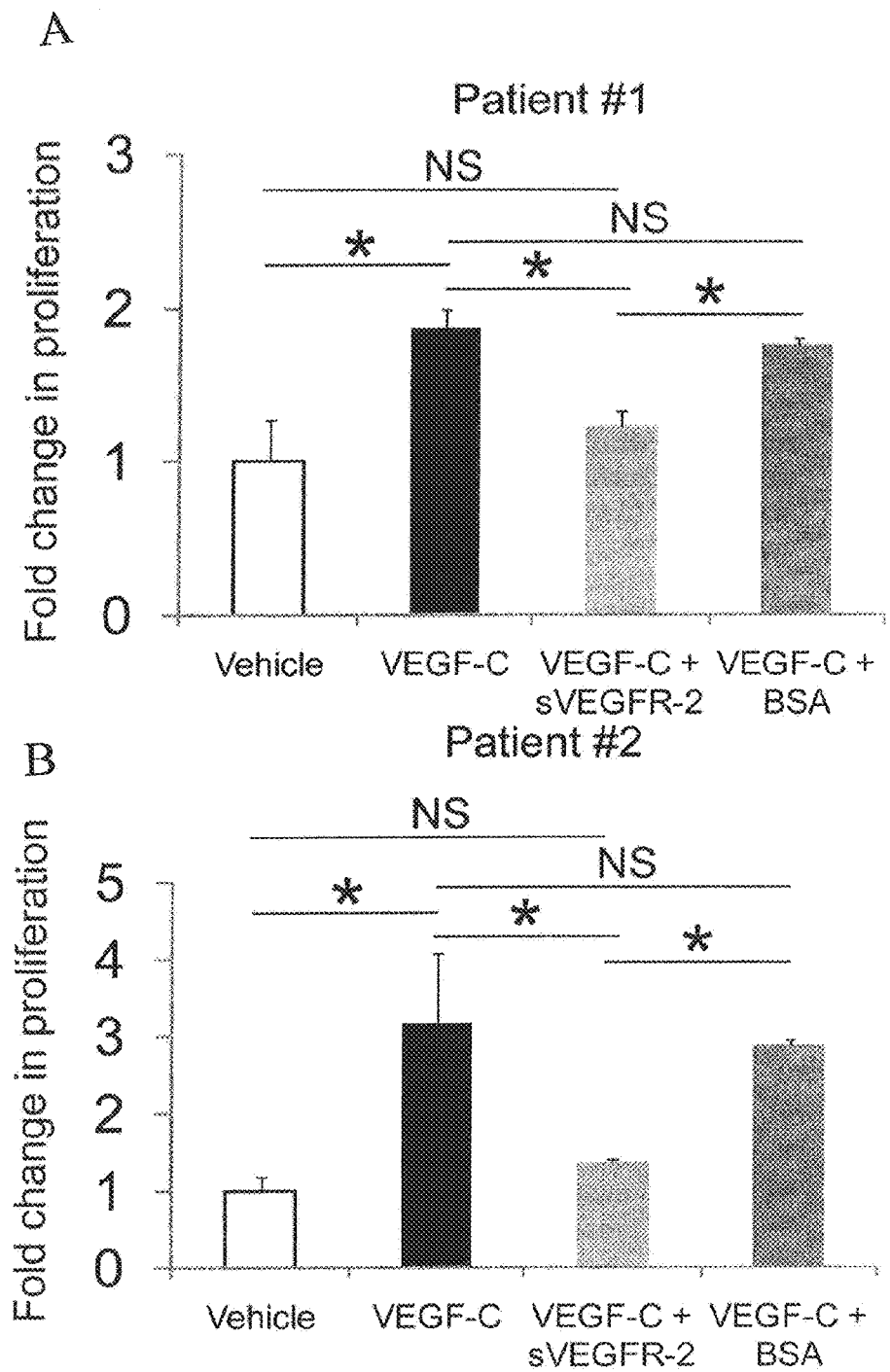
FIG. 27 demonstrates sVEGFR-2 abolishes proliferation of human lymphangioma endothelial cells. VEGF-C-induced proliferation of lymphatic endothelial cells isolated from two children with 24 lymphangioma was abolished by sVEGFR-2 (25 μg/ml). ((a, Patient #1 is a 10-month old child; b, Patient #2 is a 4-month-old child; n=6-9. (NS, not significant; *, P<0.05; Significance by Mann Whitney U test. Error bars depict s.e.m.)

Lymphatic endothelial cells were isolated from lymphangiomas of 4-month-old and 10-month-old children (Huang, X., et al., *Biochem Biophys Res Commun* 252, 643-648 (1998)) were grown in EGM2-MV growth media containing 5% FBS. Cells were passaged onto a 96-well plate (5000 cells/well) in basal media (MCDB131) containing 2% FBS, and allowed to adhere overnight. Cultures were then treated with 200 ng/ml recombinant human wild-type (WT) VEGF-C (Reliatech) alone or together with 25 µg/ml of sVEGFR-2 (Reliatech) in basal media with 0.1% FBS. Cell proliferation was measured after 24 h by using BrdU cell proliferation kit (Chemicon) according to the manufacturer's instructions. The results are presented in FIG. 27. VEGF-C-induced proliferation of lymphatic endothelial cells (a, Patient #1 is a 10-month old child; b, Patient #2 is a 4-month-old child) was abolished by sVEGFR-2 (25 µg/ml). n=6-9. NS, not significant; *, P<0.05; Significance by Mann Whitney U test. Error bars depict s.e.m.

Example 13

Non-Ocular Role of sVEGFR-2

Figure 28:
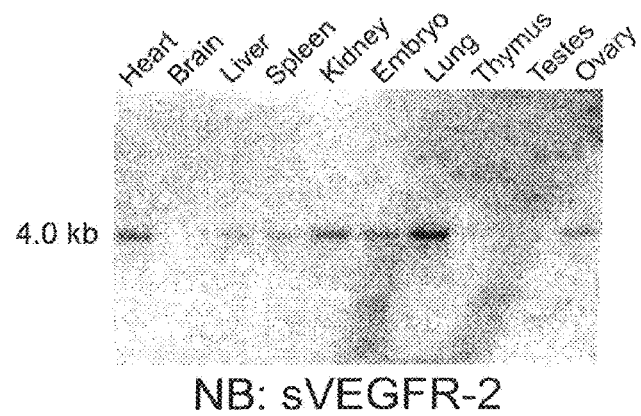
FIG. 28 depicts a northern blot using poly(A) positive RNA from various mouse organs revealed a 4 kb band corresponding to sVegfr2 and demonstrates that Vegfr2 expression is widespread.
Figure 29:
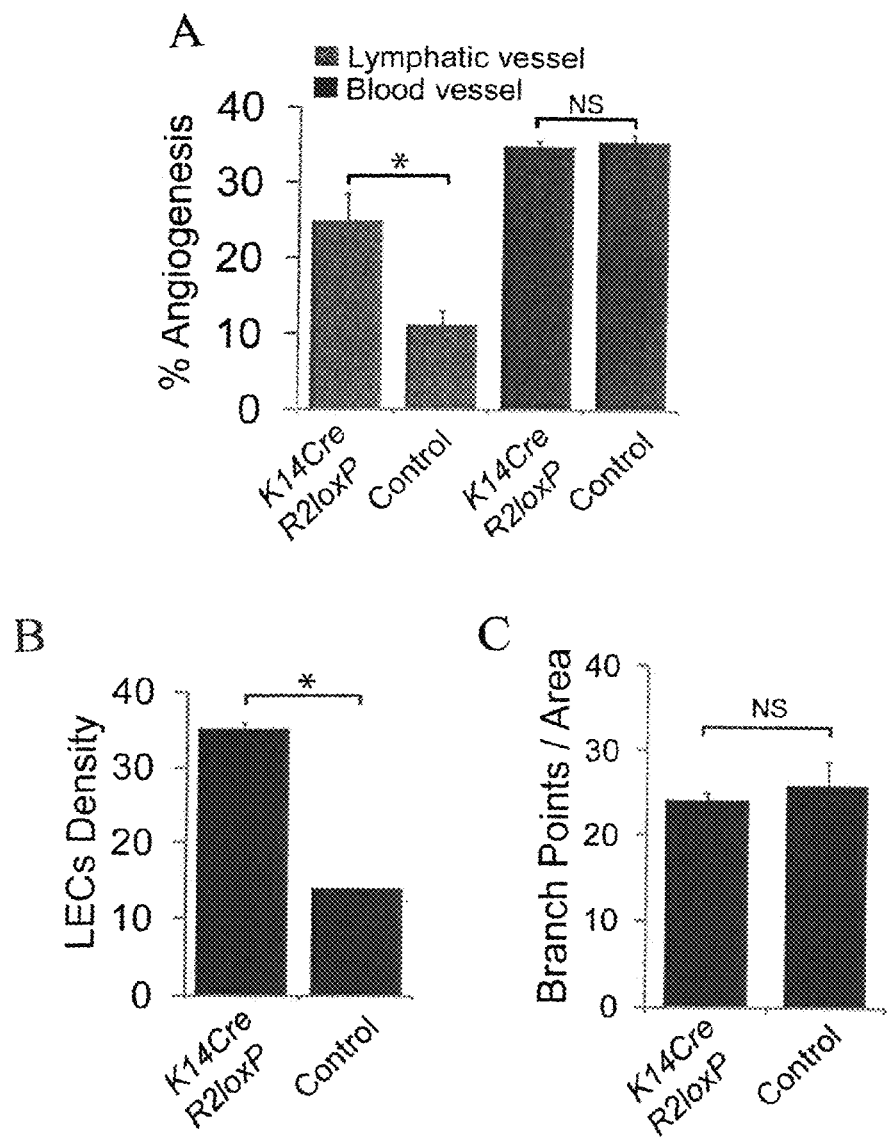
FIG. 29 demonstrates the loss of sVegfr2 in the skin induces lymphatic hyperplasia. (A) Skin area occupied by blood vessels (CD31+/LYVE-1−, black bars) was unaffected by loss of sVEGFR-2; however, the area occupied by lymphatic vessels (LYVE-1+, grey bars) was increased in P0 K14Cre/Vegfr2$^{loxP/loxP}$ mice compared to littermate controls. (B) Lymphatic endothelial cell (LEC) density, quantified by number of Prox1+ (black) nuclei per 100 μm of lymphatic vessel (LYVE-1+, grey) length, is increased in P0 K14Cre/Vegfr2$^{loxP/loxP}$ mice compared to littermate controls. (C) Quantitative branch point analysis of LYVE-1+ lymphatic vessels per unit area (750 μm×750 μm) showed no difference between K14Cre/Vegfr2$^{loxP/loxP}$ mice and littermate controls. (b,d,e) (NS, not significant; *, P<0.05; Significance by Mann Whitney U test. n=14 (A), n=12 (B), n=8 (C). Error bars depict s.e.m.)

We found sVegfr2 expression by Northern blotting of poly A-enriched RNA isolated from various mouse organs (FIG. 28), suggesting that sVEGFR-2 might have functional roles outside the eye. In situ hybridization with a sVegfr2 probe demonstrated that sVegfr2 mRNA expression was abundant in the alymphatic epidermis of the skin as well as in the hair follicles of wild-type mice. The sVEGFR-2 protein was immunolocalized in the epidermis, hair follicles, and, consistent with its ability to diffuse, also in the dermis of wild-type mice. In contrast, mbVEGFR-2 was expressed in the skin vasculature, but not in the epithelial cells or hair follicles. As in the cornea, VEGF-C was expressed in the P0 wild-type mouse skin but undetectable in the adult. Excess VEGF-C in the skin, achieved by either transgenic overexpression or implantation of overexpressing cells, leads to hyperplasia but not sprouting of lymphatic vessels (Jeltsch, M., et al. *Science* 276, 1423-1425 (1997), Goldman, J., et al., *Circ Res* 96, 1193-1199 (2005)). To determine the function of sVEGFR-2 in the skin, we interbred Vegfr2$^{loxP/loxP}$ mice with K14Cre mice that constitutively and uniformly express Cre recombinase in the epidermis and hair follicles (Vasioukhin, V., et al., *Proc Natl Acad Sci USA* 96, 8551-8556 (1999)). This strategy specifically targets sVEGFR-2 because the epidermis and hair follicles express sVEGFR-2 but not mbVEGFR-2. Strikingly, in all P0 K14Cre/Vegfr2$^{loxP/loxP}$ mouse skin, which lacked sVEGFR-2 expression, there was dramatic enlargement of lymphatic vessels compared to those in littermate control skin (FIG. 29A). These dilated skin lymphatics in K14Cre/Vegfr2$^{loxP/loxP}$ mice also were hyperplastic (FIG. 29B). However, the density of lymphatic structures, as quantified by branch point analysis, was not greater in K14Cre/Vegfr2$^{loxP/loxP}$ mice, just as in mouse skin exposed to excess VEGF-C (FIG. 29C). In contrast to the lymphatic architectural changes, there was no increase in skin blood vessel diameter or density in K14Cre/Vegfr2$^{loxP/loxP}$ mice. The recapitulation of VEGF-C overexpression induced selective lymphatic hyperplasia in mice lacking sVEGFR-2 further supports sVEGFR-2 acting as an in vivo antagonist of VEGF-C.

Figure 30:
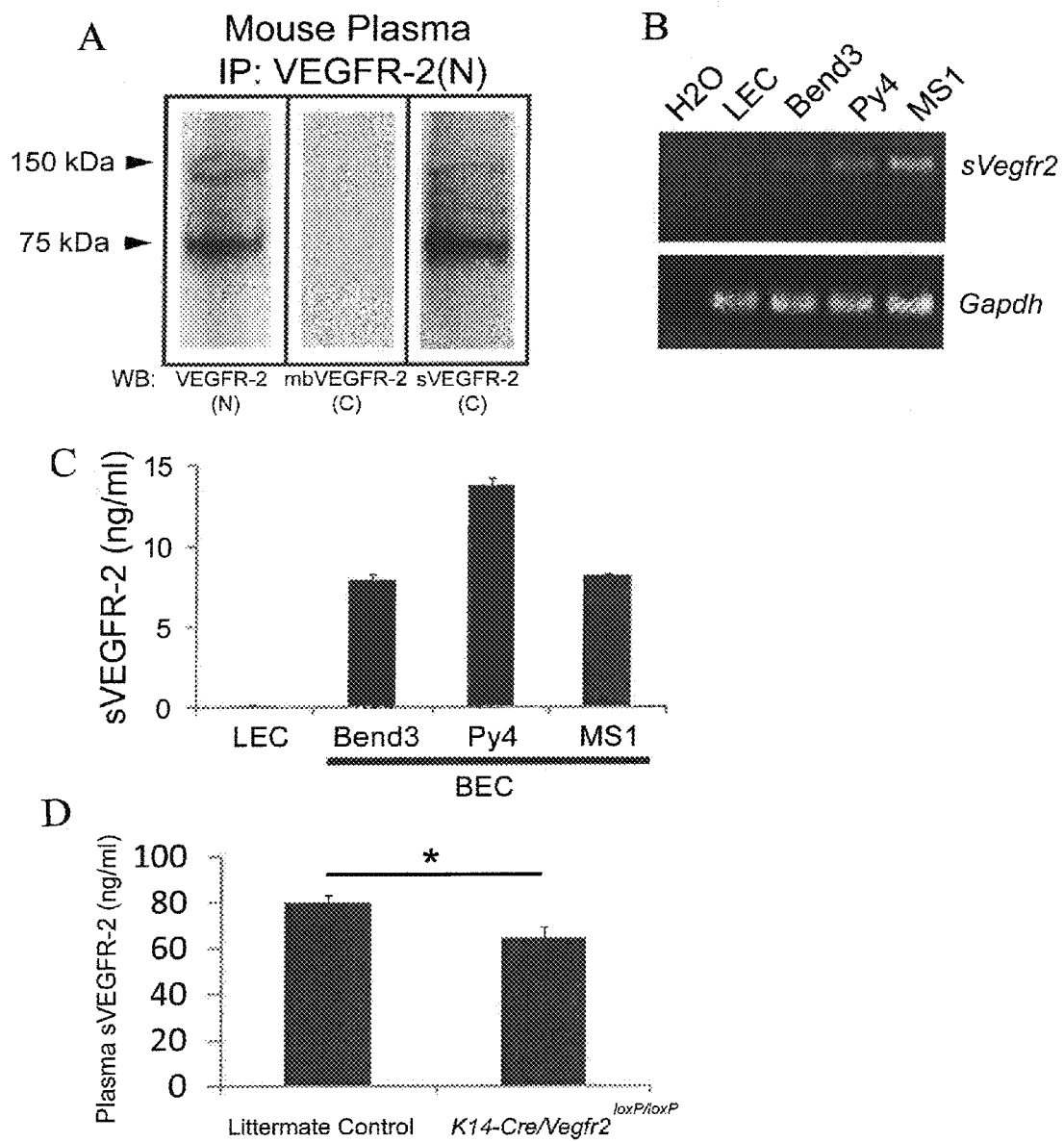
FIG. 30 demonstrates sVEGFR-2 is produced by blood endothelial cells (BECs) and skin epithelium and circulates in plasma: (A) Depicts representative western blots of mouse plasma immunoprecipitated with an antibody against the amino terminus of VEGFR-2 (N) and immunoblotted with either anti-VEGFR-2 (N; left), or anti-sVEGFR-2 (C; right) revealed identical immunoreactive species. These species were not detected by immunoblotting using an antibody against the carboxyl terminus of mbVEGFR-2 (C; center); (B) Depicts PCR amplification of sVegfr2 mRNA using cDNA derived from mouse lymphatic endothelial cells (LECs) and mouse BECs isolated from the brain (Bend3), Skin (Py4) and pancreas (MS1) showing higher expression of sVEGFR-2 in BECs compared to LECs. Adjacent lane (H$_2$O) shows template negative control. Gapdh was loading control (lower band), n=5; (C) Depicts that ELISA corroborates PCR data by showing that sVEGFR-2 protein is secreted by blood endothelial cells, but not lymphatic endothelial cells, n=3. Immunofluorescence revealed sVEGFR-2 expression by the pulmonary microvasculature (CD31+ vessel) (data not shown); (D) Demonstrates that ELISA reveals reduced sVEGFR-2 levels in plasma of K14Cre/Vegfr2$^{loxP/loxP}$ mice compared to its littermate controls. *, P<0.05; Significance by Mann Whitney U test. n=16. Error bars depict s.e.m. (c,e).

A protein immunoreactive to an antibody recognizing the amino-terminus of VEGFR-2 has been detected in plasma and shown to be a surrogate biomarker of tumor growth (Ebos, J. M., et al. *Mol Cancer Res* 2, 315-326 (2004); Ebos, J. M., et al. *Cancer Res* 68, 521-529 (2008); Ebos, J. M., *Proc Natl Acad Sci USA* 104, 17069-17074 (2007)). However, its molecular identity (whether it is encoded by a splice variant of Vegfr2 or derived from ectodomain shedding or proteolytic cleavage of mbVEGFR-2) and cellular source have been elusive. We found that the circulating VEGFR-2 in plasma was immunoreactive to both AA21127 and T014 but not an antibody recognizing the carboxyl-terminus of mbVEGFR-2 (FIG. 30A). Mouse blood endothelial cell (BEC) lines derived from the microvasculature of the brain, pancreas, or skin all synthesized and secreted sVEGFR-2, far in excess of LEC production (FIG. 30B,C). Also sVEGFR-2 was detected by immunofluorescence using AA21127 in mouse lung microvasculature, identifying BECs as sources of plasma sVEGFR-2. Without wishing to be bound by theory, the production of anti-lymphangiogenic sVEGFR-2 by BECs could be one of the mechanisms underlying the observation that lymphangiogenesis typically lags behind hemangiogenesis in many neovascular models. Surprisingly, plasma levels of sVEGFR-2 were significantly lower in K14Cre/Vegfr2$^{loxP/loxP}$ mice compared to littermate controls (FIG. 30D), suggesting that the skin epithelium also is a source of circulating sVEGFR-2. An earlier report showing that K14-driven recombinant soluble VEGFR-3 led to measurable circulating levels of the engineered protein 40 supports the concept that endogenous skin-derived sVEGFR-2 also can enter the circulation.

Materials and Methods

Corneal injury. Suture injury was performed as previously reported (Cursiefen, C., et al. VEGF-*J Clin Invest* 113, 1040-1050 (2004)). Naked plasmids coding for Cre-recombinase (gift of R. K. Nordeen, University of Colorado), mouse sVEGFR-2 (psVEGFR-2), mouse VEGF-A (pmVEGF-A, Addgene plasmid 10909), VEGF-C (pmVEGF-C, gift of K. Miyazono, University of Tokyo, Japan), VEGF-D (pmVEGF-D, Open Biosystems, 3028644) and human VEGF-D (ph-VEGF-D, TrueClone, Origene, SC122680), were utilized for in vivo enforced expression studies as shown earlier (Ambati, B. K., et al. *Nature* 443, 993-997 (2006)). VEGFR-2/Fc chimera (5 µg, R&D Systems), human IgG/Fc (5 µg, Jackson Immunoresearch), or sVEGFR-2 (5 µg) were injected in the cornea with 33-gauge needle (Ambati, B. K., et al. *Nature* 443, 993-997 (2006)). Corneal grafts from donor C57B1/6J mice (The Jackson Laboratory) were transplanted into recipient Balb/C (The Jackson Laboratory) mice and clinically evaluated for 8 weeks as previously described 52. VEGFR-3 inhibition was achieved by systemic administration (daily intraperitoneal injections) of MAZ51 (8 mg/kg, EMD Chemicals).

Immuno-morphometric analyses. Immunostaining and flat mounting were performed as previously shown (Ambati, B. K., et al. *Nature* 443, 993-997 (2006)) using rabbit anti-mouse LYVE-1 antibody (Abcam; 1:333), rat anti-mouse CD31 antibody (BD Biosciences; 1:50), rat-anti-mouse MECA-32 antibody (BD Biosciences; 1:10), goat anti-mouse LYVE-1 antibody (R&D, 1:100), and rabbit anti-mouse Prox-1 (Angiobio; 1:500) for 48 h at 4° C. Alexa Fluor 488 (goat anti-rabbit; 1:200) and Alexa Fluor594 (goat anti-rat; 1:200), Alexa Fluor488 (donkey anti-goat; 1:200, Invitrogen), or Cy3 conjugated donkey anti-rabbit (Jackson ImmunoResearch; 1:400) for 24 h were used as secondary antibodies. Tissue mounts were visualized under fluorescent microscopy (Leica SP-5) and analyzed with ImageJ (NIH). Mean percentage LYVE-1$^+$ (lymphatic vessels) or CD31$^+$/LYVE-1$^-$ (blood vessels) areas were calculated for corneal flat mounts and skin whole mounts using ImageJ software.

The number of Prox1+ nuclei within LYVE-1+ skin lymphatic vessels were counted in 12 random fields and expressed as LEC density per 100 μm. The density of lymphatic structures was determined by counting lymphatic vessel branch points per unit area (750 μm×750 μm) on standard low-magnification LYVE-1– stained images of the mouse skin.

Animals. Balb/C, C57B1/6J, and K14Cre mice were purchased from The Jackson Laboratory. Vegfr2$^{loxP/loxP}$ (flox) mice were generated as described below. LeCre mice1, which constitutively and uniformly express Cre recombinase in the cornea were a gift of R. Ashery-Padan and P. Gruss via D. C. Beebe. For all procedures, anesthesia was achieved by intraperitoneal injection of 50 mg/kg ketamine hydrochloride (Fort Dodge Animal Health, Wyeth) and 10 mg/kg xylazine (Phoenix Scientific). Experiments were approved by institutional review boards and conformed to the Association for Research in Vision and Opthalmology Statement on Animal Research. Generation of Vegfr2-flox mice. The targeting vector for a conditional allele for the Vegfr2 gene was constructed as follows. A 4.8 kb genomic fragment between HindIII and SmaI from the Vegfr2 locus harboring the first exon was subcloned and a single loxP site was introduced into EcoRI site with a disruption of the original site. A 5.7 kb genomic fragment between SmaI and SalI from the Vegfr2 locus was subcloned into the vector mentioned above, followed by the insertion of a construct harboring another loxP site and PGK-neo cassette flanked by frt sites. PGK-HSV-tk cassette was added to the targeting vector at the end. The vector was linearized with NotI and electroporated into R1 ES cells. Correctly targeted ES cell lines (Vegfr2-flox-neo allele) were verified by Southern blot analysis. Chimeric mice were generated by morula aggregation (Nagy et al. *PNAS USA* 90:8424-8428 (1993)), and males were crossed with ICR (Harlan Sprague Dawley) random outbred females. After successful germline transmission of the targeted allele, the PGK-neo cassette flanked by frt sites was removed to establish Vegfr2-flox allele by crossing with an FLPe deleter strain (Rodriguez et al., *Nat. Genet.* 25:139-140 (2000)). Deletion was verified by Southern blotting and PCR analysis. To test the deletion of the exon 1 from the Vegfr-2 gene (Vegfr2-del1 allele), Vegfr2-flox heterozygous mice were crossed with a Cre deleter strain (a gift from A. Nagy, Samuel Lunenfeld Research Institute, Toronto, Canada). Deletion was verified by Southern blotting and PCR analysis. We also confirmed that the embryonic phenotype of Vegfr2$^{del1/del1}$ mice was identical to that of Vegfr2$^{-/-}$ mice (data not shown)(Shalaby et al., *Nature* 376:62-66 (1995)). PCR analysis for genotyping Vegfr2 mutant mice was performed with tail DNA at an annealing temperature of 65° C. with the following primers:

```
                                       SEQ ID NO: 34
Vegfr-2-S1, 5'-TGGAGAGCAAGGCGCTGCTAGC-3';

SEQ ID NO: 35
Vegfr-2-A,  5'-CTTTCCACTCCTGCCTACCTAG-3';
and

SEQ ID NO: 36
Vegfr-2-S2, 5'-AATTTGGGTGCCATAGCCAATC-3'.
```

The wild-type, flox, del1 alleles gave 322-bp, 439-bp, and 218-bp bands, respectively.

Conditional Vegfr2 gene ablation. We achieved embryonic conditional genetic ablation of Vegfr2 in the cornea by cross-breeding Vegfr2$^{loxP/loxP}$ mice with LeCre mice (Asherey-Padan et al., *Genes Dev.* 14:2701-2711 (2000)). Alternatively, to target Vegfr2 in the adult mouse cornea, we performed intracorneal injections of naked plasmids5 containing the sequence for Cre recombinase (pCre; 20 μg; gift of R. K. Nordeen, University of Colorado) or an empty plasmid (pNull; 20 μg) in fellow eyes of Vegfr2$^{loxP/loxP}$ or BALB/c mice 3 days prior to suture placement. To achieve embryonic conditional genetic ablation of Vegfr2 in the epidermis, we cross-bred Vegfr2$^{loxP/loxP}$ mice with K14Cre mice that constitutively express Cre recombinase in the skin epidermis and hair follicle.

Corneal Suture Placement. Two intrastromal 11-0 sutures (Mani, Japan) were placed in the mouse cornea 180° from each other. All sutures were placed in the midpoint between the limbus and the corneal apex. They were left in place for up to 14 days.

Corneal Transplantation. Following anesthesia, donor corneal grafts were excised from a central 2-mm corneal button using trephine and Vannas scissors (Inami, Japan). The corneal buttons were kept in cold sterile PBS until the time of transplantation. The recipient corneal graft beds were prepared by similarly removing 1 0.5-mm corneal button, with trephine and Vannas scissors (Inami, Japan). The donor corneas were held in place by 10-12 interrupted 11-0 sutures (Mani, Japan). Antibiotic ointment (Poly-Bac, Akorn) were applied to the corneal surface for 8 days after surgery and sutures were removed 7 days after the procedure. Recombinant VEGFR-2/Fc (10 μg, R&D Systems), IgG/Fc (10 μg, Jackson Immunoresearch) or sVEGFR-2 (10 μg) were injected in the corneal bed immediately before transplantation. Post-operative evaluations were performed under a biomicroscope on a weekly basis by 2 independent examiners. Mice with post surgical complications (i.e., synechiae, hyphema, cataract, collapsed anterior chamber) were excluded from the study. Transplant survival was determined by an established semi-quantitative method 6 based on the clinical appearance of the grafted corneas: corneas with an opacity score>2 (Moderate stromal opacity, where pupil is visible and iris obscured) lasting for over 8 weeks were considered rejection.

sVEGFR-2 overexpression vector construction. The cloned nucleic acid molecule containing the coding sequence of sVegfr2, SEQ ID NO: 2, was extracted from agarose gel, sequenced and inserted into a pcDNA3.1 (Invitrogen) overexpression vector (psVEGFR-2) according to manufacturer instructions.

sVEGFR-2 enforced expression. Human embryonic kidney (HEK) 293 cells were cultured in DMEM (Invitrogen) containing 10% FBS, penicillin G (100 units/ml), streptomycin sulfate (0.1 mg/ml) (all from Sigma Aldrich) at 37° C., 10% $CO_2$ and 90% room air. Upon attaining 80% confluence the cells were transfected (Lipofectamine 2000, Invitrogen) with psVEGFR-2 or an empty pcDNA3.1 plasmid (pNull) in serum-free media. Supernatant fractions from the media were collected 24 h following serum starvation and analyzed for protein content. Similarly, intracorneal corneal injections (20 μg) of psVEGFR-2 or pNull were performed in vivo for enforced expression studies.

Corneal angiogenesis assay. Corneas were transfected in vivo (Ambati et al., *Nature*, 443(7114): 993-7, 2006; Stechschulte et al., *Invest. Opthalmol. Vis. Sci.* 42:1975-"979 (2001)) by intracorneal injections of naked plasmids (4 μg) coding for mouse VEGF-A (Addgene plasmid 10909), VEGF-C (gift of K. Miyazono, University of Tokyo, Japan), VEGF-D (Open Biosystems, 3028644) and human VEGF-D (TrueClone, Origene, SC 122680). Plasmids coding for sVEGFR-2 (psVEGFR-2) or pNull (empty plasmid-fellow eye) and VEGFR-2/Fc or sVEGFR-2 (5 μg) were co-administered into the cornea at day 0 and day 7. At day 14, mice were euthanized and angiogenesis was quantified by corneal flat mounts as previously described (Ambati et al., Nature, 443(7114): 993-7, 2006).

VEGFR-3 inhibition. Daily intraperitoneal injections of VEGFR-3 tyrosine kinase inhibitor (MAZ5 1, EMD Chemicals, 8 mg/kg) were performed in pCre treated Vegfr2$^{loxP/loxP}$ mice after corneal suture placement for 14 consecutive days. Vehicle only (DMSO) was given as control treatment.

Generation of sVEGFR-2 specific antibody. Peptide synthesis was performed from C-terminus to N-terminus using Fmoc chemistry and a solid support resin. Synthesized peptides were purified and examined by MALDI-TOF mass spectrometry and reversed phase HPLC. Purified peptides include an N-terminal cysteine for directional conjugation to the carrier protein keyhole-limpet hemocyanin (KLH). Peptide immunogens conjugated to KLH were used to generate immune responses in rabbits (pathogen-free, barrier-raised New Zealand White Rabbits). Immunizations and sera collections were performed using a 79-day immunization protocol, then the sera was purified using proprietary peptide affinity chromatography techniques (ECM Biosciences).

Enzyme Linked Immunosorbent Assay (ELISA). Microtiter plates (96-well; Pierce) were incubated with 10 ng/well purified peptides (21127) or control peptide for 2 h at RT. After two washing steps with PBS to remove unbound peptide, plates were blocked with 3% BSA in PBS. Next, purified rabbit antibody targeted against the C-terminus sequence of sVEGFR-2 (AA2 1127) was added at various dilutions for 1 h. Plates were washed twice with 0.1% Tween 20 in TBS, then incubated for 30 min with donkey anti-rabbit Ig coupled to horseradish peroxidase (1:10,000 in TBS; Jackson Immunoresearch). After washing with 0.1% Tween 20 in TBS, 100 µl of the colorimetric HRP substrate solution (OPD; Pierce) was added to each well. After 5 min, the reaction was stopped with 100 µl of 1 M $H_2SO_4$, and the plates were read at 650 nm in a microplate reader. ELISAs were also used according to the manufacturers' instructions to quantify sVEGFR-2 (Quantikine, R&D Systems) and VEGF-C (Bender, Reliatech). Measurements were normalized to total protein (Bio-Rad).

Immunohistochemistry. Deparaffinized sections were incubated with 10% normal goat serum (Vector Laboratories). Endogenous peroxidase and alkaline phosphatase were quenched with 3% H2O2 and levamisole (Vector Laboratories), respectively. Immunolocalization was performed with rabbit antibody against the unique C-terminus of sVEGFR-2 (1:500, AA21127), rabbit antibody against the C-terminus of mbVEGFR-2 (1:100, clone ab2349, Abcam), rabbit antibody against LYVE-1 (1:200, clone ab14917, Abeam), rabbit antibody against Prox1 (1:500, clone 102-PA32S, Angiobio) and goat antibody against VEGF-C (1:100, clone sc-25783, Santa Cruz Biotechnology). Biotin-streptavidin-horseradish peroxidase (Vector Laboratories), alkaline-phosphatase (Invitrogen), or immunofluorescence (Alexa Fluor 488 and 594, Invitrogen) methods were used. Counterstain was obtained with hematoxylin (Vector Laboratories) or DAPI (1:25,000, Molecular Probes). Substitution of isotype non-immune IgG for the primary antibody or pre-adsorption of the primary antibody with a ten-fold molar excess of the immunizing peptide was used to assess specificity of staining. Images were visualized under light or fluorescent confocal microscopy (Leica SP-5) and analyzed with ImageJ (NIH). Fluorescent images were thresholded equivalently and simultaneously.

Transmission electron microscopy. Eyes were enucleated from wild-type and LeCre/Vegfr2$^{loxP/loxP}$ mice and fixed in 3.5% glutaraldehyde/4% paraformaldehyde for 2 h followed by preparation of uranyl acetate- and lead citrate-stained ultrathin sections for transmission electron microscopy studies (Phillips Biotwin).

Corneal flat mounts and skin whole mounts. Following euthanasia the corneas and skin from the abdomen were isolated, washed in PBS and fixed in 4% paraformaldehyde for 1 h and acetone for 20 min at RT. They were then washed in 0.1% Tween 20 in PBS and blocked on 3% BSA in PBS for 48 h. Incubation with rabbit anti-mouse LYVE-1 antibody (Abeam; 1:333) and rat anti-mouse CD31 antibody (BD Biosciences; 1:50) or rat-anti-mouse MECA-32 antibody (BD Biosciences; 1:10) or goat anti-mouse LYVE-1 antibody (R&D Systems; 1:100) and rabbit anti-mouse Prox-1 (Angiobio; 1:500) were performed for 48 h at 4° C. The tissues were again washed in 0.1% Tween 20 in PBS and incubated with Alexa Fluor 488 (goat anti-rabbit; 1:200) and Alexa Fluor594 (goat anti-rat; 1:200) or Alexa Fluor488 (donkey anti-goat; 1:200; all from Invitrogen) and Cy3 conjugated donkey anti-rabbit (Jackson ImmunoResearch; 1:400) for 24 h. Tissue mounts were visualized under fluorescent microscopy (Leica SP-5) and analyzed with ImageJ (NIH).

PCR. RNA was isolated from mouse cornea using RNAqueous (Ambion) kit according to manufacturer instructions. Reverse Transcriptase PCR was carried out with Taqman (Applied Biosystems) per manufacturer instructions. Amplification of sVegfr2 fragment encompassing the splicing site (Exon13-Intron13 junction) and the complete ORF was performed with the following primers: 5'-CGAG-GAGAGAGGGTCATCTC-3'SEQ ID NO:37 (forward)/5'-CAGGGATGCCTCCATACC-3' SEQ ID NO:38 (reverse) and 5'-GCTCTGTGCCCAGCGCGAGGTGCAGGAT-3' SEQ ID NO:39 (forward)/5'-TGCTCTGCTTCCAGGAGT-GTGCCAGCCT-3' SEQ ID NO:40 (reverse), respectively. Amplification of loading control Gapdh was performed with the following primers: 5'-AACTTTGTGAAGCTCATTTC-CTGGTAT-3' SEQ ID NO:41 (forward)/5'-CCTTGC TGGGCTGGGTGGT-3' SEQ ID NO:42 (reverse). mbVegfr2 primers were proprietary from Maxim Biotech. Positive control was mbVegfr2 cDNA (Maxim Biotech).

3'-RACE PCR. 3'RACE ready cDNA was generated from total RNA using the following primer: 5'-AGAGAATTCAC-CGGATCCTACCCGGGTTTTTTTTTTTTTTTTT-3' SEQ ID NO:43. Three potential polyadenylation signal sequences at positions 2360-5 (PolyA1), 3 165-70 (PolyA2) and 3956-61 (PolyA3) within intron 13 of Vegfr2 were predicted by PolyA SMV 2.1 software 8. Primers were designed to encompass each of the three potential sites yielding an approximate 400 bp PCR product. Forward primers were as follow: 5' TGGTACAAGCTTGGTCTCACAGGCAACAT-3' SEQ ID NO:44 (PolyA1), 5'-GCCACACTCATTGCCTGTACTC-CTCTGG-3' SEQ ID NO:45 (PolyA2), 5'-ACTGCAGT-TGGGTGATTTTCAGGAGCAC-3' SEQ ID NO:46 (PolyA3). Reverse primer was 5'-GAGAATTCACCG-GATCCTAC-3' SEQ ID NO:47.

DNA sequencing. PCR products were cloned into TOPO TA vector (Invitrogen) and DNA sequencing was performed by the University of Kentucky Advanced Genetic Technologies Center using multi-color fluorescence based DNA sequencer (ABI 3730xl).

In situ hybridization. In situ hybridization was performed on cryosections as previously described (Ambati et al., Nature, 443(7114): 993-7, (2006)). Digoxigenin (DIG)-labeled sense and anti-sense riboprobes were transcribed from the mouse sVegfr2 cDNA using the DIG-RNA-labeling kit (Boehringer-Mannheim). The sVEGFR-2 probe targeted a 412 bp fragment (encompassing residues 3603 to 4015) at the unique 3' end of sVegfr2 mRNA. DIG-labeled probes were hybridized, washed and incubated with alkaline phosphatase-conjugated anti-DIG antibody (1:2000; Boehringer-Mannheim) and stained with BM purple (Roche).

Northern Blotting. For mRNA detection, commercially prepared membrane from Ambion containing 2 µg of polyA+ RNA isolated from various mouse organs and fractionated by agarose gel electrophoresis prior to transfer to the membrane were used. Membrane was hybridized in NorthernMax hybridization solution (Ambion) with radiolabeled probes targeted at the unique tail of sVegfr2 transcript (412 bp, encompassing residues 3603 to 4015 of sVegfr2) at 42° C. for 12 h, followed by two post-hybridization washes with 2×SSC, 0.1% SDS and two additional washes with 0.2×SSC, 0.1% SDS, all for 30 min each at 42° C. The blots were then exposed to a Typhoon phosphoimager screen for 3, then 7 d for image development. The radiolabeled probes were prepared with Prime-it labeling kit (Stratagene) using random primers, high specific activity a-32P-dCTP (6,000 Ci/mmole) and 25 ng of isolated PCR fragments for sVegfr2 according to the manufacturer's instructions.

Mouse endothelial cell culture. Mouse blood endothelial cells from brain (Bend3, gift of C. D. Kontos, Duke University), pancreas (MS 1) and skin (Py4, both gifts from J. L. Arbiser, Emory University) and mouse lymphatic endothelial cells (mLEC; ref. 9) were cultured in DMEM (Invitrogen) containing 10% FBS, penicillin G (100 units/ml), streptomycin sulfate (0.1 mg/ml) (all from Sigma Aldrich) at 37° C., 10% CO2 and 90% room air. Upon attaining 80% confluence these cells were serum starved for 24 h when supernatant fractions were collected for sVEGFR-2 protein quantification by ELISA. Total RNA was also extracted for RT-PCR.

Human lymphatic microvascular endothelial cell proliferation assay. Cultured human lymphatic microvascular endothelial cells (Cambrex) were maintained in EGM-2 MV (Clonetics) supplemented with 10% FBS and antibiotics at 37° C. under 5% CO2. Once confluent cells were plated at 96-well plate at a density of 30,000 cells/well. Cells were serum starved for 2 h and then exposed to media alone (MCDB 131+5% FBS), VEGF-C (200 ng/ml; R&D Systems) enriched media or VEGF-C enriched media with sVEGFR-2 (13.6 µg/ml). This concentration of sVEGFR-2 corresponds to a molar ratio of approximately 11-13:1 compared to VEGF-C, and is therefore physiological in view of our finding that sVEGFR-2 levels in the cornea are ~20-fold higher than VEGF-C levels on a molar basis. Proliferation was quantified using BrdU uptake (Chemicon International) at 36 h after incubation with VEGF-C.

Lymphangioma proliferation assay. Lymphatic endothelial cells, isolated from lymphangiomas in 4-month-old and 10-month-old children (Huang, X., et al., *Biochem Biophys Res Commun* 252, 643-648 (1998)), were grown in EGM2-MV growth media containing 5% FBS. Cells were passaged onto a 96-well plate (5000 cells/well) in basal media (MCDB131) containing 2% FBS, and allowed to adhere overnight. Cultures were then treated with 200 ng/ml recombinant human wild-type (WT) VEGF-C (Reliatech) alone or together with 25 µg/ml of sVEGFR-2 (Reliatech) in basal media with 0.1% FBS. Cell proliferation was measured after 24 h by using BrdU cell proliferation kit (Chemicon) according to the manufacturer's instructions.

Western blotting. Mouse cornea lysates as well as cell culture supernatant were resolved by SDS 8% or 4-20% polyacrylamide gradient gel electrophoresis (PAGE) and transferred to nitrocellulose (NC) membranes. Immunoblotting was performed using a rabbit antibody against the amino terminus of mouse VEGFR-2 (1:1000; clone T014; ref. 11), custom made sVEGFR-2 specific antibody (1:1000; AA21127) and loading was assessed using rabbit antibody against human GAPDH (1:2000; Abcam).

Silver staining. VEGFR-2/Fc or sVEGFR-2 were resolved by SDS 10% PAGE and stained using SilverSNAP (R) Stain (Pierce) according to manufacturer instructions. Immunoprecipitation studies. Recombinant mouse sVEGFR-2 (2 µg) was incubated with mouse recombinant VEGF-C (100 ng, Biovision) in PBS at 4° C. for 1 h. Immunoprecipitation was carried out with 2 µg of an anti-VEGFR-2 antibody or an isotype control IgG. Immobilized protein A/G beads (20 µl, Pierce) were used for precipitation. Samples were boiled, resolved by SDS-PAGE with respective positive controls (rs-VEGFR-2 and rVEGF-C) and transferred to a NC membrane. Rabbit antibodies against VEGF-C (1:1000, Santa Cruz) and VEGFR-2 (1:1000, T014) were used to probe for VEGF-C and VEGFR-2 respectively. Immunoprecipitation of VEGFR-2 from mouse plasma was performed as described previously by others 12. Rabbit antibody against VEGFR-2 (T014, 2 µg) was employed for immunoprecipitation. T014 (1:1000), rabbit anti-VEGFR-2 (C) antibody (1:1000, clone ab2349, Abcam) or rabbit anti-sVEGFR-2 antibody (1:1000, AA21 127) was used for immunoblotting. Mouse LECs were incubated with media only or VEGF-C (200 ng/ml, Biovision) with or without sVEGFR-2 (13.8 µg/ml) or VEGFR-1/Fc (20 µg/ml, R&D Systems) for 15 min. The sVEGFR-2 and VEGFR-1/Fc concentrations are equimolar. The lysates were immunoprecipitated with anti-VEGFR-3 antibody (Santa Cruz, C-20), immunoblotted with anti-phosphotyrosine (1:1000, 4G10, Millipore), and reblotted with anti-VEGFR-3 antibody (1:500, AFL4, eBioscience).

Statistical analyses. Mean percentage LYVE-1$^+$ (lymphatic vessels) or CD3 1$^+$/LYVE-1$^-$ (blood vessels) areas were calculated for each corneal flat mount and skin whole mount using ImageJ software. The number of Prox1$^+$ nuclei within LYVE-1$^+$ skin lymphatic vessels were counted in 12 random fields and expressed as LEC density per 100 µm. The density of lymphatic structures was determined by counting lymphatic vessel branch points per unit area (750 µm×750 µm) on standard low-magnification LYVE-1– stained images of the mouse skin. Mann Whitney U test with Bonferroni correction was used for statistical comparison of multiple variables. Comparison of corneal transplant survival was performed by Kaplan-Meier Survival. The null hypothesis was rejected at $P<0.05$.

We claim:

1. A vector comprising an isolated nucleic acid molecule consisting of (i) a nucleotide sequence of SEQ ID NO:4 or (ii) a degenerate sequence of SEQ ID NO:4, wherein said degenerate sequence encodes a polypeptide consisting of the amino acid sequence set forth in SEQ ID NO:5, wherein the nucleic acid molecule is in operable linkage with a promoter.

2. An isolated recombinant host cell comprising the the vector of claim 1.

3. The vector of claim 1, wherein the promoter is heterologous to the nucleic acid molecule.

4. The isolated recombinant host cell of claim 2, wherein the promoter is heterologous to the nucleic acid molecule.

* * * * *